United States Patent [19]
Matsuo et al.

[11] Patent Number: 6,087,357
[45] Date of Patent: Jul. 11, 2000

[54] PIPERAZINE DERIVATIVES AS TACHYKININ ANTAGONISTS

[75] Inventors: Masaaki Matsuo, Toyonaka; Takashi Manabe, Kawanishi; Nobukiyo Konishi, Nagaokakyo; Kazuhiko Take, Tondabayashi; Norihiro Igari; Shinji Shigenaga, both of Kobe; Hiroshi Matsuda, Osaka; Tadashi Terasaka, Ikeda, all of Japan

[73] Assignee: Fujisawa Pharmaceutical Co., Ltd., Osaka, Japan

[21] Appl. No.: 09/091,269

[22] PCT Filed: Dec. 12, 1996

[86] PCT No.: PCT/JP96/03641

§ 371 Date: Jun. 18, 1998

§ 102(e) Date: Jun. 18, 1998

[87] PCT Pub. No.: WO97/22597

PCT Pub. Date: Jun. 26, 1997

[30] Foreign Application Priority Data

Dec. 18, 1995 [GB] United Kingdom .................... 9525841
May 16, 1996 [AU] Australia ................. PN9891
Sep. 30, 1996 [AU] Australia ................. PO2683

[51] Int. Cl.[7] ........................ A61K 31/54; A61K 31/535; C07D 417/00; C07D 413/00
[52] U.S. Cl. .................................. 514/227.8; 514/228.2; 514/235.8; 544/60; 544/62; 544/121
[58] Field of Search ................................ 544/62, 60, 121; 514/227.8, 228.2, 235.8

[56] References Cited

U.S. PATENT DOCUMENTS

| | | | |
|---|---|---|---|
| 3,935,214 | 1/1976 | Zellner | 514/227.8 |
| 5,164,388 | 11/1992 | De et al. | 514/235.8 |
| 5,238,938 | 8/1993 | Tone et al. | 514/253 |
| 5,344,830 | 9/1994 | Mills et al. | 514/235.8 |
| 5,670,505 | 9/1997 | Matsuo et al. | 514/253 |
| 5,672,602 | 9/1997 | Burkholder et al. | 514/253 |
| 5,840,726 | 11/1998 | Burkholder et al. | 514/253 |
| 5,883,098 | 3/1999 | Matsuo et al. | 514/253 |

*Primary Examiner*—Deborah C. Lambkin
*Attorney, Agent, or Firm*—Oblon, Spivak, McClelland, Maier & Neustadt, P.C.

[57] ABSTRACT

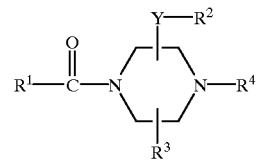

(I)

11 Claims, No Drawings

PIPERAZINE DERIVATIVES AS TACHYKININ ANTAGONISTS

This application is a 371 of PCT/JP96/03641 filed Dec. 12, 1996.

TECHNICAL FIELD

The present invention relates to new piperazine derivatives and a pharmaceutically acceptable salt thereof.

More particularly, it relates to new piperazine derivatives and a pharmaceutically acceptable salt thereof which have pharmacological activities such as Tachykinin antagonism, especially Substance p antagonism, Neurokinin A antagonism, Neurokinin B antagonism, and the like, to a process for preparation thereof, to a pharmaceutical composition comprising the same, and to a use of the same as a medicament.

Accordingly, one subject of the present invention is to provide new and useful piperazine derivatives and a pharmaceutically acceptable salt thereof which have pharmacological activities such as Tachykinin antagonism, especially Substance P antagonism, Neurokinin A antagonism, Neurokinin B antagonism, and the like.

Another object of the present invention is to provide a process for the preparation of said piperazine derivatives and a salt thereof.

A further object of the present invention is to provide a pharmaceutical composition comprising, as an active ingredient, said piperazine derivatives and a pharmaceutically acceptable salt thereof.

Still further object of the present invention is to provide a use of said piperazine derivatives or a pharmaceutically acceptable salt thereof as Tachykinin antagonist, especially Substance P antagonist, Neurokinin A antagonist or Neurokinin B antagonist, useful for treating or preventing Tachykinin-mediated diseases, for example, respiratory diseases such as asthma, bronchitis, rhinitis, cough, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g., migraine, headache, toothache, cancerous pain, back pain, etc.); and the like in human being or animals.

BACKGROUND ART

Some piperazine derivatives having pharmaceutical activities such as Tachykinin antagonism have been known as described in EP 0655442 A1.

DISCLOSURE OF INVENTION

The object compound of the present invention can be represented by the following general formula (I):

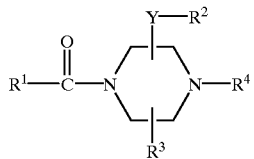

(I)

wherein

Y is bond or lower alkylene, $R^1$ is aryl which may have suitable substituent(s), $R^2$ is aryl or indolyl each of which may have suitable substituent(s), $R^3$ is hydrogen or lower alkyl, $R^4$ is chloro(lower)alkenyl;

chloro(lower)alkenyl; pyridyl(lower)alkylamino (lower)alkyl; pyridyl(lower)alkylamino(lower) alkenyl; N-(lower alkyl)-N-[pyridyl(lower)alkyl] amino(lower)alkyl; triazolylamino(lower)alkyl; lower alkoxy(lower)alkylamino(lower)alkyl; bis [(lower)alkoxy(lower)alkyl]amino(lower)alkyl; N-(lower alkyl)-N-[(lower)alkoxy(lower)alkyl] amino(lower) alkyl; hydroxy(lower)alkyl; lower alkylsulfonyloxy(lower)alkyl; phenyl(lower)alkyl which may have lower alkanoyl, amino, lower alkanoylamino, di(lower)alkylaminocarbonyl or nitro; lower alkoxyphenyl (lower)alkylcarbonyl; lower alkanoylbenzoyl; benzoyl(lower)alkyl which has lower alkyl, chlorine or di(lower)alkylamino; benzoyl(lower)alkyl which has halogen and lower alkyl; dihalobenzoyl(lower)alkyl; di(lower) alkylbenzoyl(lower)alkyl; 3-fluorobenzoyl(lower) alkyl; 3-(4-fluorobenzoyl)propyl; 4,4-ethylenedioxy-4-(4-fluorophenyl)butyl; piperazinylcarbonyl(lower)alkyl which has cyclopentyl or halophenyl; (2-pyridyl) (lower)alkyl; (3-pyridyl)propyl; (3-pyridyl) (lower)alkynyl; imidazolyl(lower)alkyl which may have lower alkyl; pyrazolyl(lower)alkyl which may have lower alkyl; thiomorpholinylcarbonyl(lower)alkyl; (3-azabicyclo [3.2.2]non-3-yl)carbonyl(lower)alkyl; or thienylcarbonyl(lower)alkyl, 1,2,3,6-tetrahydropyridyl(lower)alkyl, 1,2,3,6-tetrahydropyridyl(lower)alkynyl, 1,2,3,4-tetrahydroisoquinolyl(lower)alkyl, 4,5,6,7-tetrahydrothieno[3,2-c]pyridinyl(lower)alkyl, saturated heterocyclic(lower)alkyl, saturated heterocyclic(lower)alkenyl, saturated heterocyclic (lower)alkynyl, saturated heterocyclicamino(lower) alkyl, saturated heterocyclicamino(lower)alkenyl or saturated heterocyclicamino(lower)alkynyl, each of which may have suitable substituent(s), and a pharmaceutically acceptable salt thereof.

It is to be noted that the object compound (I) may include one or more stereoisomers due to asymmetric carbon atom (s) and double bond, and all of such isomers and a mixture thereof are included within the scope of the present invention.

It is further to be noted that isomerization or rearrangement of the object compound (I) may occur due to the effect of the light, acid, base or the like, and the compound obtained as the result of said isomerization or rearrangement is also included within the scope of the present invention.

It is also to be noted that the solvating form of the compound (I) (e.g. hydrate, etc.) and any form of the crystal of the compound (I) are included within the scope of the present invention.

According to the present invention, the object compound (I) or a salt thereof can be prepared by processes which are illustrated in the following schemes.

Process 1

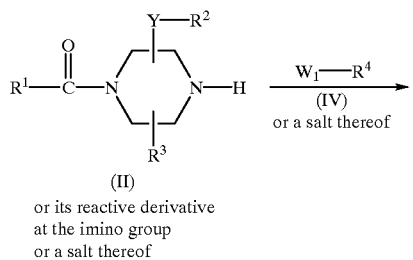
(II)
or its reactive derivative
at the imino group
or a salt thereof

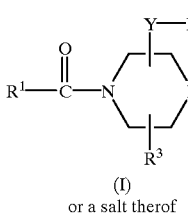
(I)
or a salt therof

Process 2

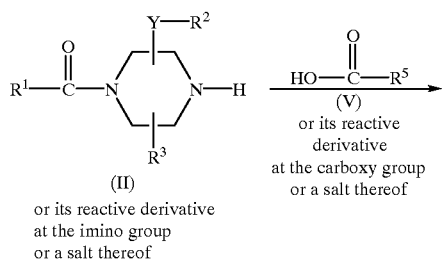
(II)
or its reactive derivative
at the imino group
or a salt thereof

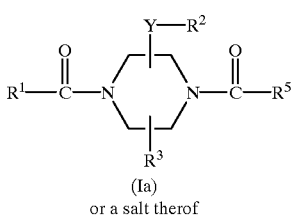
(Ia)
or a salt therof

Process 3

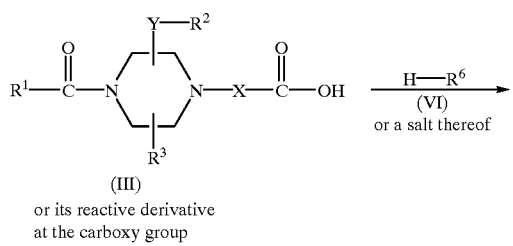
(III)
or its reactive derivative
at the carboxy group
or a salt thereof

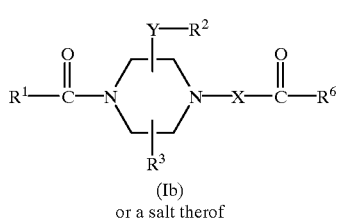
(Ib)
or a salt therof

Process 4

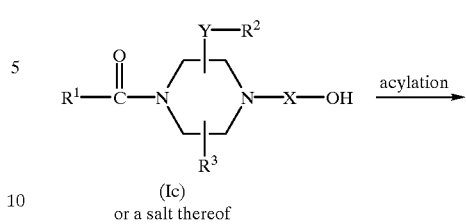
(Ic)
or a salt thereof

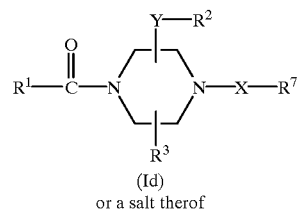
(Id)
or a salt therof

Process 5

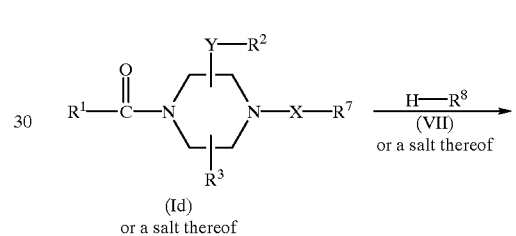
(Id)
or a salt thereof

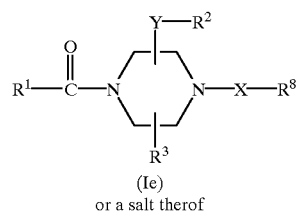
(Ie)
or a salt therof

Process 6

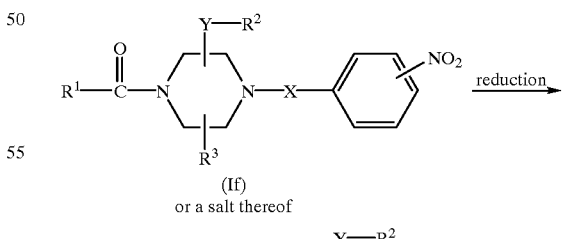
(If)
or a salt thereof

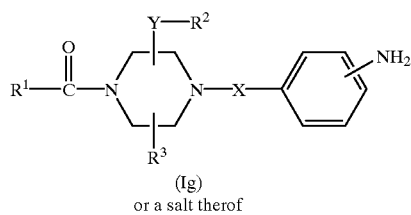
(Ig)
or a salt therof

Process 7

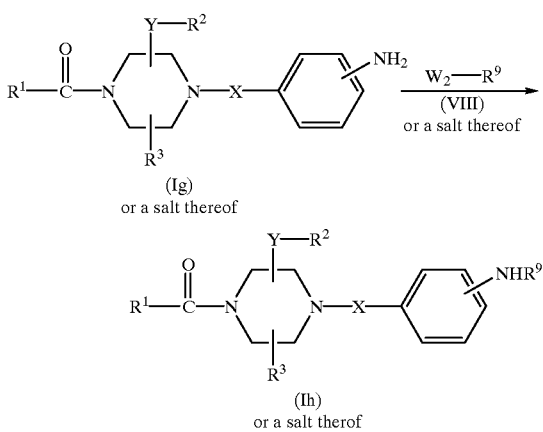

wherein Y, $R^1$, $R^2$, $R^3$ and $R^4$ are each as defined above, X is lower alkylene, $R^5$ is lower alkoxyphenyl(lower)alkyl or lower alkanoylphenyl, $R^6$ is piperazinyl which has cyclopentyl or halophenyl; or thiomorpholinyl, $R^7$ is acyloxy, $R^8$ is pyridyl(lower)alkylamino;

N-(lower alkyl)-N-[pyridyl(lower)alkyl]amino; triazolylamino; morpholinoamino; lower alkoxy(lower)alkylamino; bis[(lower)alkoxy(lower)alkyl]amino; N-(lower alkyl)-N-[(lower)alkoxy(lower)alkyl]amino; imidazolyl; pyrazolyl; or 1,2,3,6-tetrahydropyridyl, 1,2,3,4-tetrahydroisoquinolyl, 4,5,6,7-tetrahydrothieno[3,2-c]pyridinyl or saturated heterocyclic, each of which may have suitable substituent(s), $R^9$ is lower alkanoyl, and $W_1$ and $W_2$ are each a leaving group.

As to the starting compounds (II), (III), (IV), (V), (VI), (VII), and (VIII), some of them are novel and can be prepared by the procedures described in the Preparations and Examples mentioned later or similar manners thereto.

Suitable salts and pharmaceutically acceptable salts of the starting and object compounds are conventional non-toxic salt and include an acid addition salt such as an organic acid salt (e.g. acetate, trifluoroacetate, fumarate, maleate, tartrate, methanesulfonate, benzenesulfonate, formate, toluenesulfonate, etc.), an inorganic acid salt (e.g. hydrochloride, hydrobromide, hydroiodide, sulfate, nitrate, phosphate, etc.), or a salt with an amino acid (e.g. arginine, aspartic acid, glutamic acid, etc.), or a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention intends to include within the scope thereof are explained in detail as follows.

The term "lower" is intended to mean 1 to 6, preferably 1 to 4, carbon atom(s), unless otherwise indicated.

Suitable "lower alkylene" may include straight or branched one having 1 to 6 carbon atom(s), such as methylene, ethylene, trimethylene, propylene, tetramethylene, methylmethylene, methyltrimethylene, hexamethylene, and the like, in which the preferred one is methylene, ethylene, trimethylene or methylmethylene.

Suitable "halogen" and "halogen moiety" in the term "dihalobenzoyl(lower)alkyl" and "halophenyl" may include fluorine, chlorine, bromine and iodine.

Suitable "lower alkyl" and "lower alkyl moiety" in the terms "pyridyl(lower)alkylamino(lower)alkyl", "pyridyl(lower)alkylamino(lower)alkenyl", "N-(lower alkyl)-N-[pyridyl(lower)alkyl]amino(lower)alkyl", "triazolylamino(lower)alkyl", "lower alkoxy(lower)alkylamino(lower)alkyl", "bis[(lower)alkoxy(lower)alkyl]amino(lower)alkyl", "N-(lower alkyl)-N-[(lower)alkoxy(lower)alkyl]amino(lower)alkyl", "hydroxy(lower)alkyl", "lower alkylsulfonyloxy(lower)alkyl", "phenyl(lower)alkyl", "di(lower)alkylaminocarbonyl", "lower alkoxyphenyl(lower)alkylcarbonyl", "benzoyl(lower)alkyl", "di(lower)alkylamino", "benzoyl(lower)alkyl", "dihalobenzoyl(lower)alkyl", "di(lower)alkylbenzoyl(lower)alkyl", "3-fluorobenzoyl(lower)alkyl", "piperazinylcarbonyl(lower)alkyl", "(2-pyridyl)(lower)alkyl", "imidazolyl(lower)alkyl", "pyrazolyl(lower)alkyl", "thiomorpholinylcarbonyl(lower)alkyl", "(3-azabicyclo[3.2.2]non-3-yl)carbonyl(lower)alkyl", "thienylcarbonyl(lower)alkyl", "1,2,3,6-tetrahydropyridyl(lower)alkyl", "1,2,3,4-tetrahydroisoquinolyl(lower)alkyl", "4,5,6,7-tetrahydrothieno[3,2-c]pyridinyl(lower)alkyl", "saturated heterocyclic(lower)alkyl", "saturated heterocyclicamino(lower)alkyl" and "lower alkoxyphenyl(lower)alkyl" may include straight or branched one having 1 to 6 carbon atom(s), such as methyl, ethyl, propyl, isopropyl, butyl, isobutyl, pentyl, hexyl and the like, preferably one having 1 to 5 carbon atom(s).

Suitable "lower alkenyl moiety" in the terms "chloro(lower)alkenyl", "pyridyl(lower)alkkylamino(lower)alkenyl", "saturated heterocyclic(lower)alkenyl" and "saturated heterocyclicamino(lower)alkenyl" may include vinyl, 1-(or 2-)propenyl, 1-(or 2- or 3-)butenyl, 1-(or 2- or 3- or 4-)pentenyl, 1-(or 2- or 3- or 4- or 5-)hexenyl, methylvinyl, ethylvinyl, 1-(or 2- or 3-)methyl-1-(or 2-)propenyl, 1-(or 2- or 3-)ethyl-1-(or 2-)propenyl, 1-(or 2- or 3- or 4-)methyl-1-(or 2- or 3-)butenyl, and the like, in which more preferable example may be $C_2$–$C_4$ alkenyl.

Suitable "lower alkynyl moiety" in the terms "chloro(lower)alkynyl", "(3-pyridyl)(lower)alkynyl", "1,2,3,6-tetrahydropyridyl(lower)alkynyl", "saturated heterocyclic(lower)alkynyl" and "saturated heterocyclicamino(lower)alkynyl" may include ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl and the like, in which more preferable example may be $C_2$–$C_5$ alkynyl.

Suitable "aryl" may include phenyl, naphthyl, and the like, in which the preferred one is $C_6$–$C_{10}$ aryl and the most preferred one is phenyl.

Suitable "lower alkanoyl" and "lower alkanoyl moiety" in the terms "lower alkanoylamino", "lower alkanoylbenzoyl" and "lower alkanoylphenyl" may include formyl, acetyl, propanoyl, butanoyl, 2-methylpropanoyl, pentanoyl, 2,2-dimethylpropanoyl, hexanoyl and the like.

Suitable "lower alkoxy moiety" in the terms "lower alkoxyphenyl(lower)alkylcarbonyl" and "lower alkoxyphenyl(lower)alkyl" may include methoxy, ethoxy, propoxy, isopropoxy, butoxy, isobutoxy, t-butoxy, pentyloxy, t-pentyloxy, hexyloxy and the like.

Suitable "saturated heterocyclic" and "saturated heterocyclic moiety" in the terms "saturated heterocyclic(lower)alkyl", "saturated heterocyclic(lower)alkynyl", "saturated heterocyclicamino(lower)alkyl", "saturated heterocyclicamino(lower)alkenyl" and "saturated heterocyclicamino(lower)alkynyl" may include saturated 3 to 8-membered (more preferably 5 to 7-membered) heteromonocyclic group containing 1 to 4 nitrogen atom(s), for example, pyrrolidinyl, imidazolidinyl, piperidyl, piperazinyl, hexamethyleneimino, etc.;

saturated 3 to 8-membered (more preferably 5 to 6-membered) heteromonocyclic group containing 1 or 2 oxygen morpholinyl, sydnonyl, etc.;

saturated 3 to 8-membered (more preferably 5 or 6-membered) heteromonocyclic group containing 1 or 2 sulfur atom(s) and 1 to 3 nitrogen atom(s), for example, thiazolidinyl, thiomorpholinyl, etc.;

saturated heterobicyclic group of the formula:

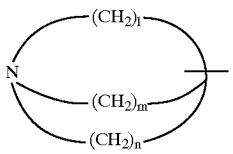

(wherein l, m and n are each integer of 1 to 6);
saturated heterobicyclic group of the formula:

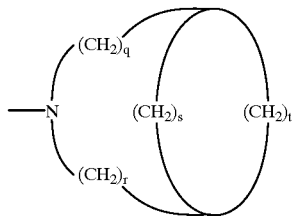

(wherein q, r, s and t are each integer of 1 to 6); and the like.

Suitable "substituent" in the terms "aryl which may have suitable substituent(s)", "aryl or indolyl each of which may have suitable substituent(s)", "thienylcarbonyl(lower)alkyl 1,2,3,6-tetrahydropyridyl(lower)alkyl, 1,2,3,6-tetrahydropyridyl(lower)alkynyl, 1,2,3,4-tetrahydroisoquinolyl(lower)alkyl, 4,5,6,7-tetrahydrothieno[3,2-c]pyridinyl(lower)alkyl, saturated heterocyclic(lower) alkyl, saturated heterocyclic(lower) alkenyl, saturated heterocyclic(lower)alkynyl, saturated heterocyclicamino (lower)alkyl, saturated heterocyclicamino(lower)alkenyl or saturated heterocyclicamino(lower)alkynyl, each of which may have suitable substituent(s)" and "1,2,3,4-tetrahydroisoquinolyl, 4,5,6,7-tetrahydrothieno[3,2-c] pyridinyl or saturated heterocyclic each of which may have suitable substituent(s)" may include lower alkyl (e.g., methyl, ethyl, propyl, isopropyl, butyl, isobutyl, tert-butyl, pentyl, neopentyl, tert-pentyl, hexyl, etc.), cyclo(lower)alkyl (e.g., cyclopropyl, cyclobutyl, cyclopentyl, cyclohexyl, etc.), lower alkoxy (e.g., methoxy, ethoxy, propoxy, isopropoxy, isobutoxy, tert-butoxy, pentyloxy, neopentyloxy, tert-pentyloxy, hexyloxy, etc.), lower alkoxy (lower)alkyl (e.g., methoxymethyl, ethoxymethyl, 1-methoxyethel, 2-methoxyethyl, 1-ethoxyethel, 2-ethoxyethel, etc.), lower alkanoyl (e.g., formyl, acetyl, propionyl, butyryl, isobutyryl, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, etc.), mono(or di or tri)halo(lower)alkyl (e.g., fluoromethyl, difluoromethyl, trifuloromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, etc.), halogen (e.g., chlorine, bromine, fluorine and iodine), carboxy, protected carboxy, hydroxy, protected hydroxy, aryl (e.g., phenyl, naphthyl, etc.), ar(lower)alkyl such as phenyl(lower)alkyl (e.g., benzyl, phenethyl, phenylpropyl, etc.), carboxy(lower)alkyl wherein lower alkyl moiety can be referred to the ones as exemplified above, protected carboxy(lower)alkyl wherein lower alkyl moiety can be referred to the ones as exemplified above, nitro, amino, protected amino, di(lower)alkylamino (e.g., dimethylamino, diethylamino, diisopropylamino, ethylmethylamino, isopropylmethylamino, ethylisopropylamino, etc.), hydroxy (lower)alkyl, protected hydroxy(lower)alkyl, acyl, cyano, oxo, mercapto, lower alkylthio (e.g., methylthio, ethylthio, propylthio, isopropylthio, butylthio, etc.), lower alkylsulfinyl (e.g., methylsulfinyl, ethylsulfinyl, propylsulfinyl, isopropylsulfinyl, butylsulfinyl, etc.), imino, morpholinyl, (e.g., 2-morpholinyl, 3-morpholinyl, morpholino), bivalent group of the formula:

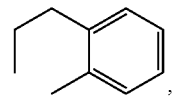

and the like.

Suitable "leaving group" may include lower alkoxy (e.g. methoxy, ethoxy, propoxy, isopropoxy, butoxy, isobutoxy, t-butoxy, pentoxy, etc.), aryloxy (e.g. phenoxy, naphthoxy, etc.), an acid residue or the like.

Suitable "acid residue" may be halogen (e.g. chlorine, bromine, iodine, etc.), sulfonyloxy (e.g. methylsulfonyloxy, phenylsulfonyloxy, mesitylenesultonyloxy, toluenesulfonyloxy, etc.) or the like.

Suitable "acyloxy" may include hydroxysulfonyloxy, lower alkylsulfonyloxy (e.g. methylsulfonyloxy, ethylsulfonyloxy, etc.), phosphonooxy, and the like.

Preferred embodiments of the object compound (I) are as follows:

Y is lower alkylene (more preferably $C_1$–$C_4$ alkylene, most preferably methylene);

$R^1$ is aryl (more preferably $C_6$–$C_{10}$ aryl, most preferably phenyl) which may have 1 to 3 (more preferably 1 or 2, most preferably 2) suitable substituent(s) [more preferably mono(or di or tri)halo(lower)alkyl (more preferably trihalo(lower)alkyl, most preferably trifluoromethyl)];

$R^2$ is aryl (more preferably $C_6$–$C_{10}$ aryl, most preferably phenyl or naphthyl) or indolyl each of which may have 1 to 3 (more preferably 1 or 2, most preferably 2) suitable substituent(s) [more preferably substituent selected from the group consisting of lower alkyl (more preferably $C_1$–$C_4$ alkyl, most preferably methyl), lower alkoxy (more preferably $C_1$–$C_4$ alkoxy, most preferably methoxy), mono(or di or tri)halo(lower)alkyl (more preferably mono(or di or tri)halo($C_1$–$C_4$)alkyl, most preferably trifluoromethyl) and halogen (more preferably chlorine or fluorine)];

$R^3$ is hydrogen; and $R^4$ is chloro(lower)alkenyl (more preferably chloro($C_2$–$C_4$)alkenyl, most preferably 4-chloro-2-butenyl); chloro(lower)alkynyl (more preferably chloro($C_2$–$C_4$) alkynyl, most preferably 4-chloro-2-butynyl; pyridyl (lower)alkylamino(lower)alkyl [more preferably pyridyl($C_1$–$C_4$)alkylamino($C_1$–$C_4$)alkyl, most preferably 2-[(3-pyridylmethyl)amino]ethyl, 2-[(4-pyridylmethyl)amino]ethyl or 3-[(3-pyridylmethyl)amino]propyl]; pyridyl(lower)alkylamino(lower) alkenyl (more preferably pyridyl($C_1$–$C_4$)alkylamino ($C_2$–$C_4$)alkenyl, most preferably 4-[(3-pyridylmethyl)amino]-2-butenyl); N-(lower alkyl)-N-[pyridyl(lower)alkyl]amino(lower)alkyl (more preferably N-($C_1$–$C_4$ alkyl)-N-[pyridyl($C_1$–$C_4$)alkyl]amino($C_1$–$C_4$)alkyl, more preferably 2-[N-methyl-N-(3-pyridylmethyl)amino]ethyl]; triazolylamino(lower)alkyl (more preferably triazolylamino($C_1$–$C_4$)alkyl, most preferably 3-(1,2,4-triazol-3-ylamino) propyl); lower alkoxy(lower) alkylamino(lower)alkyl (more preferably $C_1$–$C_4$ alkoxy($C_1$–$C_4$)alkylamino($C_1$–$C_4$)alkyl, most preferably 2-(2-methoxyethyl)aminoethyl); bis[(lower)alkoxy(lower)alkyl]amino(lower)alkyl [more preferably bis[($C_1$–$C_4$)alkoxy($C_1$–$C_4$)alkyl]amino($C_1$–$C_4$) alkyl, alkyl, most preferably 3-[bis(2-methoxyethyl)amino]propyl]; N-(lower alkyl)-N-[(lower)alkoxy (lower)alkyl]amino(lower) alkyl [more preferably N-($C_1$–$C_4$ alkyl)-N-[($C_1$–$C_4$)alkoxy($C_1$–$C_4$)alkyl]amino($C_1$–$C_4$)alkyl, most preferably 2-[N-methyl-N-(2-methoxyethyl)amino]ethyl]; hydroxy(lower)alkyl (more preferably hydroxy($C_1$–$C_4$) alkyl, most preferably hydroxypropyl); lower alkylsulfonyloxy(lower)alkyl (more preferably $C_1$–$C_4$ alkylsulfonyloxy($C_1$–$C_4$) alkyl, most preferably methylsulfonyloxypropyl); phenyl(lower)alkyl (more preferably phenyl($C_1$–$C_4$) alkyl, most preferably benzyl) which may have lower alkanoyl (more preferably $C_1$–$C_4$ alkanoyl, most preferably acetyl), amino, lower alkanoylamino (more preferably $C_1$–$C_4$ alkanoylamino, most preferably acetylamino), di(lower)alkylaminocarbonyl (more preferably di($C_1$–$C_4$)alkylaminocarbonyl, most preferably diethylaminocarbonyl) or nitro; lower alkoxyphenyl(lower)alkylcarbonyl (more preferably $C_1$–$C_4$ alkoxyphenyl($C_1$–$C_4$)alkylcarbonyl, most preferably methoxyphenylmethylcarbonyl); lower alkanoylbenzoyl (more preferably $C_1$–$C_4$ alkanoylbenzoyl, most preferably acetylbenzoyl); benzoyl(lower)alkyl (more preferably benzoyl($C_1$–$C_4$) alkyl, most preferably benzoylmethyl) which has lower alkyl (more preferably $C_1$–$C_4$ alkyl, most preferably methyl), chlorine or di(lower)alkylamino (more preferably di($C_1$–$C_4$)alkylamino, most preferably dimethylamino); benzoyl(lower)alkyl (more preferably benzoyl($C_1$–$C_4$)alkyl, most preferably benzoylmethyl) which has halogen (more preferably fluorine) and lower alkyl (more preferably $C_1$–$C_4$ alkyl, most preferably methyl); dihalobenzoyl(lower)alkyl [more preferably dihalobenzoyl($C_1$–$C_4$)alkyl, most preferably (difluorobenzoyl)methyl]; di(lower)alkylbenzoyl (lower)alkyl [more preferably di($C_1$–$C_4$)alkylbenzoyl ($C_1$–$C_4$)alkyl, most preferably dimmethylbenzoylmethyl]; 3-fluorobenzoyl(lower) alkyl (more preferably 3-fluorobenzoyl ($C_1$–$C_4$)alkyl, most preferably 3-fluorobenzoylmethyl); 3-(4-fluorobenzoyl)propyl; 4,4-ethylenedioxy-4-(4-fluorophenyl)butyl; piperazinylcarbonyl(lower)alkyl (more preferably piperazinylcarbonyl($C_1$–$C_4$)alkyl, most preferably piperazinylcarbonylmethyl) which has cyclopentyl or halophenyl (more preferably fluorophenyl); (2-pyridyl)(lower)alkyl (more preferably (2-pyridyl) ($C_1$–$C_4$)alkyl, most preferably (2-pyridyl)methyl); (3-pyridyl)propyl (more preferably 3-(3-pyridyl)propyl); (3-pyridyl)(lower)alkynyl (more preferably 3-pyridyl) ($C_2$–$C_4$)alkynyl, most preferably 3-(3-pyridyl)-2-propynyl); imidazolyl(lower)alkyl (more preferably imidazolyl($C_1$–$C_4$) alkyl, most preferably (1H-imidazol-1-yl)methyl, (1H-imidazol-2-yl)methyl or (1H-imidazol-4-yl)methyl) which may have lower alkyl (more preferably $C_1$–$C_4$ alkyl, most preferably methyl); pyrazolyl(lower)alkyl (more preferably pyrazolyl($C_1$–$C_4$)alkyl, most preferably (1H-pyrazol-4-yl)methyl or 3-(1H-pyrazol-4-yl) propyl) which may have lower alkyl (more preferably $C_1$–$C_4$ alkyl, most preferably methyl); thiomorpholinylcarbonyl(lower) alkyl (more preferably thiomorpholinylcarbonyl ($C_1$–$C_4$)alkyl, most preferably thiomorpholinylcarbonylmethyl); (3-azabicyclo[3.2.2]non-3-yl)carbonyl(lower)alkyl (more preferably (3-azabicyclo[3.2.2]non-3-yl)carbonyl($C_1$–$C_4$) alkyl, most preferably (3-azabicyclo[3.2.2]non-3-yl) carbonylmethyl); or thienylcarbonyl(lower)alkyl (more preferably thienylcarbonyl($C_1$–$C_4$)alkyl, most preferably thienylcarbonylmethyl, 1,2,3,6-tetrahydropyridyl (lower) alkyl (more preferably 1,2,3,6-tetrahydropyridyl($C_1$–$C_4$) alkyl, most preferably 3-(1,2,3,6-tetrahydropyridin-1-yl) propyl), 1,2,3,6-tetrahydropyridyl(lower)alkynyl (more preferably 1,2,3,6-tetrahydropyridyl($C_2$–$C_4$)alkynyl, most preferably 4-(1,2,3,6-tetrahydropyridin-1-yl)-2-butynyl), 1,2,3,4-tetrahydroisoquinolyl(lower)alkyl (more preferably 1,2,3,4-tetrahydroisoquinolyl($C_1$–$C_4$)alkyl, most preferably 1,2,3,4-tetrahydroisoquinolylpropyl, 4,5,6,7-tetrahydrothieno[3,2-c]pyridinyl(lower)alkyl (more preferably 4,5,6,7-tetrahydrothieno[3,2-c]pyridinyl ($C_1$–$C_4$)alkyl, most preferably 4,5,6,7-tetrahydrothieno [3,2-c]pyridinylpropyl), saturated heterocyclic(lower)alkyl (more preferably saturated heterocyclic($C_1$–$C_4$) alkyl, more preferably saturated heterocyclicethyl or saturated heterocyclicpropyl, most preferably saturated heterocyclicpropyl), saturated heterocyclic(lower) alkenyl (more preferably saturated heterocyclic ($C_2$–$C_4$)alkenyl, most preferably saturated heterocyclicbutenyl), saturated heterocyclic(lower)alkynyl (more preferably saturated heterocyclic ($C_2$–$C_5$)alkynyl, most preferably saturated heterocyclicbutynyl or saturated heterocyclicpentynyl), saturated heterocyclicamino(lower)alkyl (more preferably saturated heterocyclicamino($C_1$–$C_4$)alkyl, most preferably saturated heterocyclicaminopropyl), saturated heterocyclicamino(lower)alkenyl (more preferably saturated heterocyclicamino($C_2$–$C_4$)alkenyl, most preferably saturated heterocyclicaminobutenyl) or saturated heterocyclicamino(lower)alkynyl (more preferably saturated heterocyclicamino($C_2$–$C_5$)alkynyl, most preferably saturated heterocyclicaminobutynyl) [wherein "saturated heterocyclic moiety" is saturated 3 to 8-membered (more preferably 5 to 7-membered) heteromonocyclic group containing 1 to 4 (more preferably 1 or 2) nitrogen atom(s) (more preferably pyrrolidinyl, piperidyl, piperazinyl or hexamethyleneimino, most preferably piperidyl); saturated 3 to 8-membered (more preferably 5 to 7-membered) heteromonocyclic group containing 1 or 2 (more preferably 1) oxygen atom(s) and 1 to 3 (more preferably 1) nitrogen atom(s) (more preferably morpholinyl or homomorpholinyl, most preferably morpholinyl); saturated 3 to 8-membered (more preferably 5 or 6-membered) heteromonocyclic group containing 1 or 2 (more preferably 1) sulfur atom(s) and 1 to 3 (more preferably 1) nitrogen atom(s) (more preferably thiomorpholinyl); or saturated heterocyclic group of the formula:

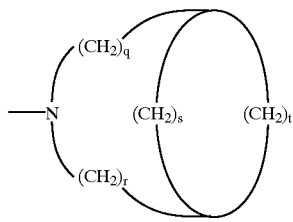

(more preferably 3-azabicyclo[3.2.2]non-3-yl)], each of which may have 1 to 3 (more preferably 1 or 2) suitable substituent(s) [more preferably substituent selected from the group consisting of cyclo(lower)alkyl (more preferably cyclohexyl), lower alkanoyl (more preferably $C_1$–$C_4$ alkanoyl, most preferably acetyl), lower alkyl (more preferably $C_1$–$C_4$ alkyl, most preferably methyl), mono (or di or tri)halo(lower)alkyl (more preferably monohalo($C_1$–$C_4$) alkyl, most preferably fluoromethyl), lower alkoxy (more preferably $C_1$–$C_4$ alkoxy, most preferably methoxy), lower alkoxy(lower)alkyl (more preferably $C_1$–$C_4$ alkoxy($C_1$–$C_4$) alkyl, most preferably methoxymethyl), halogen (more preferably chlorine), aryl (more preferably phenyl), cyano, oxo and bivalent group of the formula:

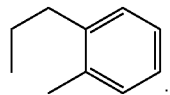

More preferred embodiments of the object compound (I) are as follows:

Y is lower alkylene (more preferably $C_1$–$C_4$ alkylene, most preferably methylene);

$R^1$ is phenyl which may have 1 or 2 mono (or di or tri) halo(lower)alkyl [more preferably bis(trihalo(lower)alkyl) phenyl, most preferably bis(trifluoromethyl)phenyl];

$R^2$ is phenyl which may have 1 or 2 suitable substituent(s) selected from the group consisting of lower alkyl, lower alkoxy, mono (or di or tri)halo(lower)alkyl and halogen [more preferably di(lower)alkylphenyl, (lower) alkoxyphenyl, [trihalo(lower)alkyl]phenyl, [(lower)alkyl] halophenyl, halophenyl or dihalophenyl, most preferably dimethylphenyl, methoxyphenyl, (trifluoromethyl)phenyl, methylfluorophenyl, fluorophenyl or difluorochlorophenyl], naphthyl or indolyl;

$R^3$ is hydrogen; and $R^4$ is morpholinyl(lower)alkyl which may have 1 or 2 lower alkyl (more preferably methyl), homomorpholinyl (lower)alkyl, thiomorpholinyl(lower)alkyl, (hexamethyleneimino)(lower)alkyl, (3-azabicyclo[3.2.2] non-3-yl)(lower)alkyl, piperazinyl(lower)alkyl which may have phenyl or cyclo(lower)alkyl (more preferably piperazinyl(lower)alkyl which has phenyl or cyclohexyl), morpholinyl(lower)alkenyl which may have 1 or 2 lower alkyl (more preferably methyl), morpholinyl(lower)alkynyl which may have a substituent selected from the group consisting of lower alkyl (more preferably methyl), lower alkoxy(lower)alkyl (more preferably methoxymethyl) and mono(or di or tri)halo(lower)alkyl (more preferably fluoromethyl), thiomorpholinyl(lower)alkenyl, thiomorpholinyl(lower)alkynyl, pyrrolidinyl(lower)alkynyl which may have lower alkoxy(lower)alkyl (more preferably methoxymethyl), piperazinyl(lower)alkynyl which may have cyclo(lower)alkyl (more preferably cyclohexyl), morpholinylamino(lower)alkyl, morpholinylamino(lower) alkenyl, morpholinylamino(lower)alkynyl, or piperidyl (lower)alkyl which may have 1 or 2 suitable substituent(s) selected from the group consisting of bivalent group of the formula:

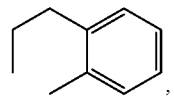

phenyl, cyano, lower alkanoyl, lower alkoxy, piperidinyl, and oxo [more preferably [spiro[indan-1,4'-piperidine]-1'-yl](lower)alkyl, piperidyl(lower)alkyl which has phenyl, acetyl, methoxy, piperidino or oxo, or piperidyl(lower)alkyl which has phenyl and cyano].

The Processes 1 to 7 for preparing the object compound (I) of the present invention are explained in detail in the following.

Process 1

The object compound (I) or a salt thereof can be prepared by reacting the compound (II) or its reactive derivative at the imino group or a salt thereof with the compound (IV) or a salt thereof.

Suitable reactive derivative at the imino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, mono(trimethylsilyl) acetamide, bis(trimethylsilyl)urea or the like; a derivative formed by reactive of the compound (II) with phosphorus trichloride or phosgene and the like.

The reaction is usually carried out in a conventional solvent such as water, alcohol [e.g. methanol, ethanol, etc.], acetone, dioxene, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

The reaction may also be carried out in the presence of an inorganic or organic base such as alkali metal carbonate, alkali metal bicarbonate, tri(lower)alkylamine, pyridine, N-(lower)alkylmorpholine, N,N-di(lower) alkylbenzylamine, or the like.

The reaction temperature is not critical, and the reaction is usually carried out under cooling to heating.

Process 2

The object compound (Ia) or a salt thereof can be prepared by reacting the compound (V) or its reactive derivative at the carboxy group or a salt thereof with the compound (II) or its reactive derivative at the imino group or a salt thereof.

Suitable reactive derivative at the carboxy group of the compound (V) may include an acid halide, an acid anhydride, an activated amide, an activated ester, and the like. The suitable example of the reactive derivative may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, lower alkanesulfonic acid [e.g. methanesulfonic acid, ethanesulfonic acid, etc.], sulfurous acid, thiosulfuric acid, sulfuric acid, aliphatic carboxylic acid [e.g. acetic acid, propionic acid, butyric acid, isobutyric acid pivalic acid, valeric acid, isovaleric acid, 2-ethylbutyric acid, trichloroacetic acid, etc.] or aromatic carboxylic acid [e.g. benzoic acid, etc.]; a symmetrical and anhydride; an activated amide with imidazole, 4-substituted imidazole, dimethylpyrazole, triazole or tetrazole; or an activated ester [eg. cyanomethyl ester, methoxymethyl ester, dimethyliminomethyl [$(CH_3)_2N^+=CH—$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (V) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

In this reaction, when the compound (V) is used in a free acid form or a salt thereof, the reaction is preferably carried out in the presence of a conventional condensing agent such as N,N'-dichlrohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phsophorylazide; thienyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; 2-chloro-1-methylpyridinium iodide; 1-(3-dimethylaminopropyl)-3-ethylcarbodiimide hydrochloride; so-called vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as alkali metal carbonate, alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Process 3

The object compound (Ib) or a salt thereof can be prepared by reacting the compound (III) or its reactive derivative at the carboxy group or a salt thereof with the compound (VI) or a salt thereof.

The reaction mode and reaction conditions of this reaction are to be referred to those as explained in Process 2.

Process 4

The object compound (Id) or a salt thereof can be prepared by subjecting the compound (Ic) or a salt thereof to an acylation reaction.

The reaction can be carried out in the manner disclosed in Example 20 mentioned later or similar manners thereto.

Process 5

The compound (Ie) or a salt thereof can be prepared by reacting the compound (Id) or a salt thereof with the compound (VII) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, acetonitrile, diethyl ether or any other solvents which do not adversely affect the reaction, or the mixture thereof.

The reaction temperature is not critical and the reaction is usually carried out under cooling to heating.

The reaction may be also carried out in the presence of an inorganic or an organic base such as alkali metal (e.g., sodium, potassium, etc.), alkali metal hydroxide (e.g., sodium hydroxide, potassium hydroxide, etc.), alkali metal hydrogencarbonate (e.g., sodium hydrogencarbonate, potassium hydrogencarbonate, etc.), alkali metal carbonate (e.g., sodium carbonate, potassium carbonate, etc.), tri(lower) alkylamine (e.g., trimethylamine, triethylamine, diisopropylethylamine, etc.), alkali metal hydride (e.g., sodium hydride, etc.), alkali metal (lower)alkoxide (e.g. sodium methoxide, sodium ethoxide, etc.), pyridine, lutidine, picoline, dimethylaminopyridine, N-(lower) alkylmorpholine, N,N-di(lower)alkylbenzylamine, N,N-di (lower)alkylaniline or the like.

When the base and/or the starting compound are in liquid, they can be used also as a solvent.

Process 6

The object compound (Ig) or a salt thereof can be prepared by subjecting the compound (If) or a salt thereof to a reduction reaction.

The reaction can be carried out in the manner disclosed in Example 29 mentioned later or similar manners thereto.

Process 7

The object compound (Ih) or a salt thereof can be prepared by subjecting the compound (Ig) or a salt thereof to acylation reaction.

The reaction can be carried out in the manner disclosed in Example 31 mentioned later or similar manners thereto.

The object compound (I) and a pharmaceutically acceptable salt thereof have pharmacological activities such as Tachykinin antagonism, especially Substance P antagonism, Neurokinin A antagonism or Neurokinin 5 antagonism, and therefore are useful for treating or preventing Tachykinin-mediated diseases, particularly Substance P-mediated diseases, for example, respiratory diseases such as asthma, bronchitis (e.g. chronic bronchitis, acute bronchitis and diffuse panbronchiolitis, etc.), rhinitis, cough, expectoration, and the like; ophthalmic diseases such as conjuctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g. migraine, headache, cluster headache, toothache, cancerous pain, back pain, neuralgia, etc.); and the like.

Further, it is expected that the object compound (I) and a pharmaceutically accepted salt thereof of the present invention are useful for treating or preventing ophthalmic diseases such as glaucoma, uveitis, and the like; gastrointestinal diseases such as ulcer, ulcerative colitis, irritable bowel syndrome, food allergy, and the like; inflammatory diseases such as nephritis, and the like; circulatory diseases such as hypertension, angina pectoris, cardiac failure, thrombosis, Raynaud's disease, and the like; epilepsy; spastic paralysis; pollakiuria; cystitis; bladder detrusor hyperreflexia; urinary incontinence; Parkinson diseases; dementia; AIDS related dementia; Alzheimer's diseases; Down's syndrome; Huntington's chorea; carcinoid syndrome; disorders related to immune enhancement or suppression; disorder caused by Helicobacter pylori or another spiral urease-positive gram-negative bacterium; sunburn; angiogenesis or diseases caused by angiogenesis; and the like.

It is furthermore expected that the object compound (I) and a pharmaceutically acceptable salt thereof of the present invention are useful for treating or preventing chronic obstructive pulmonary diseases, particularly chronic pulmonary emphysema; iritis; profilerative vitreoretinopathy; psoriasis; inflammatory intestinal diseases, particularly Crohn's diseases; hepatitis; superficial pain on congelation, burn, herpes zoster or diabetic neuropathy; tenalgia attended to hyperlipidemia, postoperative neuroma, particularly of mastectomy; vulvar vestibulitis; hemodialysis-associated itching; lichen planus; laryngopharyngitis; bronchiectasis; coniosis; whooping cough; pulmonary tuberculosis; cystic fibrosis; emesis; mental diseases, particularly anxiety, depression, dysthymic disorders and schizophrenia; demyelinating diseases such as multiple sclerosis and amyotrophic lateral sclerosis; attenuation of morphine withdrawal; oedema, such as oedema caused by thermal injury; small cell carcinomas, particularly small cell lung cancer (SCLC); hypersensitivity disorders such as poison ivy; fibrosing and collagen diseases such as scleroderma and eosinophilic fascioliasis; reflex sympathetic dystrophy such as shoulder/hand syndrome; addiction disorders such as alcoholism; stress related somatic disorders; rheumatic diseases such as fibrositis; and the like.

Furthermore, the object compound (I) and a pharmaceutically acceptable salt thereof of the present invention are Central Nervous System (CNS) penetrant.

For therapeutic purpose, the compound (I) and a pharmaceutically acceptable salt thereof of the present invention can be used in a form of pharmaceutical preparation containing one of said compound, as an active ingredient, in admixture with a pharmaceutically acceptable carrier such as an organic or inorganic solid or liquid excipient suitable for oral, parenteral, external including topical, enternal, intravenous, intramuscular, inhalant, nasal, intraarticular, intraspinal, transtracheal or transocular administration. The pharmaceutical preparations may be solid, semi-solid or solutions such as capsules, tablets, pellets, dragees, powders, granules, suppositories, ointments, creams, lotions, inhalants, injections, cataplasms, gels, tapes, eye drops, solution, syrups, aerosols, suspension, emulsion, or the like. If desired, there may be included in these preparations, auxiliary substances, stabilizing agents, wetting or emulsifying agents, buffers and other commonly used additives.

While the dosage of the compound (I) will vary depending upon the age and condition of a patient, an average single dose of about 0.1 mg, 1 mg, 10 mg, 50 mg, 100 mg, 250 mg, 500 mg, and 1000 mg of the compound (I) may be effective for treating Tachykinin-mediated diseases such as asthma and the like. In general, amounts between 0.1 mg/body and about 1,000 mg/body may be administered per day.

In order to show the utility of the object compound (I) and a pharmaceutically acceptable salt thereof, the pharmacological test data of some representative compounds of the present invention is shown in the following.

A. Evaluation of $NK_1$ antagonist transport efficiency to the central nervous system using a h-$NK_1$ receptor binding assay

[I] Test Method (1) Administration of test compound and extraction of the compound from brain Male SD rats were given an i.v. injection of a solution containing a test compound (1 mg/kg). 5 Min later the animals were anesthetized by ether, bled and perfused through the aorta ascendens with 20 ml of saline. The brain was rapidly removed, weighed and homogenized in 4 vol. ice-cold distilled water by using Polytoron (KINEMATICA). To extract the test compound, 500 µl of the homogenate, 100 µl of methanol, 500 µl of 0.1 N NaOH and 4 ml of ethyl acetate were mixed by shaking for 10 min at room temperature. The organic phase (2.5 ml) was recovered by centrifugation at 3,000 rpm for 10 min, dried and dissolved in dimethyl sulfoxide.

(2) h-$NK_1$ receptor binding assay (a) Crude CHO cell membrane preparation

CHO cells permanently expressing h-$NK_1$ receptors were harvested and homogenized with a Dounce homogenizer at 4° C. in a buffer (0.25 M sucrose, 25 mM Tris-HCl (pH 7.4), 10 mM $MgCl_2$, 1 mM EDTA, 5 µg/ml p-APMSF). The homogenate was centrifuged (500×g, 10 min), and the pellet was resuspended in the same buffer, homogenized, and centrifuged. The two supernatants were combined and centrifuged (100,000×g, 1 hour). The crude cell membranes thus isolated were resuspended in a buffer (25 mM Tris-HCl (pH 7.4), 10 mM $MgCl_2$, 1 mM EDTA, 5 µg/ml p-APMSF) and stored at −80° C. until use.

(b) $^{125}$I-BH-Substance P binding to the prepared membrane

Cell membranes (6 µg/ml) were incubated with $^{125}$I-BH-Substance P (0.1 nM) with or without the extracted compounds in 0.25 ml of a medium (50 mM Tris-HCl (pH 7.4), 5 mM $MnCl_2$, 20 µg/ml chymostatin, 40 µg/ml bactracin, 4 µg/ml leupeptin, 5 µg/ml p-APMSF, 200 µg/ml BSA) at 22° C. for 90 min. At the end of the incubation period, the contents were quickly filtered through a Blue Mat 11740 filter (pretreated with 0.1% polyethylenimine for 3 hours prior to use) by using SKATRON Cell Harvester. The filter was then washed with a washing buffer (50 mM Tris-HCl (pH 7.4), 5 mM $MnCl_2$). The radioactivity was counted by using an auto gamma counter (Packard RIASTAR 5420A). All data presented are specific binding defined as that displaceable by 3 µM unlabeled Substance P.

[II] Test Result

All of the following Test Compounds showed more than 80% inhibition rate of $^{125}$I-BH-Substance P binding to h-$NK_1$ receptors at the dose of 1 mg/kg.

Test Compounds: The object compounds of the Examples 7, 11, 12, 22, 23, 24-(2), 26, 35, 36, 37-(2), (4), (5), (6), (8), 44-(1), (2), (4), (5), (7), 46, 47, 51, 52-(1), 53-(1), 54, 55, 58, 59-(1), (3), 62-(1), 67-(4), (5), (6), (7), (13), 71, 72, 73, 74, 75, 76, 77, 81, 82-(1), 82-(4), 82-(5), 82-(7), 82-(8), 82-(9), 82-(10), 82-(12), 84-(1) and 86

B. Emesis in the ferret

[I] Test Method

Individually housed adult male ferrets (Marshall Farms, 1.4 to 2.2 kg) were given an i.p. injection of a solution containing a test compound. 30 Min later the emetic responses (retching and vomiting) were induced by administration of intra-gastric copper sulfate (40 mg/kg/ml) and observed for the next 30 min. The timing and number of retches and vomits observed were recorded for each animal. An individual animal was tested with at least 10 days between experiments.

[II] Test Result

All of the following Test Compounds showed 100% inhibition rate of emesis in the ferret at the dose of 3.2 and/or 10 mg/kg.

Test compounds: The object compounds of the Examples 12, 22, 23, 24-(2) and 37-(5), (6)

The following Preparations and Examples are given for the purpose of illustrating this invention.

EXAMPLE 1

A mixture of (2R)-1-[3,5-bis(trifluoromethyl)benzoyl]-2-(1H-indol-3-ylmethyl)piperazine (5 g) and 3-bromopropanol (1.68 g) in N,N-dimethylformamide (40 ml) was heated at 60° C. in the presence of potassium carbonate (4.55 g). After 9 hours, the reaction mixture was poured into water (400 ml) and extracted with ethyl acetate. The extract was washed with brine and dried over magnesium sulfate. After evaporation of the solvent, the obtained residue was purified by column chromatography on silica gel using dichloromethanemethanol (30:1) as an eluent to give (2R)-1-[3,5-bis(trifluoromethyl)benzoyl]-4-(3-hydroxypropyl)-2-(1H-indol-3-ylmethyl)piperazine (4.36 g) as a powder.

IR (Neat): 3600–3100, 1625, 1275, 1170, 1128, 898 cm$^{-1}$

NMR (DMSO-d$_6$, δ): 1.6–5.0 (16H, m); 6.6–8.2 (8H, m); 10.84 (1H, s)

MASS: 514 (M+1), 454

EXAMPLE 2

The following compound was obtained according to a similar manner to that of Example 1.

(2R)-1-[3,5-Bis(trifluoromethyl)benzoyl]-2-(3,4-dimethylbenzyl)-4-(3-hydroxypropyl)piperazine IR (Nujol): 3400 (br), 3000–2700, 1625, 1430, 1270, 1120 cm$^{-1}$ NMR (DMSO-d$_6$, δ): 1.55–1.75 (2H, m); 2.05–4.9 (19H, m); 6.5–8.2 (6H, m)

MASS: 503 (M+1)

EXAMPLE 3

A mixture of (2R)-1-[3,5-bis(trifluoromethyl)benzoyl]-2-(1H-indol-3-ylmethyl)piperazine (0.3 g), 2-bromo-4'-chloroacetophenone (0.2 g) and potassium carbonate (0.16 g) in N,N-dimethylformamide (5 ml) was stirred at room temperature for 1 hour and 20 minutes. The reaction mixture was poured into water (20 ml) and extracted with ethyl acetate. The organic layer was washed with water and dried over magnesium sulfate. After evaporation of the solvent, the obtained residue was purified by column chromatography on silica gel using toluene-ethyl acetate (4:1) as an eluent. Fractions containing objective compound were collected and concentrated under reduced pressure. The obtained product was dissolved in ethyl acetate, treated with 4N hydrogen chloride in ethyl acetate solution and then evaporated under reduced pressure. The residue was triturated with n-hexane to give (2)-1-[3,5-bis(trifluoromethyl)benzoyl]-4-(4-chlorophenylcarbonylmethyl)-2-(1H-indol-3-ylmethyl)piperazine hydrochloride (0.31 g) as a powder.

mp: 140° C. (dec.)

$[α]_D^{20}$: −22.6° (C=0.5, MeOH)

IR (Nujol): 3500–3100, 2700–2150, 1690, 1635, 1275, 1100 cm$^{-1}$

NMR (DMSO-d$_6$, δ): 2.9–5.3 (11H, m); 6.4–8.3 (12H, m); 10.7–11.05 (2H, m)

MASS: 608 (M+1) (free)

EXAMPLE 4

The following compound was obtained according to a similar manner to that of Example 3.

(2)-1-[3,5-Bis(trifluoromethyl)benzoyl]-4-[(5-chloro-2-thienyl)carbonylmethyl]-2-(1H-indol-3-ylmethyl)piperazine hydrochloride $[α]_D^{20}$: −55.2° (C=0.5, MeOH)

IR (Neat): 3700–3100, 2700–2150, 1635, 1415, 1275, 1130 cm$^{-1}$

NMR (DMSO-d$_6$, δ): 3.0–5.2 (11H, m); 6.8–8.3 (10H, m); 10.97 (1H, s)

MASS: 651 (M+1) (free), 614

EXAMPLE 5

A mixture of (2R)-1-[3,5-bis(trifluoromethyl)benzoyl]-2-(1H-indol-3-ylmethyl)piperazine (0.3 g), 2-bromo-3'-fluoroacetophenone (0.19 g) and potassium carbonate (0.16 g) in N,N-dimethylformamide (5 ml) was stirred at room temperature for 1 hour and 20 minutes. The reaction mixture was poured into water (20 ml) and extracted with ethyl acetate. The organic layer was washed with water and dried over magnesium sulfate. After evaporation of the solvent, the resulting residue was purified by column chromatography on silica gel using toluene-ethyl acetate (2:1) as an eluent. The obtained product was dissolved in ethyl acetate (2 ml) and treated with 4N hydrogen chloride in ethyl acetate solution (164 μl). The resulting precipitate was collected by filtration and dried at 50° C. for 5 hours to give (2R)-1-[3,5-bis(trifluoromethyl)benzoyl]-4-(3-fluorophenylcarbonylmethyl)-2-(1H-indol-3-ylmethyl) piperazine hydrochloride (0.2 g) as a powder.

mp: 195° C. (dec.)

$[α]_D^{20}$: −34.2° (C=0.5, MeOH)

IR (Nujol): 3200, 2650–2200, 1695, 1655, 1270, 1125 cm$^{-1}$

NMR (DMSO-d$_6$, δ): 3.3–5.3 (11H, m); 6.6–8.3 (12H, m); 10.8–11.4 (2H, m)

MASS: 592 (M+1) (free)

Anal. Calcd. for $C_{30}H_{24}F_7N_3O_2HCl$: C 57.38; H 4.01; N 6.69 Found: C 57.23; H 3.79; N 6.49

EXAMPLE 6

The following compounds were obtained according to a similar manner to that of Example 5.

(1) (2R)-1-[3,5-Bis(trifluoromethyl)benzoyl]-4-(3,4-difluorophenylcarbonylmethyl)-2-(1H-indol-3-ylmethyl)piperazine hydrochloride mp: 171° C. (dec.)

$[α]_D^{20}$: −31.6° (C=0.5, MeOH)

IR (Nujol): 3550–3100, 2650–2150, 1690, 1640, 1510, 1275, 1130 cm$^{-1}$

NMR (DMSO-d$_6$, δ): 3.0–5.3 (11H, m); 7.6–8.3 (11H, m); 10.7–11.5 (2H, m)

MASS: 610 (M+1) (free)

Anal. Calcd. for $C_{30}H_{23}F_8N_3O_2HCl$: C 55.78; H 3.74; N 6.50 Found: C 55.54; H 3.72; N 6.41

(2) (2R)-1-[3,5-Bis(trifluoromethyl)benzoyl]-2-(1H-indol-3-ylmethyl)-4-(4-methylphenylcarbonylmethyl)piperazine hydrochloride mp: 203° C. (dec.)

$[\alpha]_D^{20}$: −37.4° (C=0.5, MeOH)

IR (Nujol): 3550–3100, 2650–2150, 1690, 1640, 1280, 1175, 1125 cm$^{-1}$

NMR (DMSO-d$_6$, δ): 2.43 (3H, s);3.1–5.3 (11H, m); 6.8–8.3 (12H, m); 10.8–11.2 (2H, m)

MASS: 587 (M+1) (free)

(3) (2R)-1-[3,5-Bis(trifluoromethyl)benzoyl]-4-(3,4-dimethylphenylcarbonylmethyl)-2-(1H-indol-3-ylmethyl)piperazine hydrochloride mp: 166° C. (dec.)

$[\alpha]_D^{25}$: −36.8° (C=0.5, MeOH)

IR (Nujol): 3600–3150, 2700–2300, 1685, 1635, 1275, 1130 cm$^{-1}$

NMR (DMSO-d$_6$, δ): 2.34 (6H, s); 3.2–5.3 (11H, m); 6.6–8.3 (11H, m); 10.6–11.2 (2H, m)

MASS: 601 (M+1) (free)

Anal. Calcd. for $C_{32}H_{29}F_6N_3O_2 \cdot HCl \cdot 1.1H_2O$: C 58.42; H 4.93; N 6.39 Found: C 58.46; H 4.90; N 6.27

(4) (2R)-1-[3,5-Bis(trifluoromethyl)benzoyl]-4-(4-fluoro-3-methylphenylcarbonylmethyl)-2-(1H-indol-3-ylmethyl)piperazine hydrochloride $[\alpha]_D^{20}$: −28.8° (C=0.5, MeOH)

IR (Nujol): 3600–3100, 2700–2200, 1685, 1635, 1275, 1130 cm$^{-1}$

NMR (DMSO-d$_6$, δ): 2.34 (3H, s); 3.1–5.3 (11H, m); 6.6–8.3 (11H, m); 10.7–11.2 (2H, m)

MASS: 606 (M+1) (free)

EXAMPLE 7

A mixture of (2R)-1-[3,5-bis(trifluoromethyl)benzoyl]-2-(1H-indol-3-ylmethyl)piperazine (228 mg), 1-[4-(bromomethyl)phenyl]ethanone (107 mg) and potassium carbonate (42 mg) in acetonitrile (2 ml) was refluxed for 4.5 hours. After cooling, the mixture was evaporated in vacuo. Ethyl acetate and water were added to the residue and the organic layer was separated, washed with brine, dried over magnesium sulfate, and evaporated in vacuo. The residue was purified by column chromatography on silica gel with a mixture of dichloromethane and methanol as an eluent to give (2R)-4-(4-acetylbenzyl)-1-[3,5-bis(trifluoromethyl)benzoyl]-2-(1H-indol-3-ylmethyl)piperazine (0.30 g). To a solution of this piperazine (0.30 g) in ethyl acetate was added 4N hydrogen chloride in ethyl acetate solution (0.13 ml) and the whole was evaporated in vacuo. The residue was triturated with a mixture of ethyl acetate and ether to give (2R)-4-(4-acetylbenzyl)-1-[3,5-bis(trifluoromethyl)benzoyl]-2-(1H-indol-3-ylmethyl)piperazine hydrochloride (283.5 mg) as a powder.

mp: 172° C. (dec.)

$[\alpha]_D^{28}$: −30.0° (C=0.27, MeOH)

IR (Nujol): 3350, 1675, 1655, 1635, 1610, 1275 cm$^{-1}$

NMR (CDCl$_3$, δ): 2.36–5.60 (11H, m); 6.10–9.30 (13H, m); 12.90 (1H, br s)

MASS: 588 (M) (free)

EXAMPLE 8

A mixture of (2R)-1-[3,5-bis(trifluoromethyl)benzoyl]-2-(1H-indol-3-ylmethyl)piperazine (0.3 g), 2-bromo-4'-dimethylaminoacetophenone (0.2 g) and potassium carbonate (0.16 g) in N,N-dimethylformamide (5 ml) was stirred at room temperature for 2 hours. The reaction mixture was poured into water (20 ml) and extracted with ethyl acetate. The organic layer was washed with water and dried over magnesium sulfate. After evaporation of the solvent, the resulting residue was purified by column chromatography on silica gel using toluene-ethyl acetate (2:1) as an eluent. Fractions containing objective compound were collected and evaporated under reduced pressure to give (2R)-1-[3,5-bis(trifluoromethyl)benzoyl]-4-(4-dimethylaminophenylcarbonylmethyl)-2-(1H-indol-3-ylmethyl)piperazine (0.26 g).

mp: 185° C. (dec.)

$[\alpha]_D^{20}$: −44.6° (C=0.5, MeOH)

IR (Nujol): 3300, 1650, 1590, 1290–1150 cm$^{-1}$

NMR (DMSO-d$_6$, δ): 2.05–4.9 (11H, m); 3.03 (6H, s); 6.55–8.2 (12H, m); 10.80 (1H, s)

MASS: 617 (M+1)

EXAMPLE 9

A mixture of (2R)-1-[3,5-bis(trifluoromethyl)benzoyl]-2-(3,4-dichlorobenzyl)piperazine hydrochloride (200 mg), 4-nitrobenzyl chloride (158 mg) and triethylamine (268 μl) in tetrahydrofuran (5 ml) was refluxed overnight. After cooling, the precipitates were filtered off and the filtrate was evaporated in vacuo. The residue was purified by column chromatography on silica gel with a mixture of toluene and ethyl acetate as an eluent to give (2R)-1-[3,5-bis(trifluoromethyl)benzoyl]-2-(3,4-dichlorobenzyl)-4-(4-nitrobenzyl)piperazine (169.8 mg).

IR (Neat): 3100–2750, 1770, 1730, 1635, 1520, 1440, 1340, 1275, 1130 cm$^{-1}$

NMR (DMSO-d$_6$, δ): 2.10–5.40 (11H, m); 6.85–8.30 (10H, m)

MASS: 621 (M+1)

EXAMPLE 10

The following compound was obtained according to a similar manner to that of Example 9.

(2R)-1-[3,5-Bis(trifluoromethyl)benzoyl]-2-(3,4-dimethylbenzyl)-4-(nitrobenzyl)piperazine IR (Neat): 3100–2750, 1635, 1515, 1430, 1340, 1275, 1130 cm$^{-1}$ NMR (DMSO-d$_6$, δ): 2.00–4.85 (17H, m); 6.50–8.10 (10H, m)

MASS: 580 (M+1)

EXAMPLE 11

To a mixture of (2R)-1-[3,5-bis(trifluoromethyl)benzoyl]-2-(3,4-dimethylbenzyl)piperazine (0.25 g) and 4-acetylbenzoic acid (0.09 g) in dichloromethane (8 ml) was added triethylamine (0.2 ml) at room temperature. 2-Chloro-1-methylpyridinium iodide (0.17 g) was added, and the mixture was stirred at room temperature for 2.5 hours. The resulting mixture was concentrated under reduced pressure and the residue was partitioned between ethyl acetate and water. The organic layer was washed with aqueous sodium bicarbonate solution and dried over magnesium sulfate. After evaporation of the solvent, the residue was purified by column chromatography using ethyl acetate—n-hexane (1:1) as an eluent to afford (2R)-4-(4-acetylbenzoyl)-1-[3,5-bis(trifluoromethyl)benzoyl]-2-(3,4-dimethylbenzyl)piperazine (0.31 g).

NMR (DMSO-d$_6$, δ): 1.9–2.4 (8H, m); 2.5–5.2 (10H, m); 6.4–8.2 (10H, m) MASS: 591 (M+1)

EXAMPLE 12

To a mixture of (2R-1-[3,4-bis(trifluoromethyl)-benzoyl]-2-(3,4-dichlorobenzyl)piperazine hydrochloride (200 mg) and 4-acetylbenzoic acid (57 mg) in dichloromethane (5 ml) was added triethylamine (171 μl) at room temperature. 2-Chloro-1-methylpyridinium iodide (107 mg) was added, and the mixture was stirred at room temperature for 1.5 hours. The resulting mixture was washed successively with aqueous 0.1N hydrogen chloride solution, aqueous saturated sodium hydrogen carbonate solution and brine, and dried over magnesium sulfate. After evaporation of the solvent, the residue was purified by column chromatography using toluene-ethyl acetate (5:1) as an eluent to give (2R)-4-(4-acetylbenzoyl)-1-[3,5-bis(trifluoromethyl)benzoyl]-2-(3,4-dichlorobenzyl)piperazine (158 mg).

$[α]_D^{20}$: 11.2° (C=0.5, MeOH) IR (Neat): 3100–2850, 1685, 1630, 1440, 1275, 1130 cm$^{-1}$ NMR (DMSO-d$_6$, δ): 2.15–5.15 (9H, m); 2.62 (3H, s); 6.8–8.3 (10H, m) MASS: 633 (M+2), 631 Anal. Calcd. for $C_{29}H_{22}F_6Cl_2N_2O_3$: C 55.17; H 3.51; H 3.51; N 4.44 Found: C 55.22; H 3.53; N 4.28

EXAMPLE 13

(2R-1-[3,5-Bis(trifluoromethyl)benzoyl]-2-(3,4-dimethylbenzyl)piperazine fumarate (785 mg) was added to a mixture of 2N sodium hydroxide solution (5 ml) and ethyl acetate. The organic layer was separated, washed with brine, dried over magnesium sulfate, and evaporated in vacuo to give (2R)-1-[3,5-bis(trifluoromethyl)benzoyl]-2-(3,4-dimethylbenzyl)piperazine. A solution of this piperazine in N,N-dimethylformamide (7 ml) was added to a mixture of 2-acetylbenzoic acid (230 mg), 1-(3-dimethylaminopropyl)-3-ethylcarbodiimide hydrochloride (295 mg) and 1-hydroxybenzotriazole (208 mg) in N,N-dimethylformamide (3 ml) and the whole was stirred at room temperature overnight. The mixture was poured into a saturated sodium hydrogen carbonate solution (78 ml) and the resulting precipitates were filtered off. The filtrate was evaporate din vacuo to give (2R)-4-(2-acetylbenzoyl)-1-[3,5-bis(trifluoromethyl)benzoyl]-2-(3,4-dimethylbenzyl)piperazine (0.45 g) as a powder.

mp: 82–85° C. $[α]_d^{29}$: -22.7° (C=0.33, MeOH) IR (CH$_2$Cl$_2$): 1750, 1635, 1615 cm$^{-1}$ NMR (CDCl$_3$, δ): 1.75–5.40 (18H, m); 6.40–8.10 (10H, m) MASS: 591 (M)

EXAMPLE 14

The following compound was obtained according to a similar manner to that of Example 13.

(2R)-4-(3-Acetylbenzoyl)-1-[3,5-bis(trifluoromethyl)-benzoyl]-2-(3,4-dimethylbenzyl)piperazine mp: 155.5–157° C. $[α]_D^{24}$: 5.8° (C=0.26, MeOH) IR (Nujol): 1688, 1630 cm$^{-1}$ NMR (CDCl$_3$, δ): 2.05–2.32 (6H, m); 2.63 (3H, s); 2.70–5.40 (9H, m); 6.40–8.15 (10H, m) MASS: 592 (M+1)

EXAMPLE 15

To a stirred mixture of (2R)-1-[3,5-bis(trifluoromethyl) benzoyl]-2-(1H-indol-3-ylmethyl)-piperazine (250 mg), 2-methoxyphenylacetic acid (92 mg) and 1-hydroxybenzotriazole (75 mg) in dichloromethane (8 ml) was added 1-(3-dimethylaminopropyl)-3-ethylcarbodiimide hydrochloride (106 mg) at room temperature. After 3 hours, the reaction mixture was poured into aqueous sodium bicarbonate solution and extracted with dichloromethane. The extract was washed with brine and dried over magnesium sulfate. After evaporation of the solvent, the residue was purified by column chromatography on silica gel using ethyl acetate—n-hexane (1:1.5) as an eluent to give (2R)-1-[3,5-bis(trifluoromethyl)benzoyl]-2-(1H-indol-3-ylmethyl)-4-(2-methoxyphenylmethylcarbonyl)piperazine (290 mg) as a powder.

NMR (DMSO-d$_6$,δ): 2.6–5.0 (14H, m); 6.4–8.2 (12H, m); 10.8 (1H, m) MASS: 604 (M+1)

EXAMPLE 16

The following compounds were obtained according to a similar manner to that of Example 15.
(1) (2R)-4-(3-Acetylbenzoyl)-1-[3,5-bis(trifluoromethyl)-benzoyl]-2-(1H-indol-3-ylmethyl)piperazine mp: 186–187.5° C. $[α]_D^{29}$: 4.2° (C=0.29, MeOH) IR (Nujol): 3260, 1690, 1638, 1600, 1275 cm$^{-1}$ NMR (CDCl$_3$, δ): 1.55–5.46 (12H, m); 6.55–8.50 (13H, m) MASS: 602 (M)
(2) (2R)-4-(2-Acetylbenzoyl)-1-[3,5-bis(trifluoromethyl)-benzoyl]-2-(1H-indol-3-ylmethyl)piperazine
mp: 190–192° C. $[α]_D^{28}$: -2.1° (C=0.28, MeOH) IR (Nujol): 3300, 2700, 1750, 1720, 1635, 1630, 1275 cm$^{-1}$ NMR (CDCl$_3$, δ) : 1.46–5.45 (12H, m); 6.54–8.25 (13H, m) MASS: 602 (M)

EXAMPLE 17

To a stirred mixture of (2R)-1-[3,5-bis(trifluoromethyl) benzoyl]-4-(carboxymethyl)-2-(1H-indol-3-ylmethyl) piperazine (0.4 g) and thiomorpholine (0.08 g) in dry N,N-dimethylformamide (4 ml) were added 1-(3-dimethylaminopropyl)-3-ethylcarbodiimide hydrochloride (0.16 g) and 1-hydroxybenzotriazole (0.12 g) at room temperature. After 3 hours, the reaction mixture was poured into aqueous sodium bicarbonate solution (40 ml) and the resulting precipitate was collected by filtration. The crude product obtained was purified by column chromatography on silica gel using toluene-ethyl acetate (1:2) as an eluent to give (2R)-1-[3,5-bis(trifluoromethyl)benzoyl]-2-(1H-indol-3-ylmethyl)-4-(thiomorpholinocarbonylmethyl)piperazine (0.42 g).

$[α]_D^{19}$: -10.0° (C=0.5, MeOH) IR (Neat): 3650-3100, 1634, 1274, 1170, 1122, 898 cm$^{-1}$ NMR (DMSO-d$_6$, δ): 2.00–5.00 (19H, m); 6.60–8.20 (8H, m); 10.86 (1H, s) MASS: 599 (M+1)

EXAMPLE 18

The following compound was obtained according to a similar manner to that of Example 17.
(2R)-1-[3,5-Bis(trifluoromethyl)benzoyl]-4-[(4-(4-fluorophenyl)-1-piperazinyl)carbonyl methyl]-2-(1H-indol-3-ylmethyl)piperazine hydrochloride
mp: 183° C. (dec.) $[α]_D^{25}$: -24.0° (C=0.5, MeOH) IR (Nujol): 3600-3100, 2650-2150, 1680-1580, 1510, 1275, 1130 cm$^{-1}$ NMR (DMSO-d$_6$, δ): 3.05–5.15 (19H, m); 6.6–8.3 (12H, m); 10.40 (2H, br s); 11.02 (1H, s) MASS: 676 (M+1) (free)

EXAMPLE 19

To a stirred mixture of (2R)-1-[3,5-bis(trifluoromethyl) benzoyl]-4-(carboxymethyl)-2-(1H-indol-3-ylmethyl) piperazine (200 mg) and 4-cyclopentylpiperazine (60 mg) in dry N, N-dimethylformamide (5 ml) were added 1-(3-dimethylaminopropyl)-3-ethylcarbodiimide hydrochloride (82 mg) and 1-hydroxybenzotriazole (58 mg) at room temperature. After 7 hours, the reaction mixture was poured into water (30 ml) and extracted with ethyl acetate. The extract was washed with water and dried over magnesium sulfate. After evaporation of the solvent, the residue was purified by column chromatography on silica gel using dichloromethane-methanol (10:1) as an eluent and then treated with 4N hydrogen chloride in ethyl acetate solution (80 μl) to give (2R)-1-[3,5-bis(trifluoromethyl)benzoyl]-4-[(4-cyclopentyl-1-piperazinyl)carbonylmethyl]-2-(1H-indol-3-ylmethyl)piperazine hydrochloride (140 mg).

mp: 270° C. (dec.) $[\alpha]_D^{25}$: −24.2° (C=0.5, MeOH) IR (Nujol): 3270, 2430-2150, 1630, 1275, 1180, 1125 cm$^{-1}$ NMR (DMSO-d$_6$, δ): 1.45–5.0 (28H, m), 6.55–8.25 (8H, m); 10.90 (1H, s); 11.21 (2H, br s) MASS: 650 (M+1) (free) Anal. Calcd. for $C_{33}H_{37}F_6N_5O_2 \cdot HCl$: C 57.77; H 5.58; N 10.21 Found: C 57.91; H 5.64; N 10.18

EXAMPLE 20

A solution of methanesulfonyl chloride (1.1 g) in dichloromethane (4 ml) was added to a stirred solution of (2R)-1-[3,5-bis(trifluoromethyl)benzoyl]-4-(3-hydroxypropyl)-2-(1H-indol-3-ylmethyl)piperazine (4.99 g) and triethylamine (1.1 g) in dichloromethane (50 ml) at ice-bath temperature over a 20-minute period. After being stirred at the same temperature for 1 hour, the reaction mixture was diluted with dichloromethane (50 ml) and then washed with water and aqueous sodium bicarbonate solution. The dichloromethane layer was dried over magnesium sulfate and concentrated under reduced pressure. The residue was purified by column chromatography on silica gel using dichloromethane-methanol (30:1) as an eluent to give (2R)-1-[3,5-bis(trifluoromethyl)benzoyl]-2-(1H-indol-3-ylmethyl)-4-(3-methylsulfonyloxypropyl)piperazine (4.31 g) as a powder.

MASS: 592 (M+1)

EXAMPLE 21

The following compound was obtained according to a similar manner to that of Example 20.

(2R)-1-[3,5-Bis(trifluoromethyl)benzoyl]-2-(3,4-dimethylbenzyl)-4-(3-methylsulfonyl oxypropyl)piperazine IR (Nujol): 2950-2700, 1635, 1430, 1350, 1275, 1165, 1125 cm$^{-1}$ NMR (DMSO-d$_6$, δ): 1.8–4.95 (19H, m); 3.19 (3H, s); 4.31 (2H, t, J=6.2 Hz); 6.95–8.2 (6H, m) MASS: 581 (M+1)

EXAMPLE 22

A mixture of (2R-1-[3,5-bis(trifluoromethyl)benzoyl]-2-(1H-indol-3-ylmethyl)-4-(3-methylsulfonyloxypropyl)piperazine (0.2 g), 2-azabicyclo[3.2.2]nonane (0.05 g) and triethylamine (0.09 ml) in N,N-dimethylformamide (1 ml) was heated at 80° C. After 6 hours, the reaction mixture was poured into water (10 ml) and the resulting precipitate was collected by filtration. The crude product was dissolved in ethanol (2 ml) and then treated with 17.6% hydrogen chloride in ethanol solution (0.3 ml) to give (2R)-4-[3-(3-azabicyclo[3.2.2]non-3-yl)propyl]-1-[3,5-bis(trifluoromethyl)benzoyl]-2-(1H-indol-3-ylmethyl)piperazine dihydrochloride (0.12 g) as a powder.

mp: 194–202° C. $[\alpha]_D^{19}$: −6.0° (C=0.5, MeOH) IR (Nujol): 3600-3100, 2750-2000, 1680-1550, 1275, 1172, 1126, 900 cm$^{-1}$ NMR (DMSO-d$_6$, δ): 1.50–5.20 (29H, m); 6.60–8.25 (8H, m); 9.80 (1H, br s); 10.96 (1H, s); 11.60 (1H, br s)

EXAMPLE 23

A mixture of (2R)-1-[3,5-bis(trifluoromethyl)benzoyl]-2-(1H-indol-3-ylmethyl)-4-(3-methylsulfonyloxypropyl) piperazine (0.2 g), thiomorpholine (0.042 g) and triethylamine (0.09 ml) in dry acetonitrile (2 ml) was stirred at 90° C. for 15 hours. The reaction mixture was concentrated under reduced pressure and the resulting residue was partitioned between ethyl acetate and water. The organic layer was washed with brine and dried over magnesium sulfate. After evaporation of the solvent, the residue was purified by column chromatography on silica gel using ethyl acetate-methanol (10:1) as an eluent to give (2R)-1-(3,5-bis (trifluoromethyl)benzoyl]-2-(1H-indol-3-ylmethyl)-4-(3-thiomorpholinopropyl)piperazine. The product obtained was dissolved in ethanol and treated with 17.6% hydrogen chloride in ethanol solution to give (2R)-1-[3,5-bis (trifluoromethyl)benzoyl]-2-(1H-indol-3-ylmethyl)-4-(3-thiomorpholinopropyl)piperazine dihydrochloride (0.19 g) as a powder.

$[\alpha]_D^{20}$: −4.6° (C=0.5, MeOH) IR (Nujol): 3650-3050, 2750-1980, 1635, 1274, 1170, 1123, 900 cm$^{-1}$ NMR (DMSO-d$_6$, δ): 2.20–5.20 (23H, m); 6.50–8.25 (8H, m); 10.96 (1H, s); 11.00–11.90 (2H, m) MASS: 599 (M+1) (free)

(2R)-4-(3-Thiomorpholinopropyl)-1-[3,5-bis(trifluoromethyl)benzoyl]-2-(1H-indol-3-ylmethyl)piperazine dimaleate mp: 110–115° C. $[\alpha]_D^{21}$: −14.2° (C=0.25, MeOH) IR (Nujol): 3350, 2720, 1690, 1620, 1605, 1280, 1130 cm$^{-1}$ NMR (DMSO-d$_6$, δ): 1.70–5.12 (23H, m), 6.14 (4H, s), 6.55–8.32 (8H, m), 10.90 (1H, s)

EXAMPLE 24

The following compounds were obtained according to a similar manner to that of Example 23.
(1) (2R)-1-[3,5-Bis(trifluoromethyl)benzoyl]-2-(1H-indol-3-ylmethyl)-4-(3-morpholinopropyl)piperazine dihydrochloride mp: 265° C. (dec.) $[\alpha]_D^{31}$: −6.0° (C=0.5, MeOH) IR (Nujol): 3650-3100, 2750-2200, 1655, 1275, 1120 cm$^{-1}$ NMR (DMSO-d$_6$, δ): 2.2–2.45 (2H, m); 3.0–5.25 (21H, m); 6.55–8.25 (8H, m); 10.96 (1H, s); 11.1–12.85 (2H, m) MASS: 583 (M+1) (free) Anal. Calcd. for $C_{29}H_{32}F_6N_4O_2 \cdot 2HCl \cdot 0.4H_2O$: C 52.56; H 5.29; N 8.45 Found: C 52.54; H 5.33; N 8.25

(2)-1-[3,5-Bis(trifluoromethyl)benzoyl]-2-(3,4-dimethylbenzyl)-4-(3-thiomorpholinopropyl)piperazine dihydrochloride mp: 272° C. (dec.) $[\alpha]_D^{31}$: −11.6° (C=0.5, MeOH) IR (Nujol): 3650-3100, 2750-2650, 1635, 1270, 1120 cm$^{-1}$ NMR (DMSO-d$_6$, δ): 2.1–2.5 (8H, m); 2.7–5.2 (21H, m); 6.6–8.25 (6H, m); 11.15–11.75 (2H, m) MASS: 588 (M+1) (free)

EXAMPLE 25

A mixture of (2R)-1-[3,5-bis(trifluoromethyl)benzoyl]-2-(1H-indol-3-ylmethyl)-4-(3-methylsulfonyloxypropyl) piperazine (200 mg) and 1,2,3,4-tetrahydroisoquinoline (90 mg) in methanol (3 ml) was stirred for 1.5 hours at reflux temperature. The reaction mixture was evaporated under reduced pressure and the residue was purified by column chromatography on silica gel using ethyl acetate-methanol (10:1) as an eluent to give (2R)-1-[3,5-bis(trifluoromethyl)-benzoyl]-2-(1H-indol-3-ylmethyl)-4-[3-[1,2,3,4-tetrahydroisoquinolin-2-yl]propyl]piperazine (167 mg) as a powder.

$[\alpha]_D^{20}$: −9.6° (C=0.5, MeOH) IR (Neat): 3260, 1630, 1430, 1380, 1350, 1270 cm$^{-1}$ NMR (DMSO-d$_6$, δ): 1.60–4.93 (21H, m); 6.60–8.37 (12H, m); 10.85 (1H, s) MASS: 629 (M+1)

EXAMPLE 26

The following compound was obtained according to a similar manner to that of Example 25.

(2R)-1-[3,5-Bis(trifluoromethyl)benzoyl]-2-(1H-indol-3-ylmethyl)-4-[3-(4,5,6,7-tetrahydrothieno[3,2-c]pyridin-5-yl)propyl]piperazine $[\alpha]_D^{18}$: −9.0° (C=0.5, MeOH) IR (Neat): 3260, 1630, 1430, 1350, 1275 cm$^{-1}$ NMR (DMSO-d$_6$, δ): 1.55–4.97 (21H, m); 6.30–8.24 (10H, m); 10.85 (1H, s) MASS: 635 (M+1)

EXAMPLE 27

A mixture of (2R)-1-[3,5-bis(trifluoromethyl)benzoyl]-2-(1H-indol-3-ylmethyl)-4-(3-methylsulfonyloxypropyl)piperazine (150 mg) and 4-cyano-4-phenylpiperidine hydrochloride (70 mg) in methanol (5 ml) was stirred at reflux temperature in the presence of sodium carbonate (100 mg). After 2 hours, the reaction mixture was evaporated under reduced pressure. The residue was extracted with ethyl acetate and the extract was concentrated under reduced pressure. The residue was purified by column chromatography on silica gel using ethyl acetate-methanol (10:1) as an eluent to give (2R)-1-[3,5-bis(trifluoromethyl)benzoyl]-4-[3-(4-cyano-4-phenylpiperidino)propyl]-2-(1H-indol-3-ylmethyl)piperazine (89 mg) as a powder.

$[\alpha]_D^{20}$: −19.2° (C=0.5, MeOH) NMR (DMSO-d$_6$, δ): 1.52–4.96 (23H, m); 6.60–8.26 (13H, m); 10.85 (1H, s) MASS: 682 (M+1)

EXAMPLE 28

A mixture of (2R)-1-[3,5-bis(trifluoromethyl)benzoyl]-2-(1H-indol-3-ylmethyl)-4-(3-methylsulfonyloxypropyl)piperazine (200 mg) and spiro[indan-1,4'-piperidine] (70 mg) in acetonitrile (3 ml) was refluxed for 1.5 hours. The reaction mixture was evaporated under reduced pressure and then the residue was purified by column chromatography on silica gel using dichloromethane-methanol (10:1) as an eluent to give (2R)-1-[3,5-bis(trifluoromethyl)benzoyl]-4-[3-(spiro[indan-1,4'-piperidine]-1'-yl)propyl]-2-(1H-indol-3-ylmethyl)piperazine (208 mg) as a powder.

$[\alpha]_D^{22}$: −21.4° (C=1.0, MeOH) IR (Neat): 3260, 1630, 1435, 1380, 1350, 1275 cm$^{-1}$ NMR (DMSO-d$_6$, δ): 1.45–5.00 (27H, m); 6.62–8.28 (12H, m); 10.88 (1H, s) MASS: 683 (M+1)

EXAMPLE 29

A mixture of (2R)-1-[3,4-bis(trifluoromethyl)benzoyl]-2-(3,4-dichlorobenzyl)-4-(4-nitrobenzyl)piperazine (157 mg), ammonium chloride (15.7 mg) and iron powder (157 mg) in a mixture of ethanol (5 ml) and water (1.25 ml) was refluxed for 1.5 hours. After cooling, the precipitates were filtered off and the filtrate was evaporated in vacuo. The residue was purified by column chromatography on silica gel with a mixture of toluene and ethyl acetate as an eluent to give (2R)-4-(4-aminobenzyl)-1-[3,5-bis(trifluoromethyl)benzoyl]-2-(3,4-dichlorobenzyl)piperazine (128.4 mg).

IR (Neat): 3350, 2970-2700, 1630, 1515, 1460, 1430, 1275, 1130 cm$^{-1}$ NMR (DMSO-d$_6$, δ): 1.95–5.05 (13H, m); 6.50–8.25 (10H, m) MASS: 592 (M+2), 590 (M)

EXAMPLE 30

The following compound was obtained according to a similar manner to that of Example 29.

(2R)-4-(4-Aminobenzyl)-1-[3,5-bis(trifluoromethyl)-benzoyl]-2-(3,4-dimethylbenzyl)piperazine IR (Neat): 3450, 3300, 3100-2650, 1625, 1515, 1435, 1275, 1125 cm$^{-1}$ NMR (DMSO-d$_6$, δ): 1.90–4.80 (17H, m); 4.98 (2H, s); 6.40–8.20 (10H, m) MASS: 550 (M+1)

EXAMPLE 31

Piridine (23 µl) and acetyl chloride (16 µl) were successively added to a solution of (2R)-4-(4-aminobenzyl)-1-[3,5-bis(trifluoromethyl)benzoyl]-2-(3,4-dichlorobenzyl)-piperazine (113 mg) and the whole was stirred at room temperature for 1.5 hours. The mixture was poured into water and the separated oil was extracted with ethyl acetate. The extract was washed with water, dried over magnesium sulfate and evaporate in vacuo. The residue was purified by column chromatography on silica gel with a mixture of toluene and ethyl acetate as an eluent to give (2R)-4-(4-acetylaminobenzyl)-1-[3,5-bis(trifluoromethyl)benzoyl]-2-(3,4-dichlorobenzyl)piperazine (98.3 mg). The obtained piperazine was dissolved in ethyl acetate. 4N Hydrogen chloride in ethyl acetate solution (43 µl) was added to the solution and the mixture was evaporated in vacuo. The residue was triturated with n-hexane to give (2R)-4-(4-acetylaminobenzyl)-1-[3,5-bis(trifluoromethyl)benzoyl]-2-(3,4-dichlorobenzyl)piperazine hydrochloride (92 mg).

$[\alpha]_D^{20}$: −11.8° (C=0.5, MeOH) IR (Neat): 3600-3150, 2750-2100, 1635, 1600, 1525, 1415, 1270, 1130 cm$^{-1}$ NMR (DMSO-d$_6$, δ): 2.07 (3H, s); 2.85–5.15 (11H, m); 6.80–8.30 (10H, m); 10.13 (1H, s) MASS: 632 (M+1) (free)

EXAMPLE 32

The following compound was obtained according to a similar manner to that of Example 31.

(2R)-4-(4-Acetylaminobenzyl)-1-[3,5-bis(trifluoromethyl)benzoyl]-2-(3,4-dimethylbenzyl) piperazine hydrochloride $[\alpha]_D^{25}$: −23.2° (C=0.5, MeOH) IR (Nujol): 3650-3100, 2750-2100, 1640, 1600, 1530, 1275, 1170, 1130 cm$^{-1}$ NMR (DMSO-d$_6$, δ): 1.96–2.10 (9H, m); 2.80–5.05 (11H, m); 6.50–8.30 (10H, m); 10.17 (1H, s); 11.00–11.40 (1H, m) MASS: 592 (M+1) (free)

EXAMPLE 33

(2R)-1-[3,5-Bis(trifluoromethyl)benzoyl]-2-(1H-indol-3-ylmethyl)-4-(thiomorpholinocarbonylmethyl)piperazine was converted to the corresponding hydrochloride by treatment with 17.6% hydrogen chloride in ethanol solution.

IR (Nujol): 3650-3100, 2750-1980, 1638, 1276, 1171, 1129, 900 cm$^{-1}$ NMR (DMSO-d$_6$, δ): 2.55–5.15 (19H, m); 6.60–8.25 (8H, m); 10.99 (1H, s) MASS: 599 (M+1) (free)

Preparation 1

A mixture of formaldehyde (37% in water, 20.7 ml) and morpholine (17.1 ml) was adjusted to pH 3.5 with diluted sulfuric acid. Propargyl alcohol (10 g), potassium iodide (0.3 g), and copper (II) sulfate (0.14 g) were added to the solution and the whole was stirred at 95° C. for 6 hours. After cooling, the insoluble material was removed by filtration and the pH of the filtrate was adjusted to 9 with 24% sodium hydroxide solution. Brine (100 ml) was added to the solution and the solution was extracted with a mixture of ethyl acetate and ethanol (10:1) eight times and then with n-butanol six times. The combined extract was dried over magnesium sulfate and evaporated in vacuo. The residue was distilled in reduced pressure to give 4-morpholino-2-butyn-1-ol (14.03 g).

bp: 124–131° C. IR (Neat): 3350, 2850, 1105, 1000 cm$^{-1}$ NMR (CDCl$_3$, δ): 2.18 (1H, br s), 2.57 (4H, t, J=4.7 Hz), 3.31 (2H, t, J=1.9 Hz), 3.75 (4H, t, J=4.7 Hz), 4.30 (2H, t, J=1.9 Hz) MASS: 156 (M+1)

Preparation 2

The following compound was obtained according to a similar manner to that of Preparation 1 with the exception of purification by column chromatography on silica gel using a mixture of ethyl acetate and methanol (30:1) as an eluent instead of distillation in reduced pressure.

4-Thiomorpholino-2-butyn-1-ol

IR (Neat): 3350, 2900, 2800, 1420, 1330, 1115, 1100 cm$^{-1}$ NMR (CDCl$_3$, δ): 193 (1H, br s), 2.65–2.90 (8H, m), 3.32 (2H, t, J=1.9 Hz), 4.30 (2H, t, J=1.9 Hz) MASS: 172 (M+1)

Preparation 3

Thionyl chloride (2.1 ml) was added to a solution of 4-morpholino-2-butyn-1-ol (1.47 g) in dichloromethane (10 ml) with ice bath cooling. After stirring for 0.5 hour, the solution was evaporate din vacuo. The residue was triturated with ethyl acetate to give 4-morpholino-2-butynyl chloride hydrochloride (1.91 g).

mp: 162–165° C. IR (Nujol): 2640, 2510, 2450, 2350 cm$^{-1}$ NMR (DMSO-d$_6$, δ): 3.31 (4H, br s), 3.92 (4H, br s), 4.21 (2H, t, J=1.9 Hz), 4.57 (2H, t, J=1.9 Hz), 12.23 (1H, br s) MASS: 174 (M) (free)

Preparation 4

The following compound was obtained according to a similar manner to that of Preparation 3.

4-Thiomorpholino-2-butynyl chloride hydrochloride mp: 185–187° C. IR (Nujol): 2600, 2450, 2380, 1280, 1260, 1160, 915 cm$^{-1}$ NMR (DMSO-d$_6$, δ): 2.58–4.00 (8H, m), 4.21 (2H, t, J=2.0 Hz), 4.58 (2H, t, J=2.0 Hz), 12.08 (1H, br s) MASS: 190 (M) (free)

Preparation 5

A mixture of 4-chloro-1-(4-fluorophenyl-1-butanone (500 mg), ethylene glycol (247 mg) and catalytic amount of p-toluenesulfonic acid monohydrate in benzene (5 ml) was refluxed for 20 hours with continuous removal of water using Dean-Stark apparatus. After cooling, the solution was washed successively with 1N NaOH solution and brine, dried over magnesium sulfate, and evaporated in vacuo to give 4-chloro-1-(4-fluorophenyl)-1-butanone cyclic ethylene acetal (613.2 mg) as an oil.

IR (Neat): 2950, 2870, 1600, 1500, 1220, 1030 cm$^{-1}$ NMR (DMSO-d$_6$, δ): 1.60–1.80 (2H, m), 1.90–2.00 (2H, m), 3.61 (2H, t , J=6.5 Hz), 3.70–4.10 (4H, m), 7.10–7.50 (4H, m) MASS: 245 (M+1), 209

EXAMPLE 34

A mixture of (2R)-1-[3,5-bis(trifluoromethyl)benzoyl]-2-(2-naphthylmethyl)piperazine (1.0 g) and 3-bromopropanol (330 mg) in N,N-dimethylformamide (2.5 ml) was stirred at room temperature in the presence of powdered potassium carbonate (444 mg). After 17 hours, the reaction mixture was diluted with ethyl acetate (30 ml) and then washed successively with water and brine, and dried over magnesium sulfate. Evaporation of the solvent in vacuo gave (2R)-1-[3,5-bis(trifluoromethyl)benzoyl]-4-(3-hydroxypropyl)-2-(2-naphthylmethyl)piperazine (1.19 g).

IR (Neat): 3425, 1635, 1430, 1340, 1275, 1170, 1130 cm$^{-1}$ NMR (CDCl$_3$, δ): 1.50–5.28 (16H, m), 7.40–7.93 (10H, m) MASS: 525 (M+1)

EXAMPLE 35

A mixture of (2R)-1-[3,5-bis(trifluoromethyl)benzoyl]-2-(2-naphthylmethyl)piperazine (200 mg) and 1-(4-chloro-2-butynyl)morpholine hydrochloride (95 mg) in N,N-dimethylformamide (0.5 ml) was stirred at room temperature in the presence of powdered potassium carbonate (177 mg). After 17 hours, the reaction mixture was diluted with ethyl acetate (30 ml) and then washed successively with water and brine, and dried over magnesium sulfate. After evaporation of the solvent in vacuo, the resulting residue was purified by column chromatography on silica gel using ethyl acetate as an eluent. The product obtained was dissolved in ethyl acetate and treated with 4N hydrogen chloride in ethyl acetate solution to give (2R)-1-[3,5-bis(trifluoromethyl)benzoyl]-4-(4-morpholino-2-butynyl)-2-(2-naphthylmethyl)piperazine dihydrochloride (257 mg).

$[\alpha]_D^{21}$: −21.5° (C=0.5, MeOH) IR (Nujol): 3350, 2550, 1630, 1275 cm$^{-1}$ NMR (DMSO-d$_6$, δ): 2.80–5.31 (21H, m), 7.0–8.28 (10H, m) MASS: 604 (M+1) (free)

EXAMPLE 36

A mixture of (2R)-1-[3,5-bis(trifluoromethyl)benzoyl]-2-(3,4-dichlorobenzyl)piperazine hydrochloride (150 mg) and 1-(4-chloro-2-butynyl)morpholine hydrochloride (63 mg) in N,N-dimethylformamide (0.5 ml) was stirred at room temperature in the presence of powdered potassium carbonate (160 mg). After 17 hours, the reaction mixture was diluted with ethyl acetate (30 ml) and then washed successively with water and brine, and dried over magnesium sulfate. After evaporation of the solvent in vacuo, the resulting residue was purified by column chromatography on silica gel using a mixture of ethyl acetate and methanol (10:1) as an eluent to give (2R)-1-[3,5-bis(trifluoromethyl)benzoyl]-2-(3,4-dichlorobenzyl)-4-(4-morpholino-2-butynyl)piperazine. The product obtained was dissolved in ethyl acetate and treated with 4N hydrogen chloride in ethyl acetate solution to give (2R)-1-[3,5-bis(trifluoromethyl)benzoyl]-2-(3,4-dichlorobenzyl)-4-(4-morpholino-2-butynyl)piperazine dihydrochloride (155 mg).

$[\alpha]_D^{20}$: −3.9° (C=0.5, MeOH) IR (Neat): 3400, 2350, 1640, 1425, 1275 cm$^{-1}$ NMR (DMSO-d$_6$, δ): 2.91–5.20 (21H, m), 7.0–8.26 (6H, m) MASS: 622 (M+1) (free)

EXAMPLE 37

The following compounds were obtained according to a similar manner to that of Example 7.

(1) (2R)-4-(4-Morpholino-2-butynyl)-1-[3,5-bis(trifluoromethyl)benzoyl]-2-(1H-indol-3-ylmethyl)-piperazine dihydrochloride mp: 165–169° C. $[\alpha]_D^{21}$: −0.4° (C=0.26, MeOH) IR (Nujol): 3350, 2550, 2320, 1635, 1550, 1270, 1120 cm$^{-1}$ NMR (DMS-d$_6$, δ): 2.80–5.25 (21H, m), 6.56–8.30 (8H, m), 10.96 (1H, s) MASS: 593 (M) (free)

(2) (2R)-4-(4-Morpholino-2-butynyl)-1-[3,5- bis(trifluoromethyl)benzoyl]-2-(3,4-dimethylbenzyl) piperazine dihydrochloride mp$[\alpha]_D^{21}$: −11.5° (C=0.26, MeOH) IR (Nujol): 3350, 2650, 2300, 1655, 1640, 1275, 1120 cm$^{-1}$ NMR (DMSO-d$_6$, δ): 2.02–2.30 (7H, m), 2.64–4.30 (20H, m), 6.60–8.30 (6H, m) MASS: 582 (M) (free)

(3) (2R)-4-(4-Thiomorpholino-2-butynyl)-1-[3,5-bis(trifluoromethyl)benzoyl]-2-(3,4-dimethylbenzyl)-piperazine dihydrochloride mp: 162–170° C. $[\alpha]_D^{22}$: −9.4° (C=0.27, MeOH) IR (Nujol): 3350, 2650, 2320, 1655, 1640, 1275, 1125 cm$^{-1}$ NMR (DMSO-d$_6$, δ): 2.04–2.35 (7H, m) 2.65–5.25 (20H, m), 6.57–8.28 (6H, m) MASS: 598 (M) (free)

(4) (2R)-4-(4-Thiomorpholino-2-butynyl)-1-[3,5-bis(trifluoromethyl)benzoyl]-2-(1H-indol-3-ylmethyl)piperazine dihydrochloride mp: 166–170° C. [α]$_D^{22}$: −1.5° (C=0.26, MeOH) IR (Nujol): 3350, 2650, 2300, 1635, 1275, 1125 cm$^{-1}$ NMR (DMSC-d$_6$, δ): 2.58–5.30 (21H, m), 6.54–8.30 (8H, m), 10.98 (1H, br s), 12.10 (2H, br s) MASS: 609 (M) (free)

(5) (2R)-4-(2-Morpholinoethyl)-1-[3,5-bis(trifluoromethyl)benzoyl]-2-(3,4-dimethylbenzyl)piperazine dihydrochloride mp: 223–228° C. [α]$_D^{27.2}$: −13.0° (C=0.28, MeOH) IR (Nujol): 3350, 2550, 1630, 1450, 1275, 1120 cm$^{-1}$ NMR (DMSO-d$_6$, δ): 1.95–5.25 (27H, m), 6.50–8.32 (6H, m), 10.80–11.90 (2H, br m) MASS: 558 (M) (free)

(6) (2R)-4-(2-Thiomorpholinoethyl)-1-[3,5-bis(trifluoromethyl)benzoyl]-2-(1H-indol-3-ylmethyl)piperazine dihydrochloride mp: 170–182° C. [α]$_D^{28.5}$: −4.5° (C=0.39, MeOH) IR (Nujol): 3350, 2600, 1640, 1275, 1125 cm$^{-1}$ NMR (DMSO-d$_6$, δ): 2.60–5.30 (21H, m), 6.50–8.30 (8H, m), 10.96 (1H, s), 11.10–12.10 (2H, br m) MASS: 585 (M) (free)

(7) (2R)-4-(2-Morpholinoethyl)-1-[3,5-bis(trifluoromethyl)benzoyl]-2-(1H-indol-3-ylmethyl)piperazine dihydrochloride mp: 170–176° C. [α]$_D^{28.5}$: −3.0° (C=0.30, MeOH) IR (Nujol): 3350, 2570, 1640, 1275, 1125 cm$^{-1}$ NMR (DMSO-d$_6$, δ): 2.60–5.30 (21H, m), 6.55–8.40 (8H, m), 10.95 (1H, s), 11.10–12.04 (2H, br m) MASS: 569 (M) (free)

(8) (2R)-4-(2-Thiomorpholinoethyl)-1-[3,5-bis(trifluoromethyl)benzoyl]-2-(3,4-dimethylbenzyl)piperazine dihydrochloride mp: 261.5° C. [α]$_D^{28.5}$: −1.9° (C=0.29, DMF) IR (Nujol): 3350, 2350, 1640, 1275, 1130 cm$^{-1}$ NMR (DMSO-d$_6$, δ): 2.00–5.30 (27H, m), 6.60–8.30 (6H, m), 10.60–12.00 (2H, br m) MASS: 574 (M) (free)

EXAMPLE 38

A mixture of (2R)-1-[3,5-bis(trifluoromethyl)benzoyl]-2-(1H-indol-3-ylmethyl)piperazine (300 mg), 4-chloro-1-(4-fluorophenyl)-1-butanone cyclic ethylene acetal (161 mg), potassium carbonate (182 mg), and potassium iodide (109 mg) in acetonitrile (10 ml) was refluxed for 20 hours. After cooling, the insoluble material was removed by filtration and the filtrate was evaporated in vacuo. The residue was purified by column chromatography on silica gel with a mixture of toluene and ethyl acetate as an eluent to give (2R)-4-[4,4-ethylenedioxy-4-(4-fluorophenyl)butyl]-1-[3,5-bis(trifluoromethyl)benzoyl]-2-(1H-indol-3-ylmethyl)piperazine as a powder. This compound was further purified by washing with diisopropyl ether.

mp: 145–146° C. IR (Nujol): 3200, 1620, 1600, 1275, 1120 cm$^{-1}$ NMR (DMSO-d$_6$, δ): 1.35–1.55 (2H, m), 1.80–4.90 (17H, m), 6.55–8.20 (12H, m), 10.87 (1H, br s) MASS: 664 (M+1)

EXAMPLE 39

To a stirred mixture of (2R)-1-[3,5-bis(trifluoromethyl)benzoyl]-4-(carboxymethyl)-2-(1H-indol-3-ylmethyl)piperazine (0.2 g) and 3-azabicyclo[3.2.2]nonane (0.05 g) in dry N,N-dimethylformamide (2 ml) were added 1-(3-dimethylaminopropyl)-3-ethylcarbodiimide hydrochloride (0.082 g) and 1-hydroxybenzotriazole (0.058 g) at room temperature. After 6 hours, the reaction mixture was poured into aqueous sodium bicarbonate solution (20 ml) and the resulting precipitate was collected by filtration. The crude product obtained was purified by column chromatography on silica gel using toluene-ethyl acetate (1:2) as an eluent and treated with 17.6% hydrogen chloride in ethanol solution to give (2R)-4-[(3-azabicyclo[3.2.2]non-3-yl)carbonylmethyl]-1-[3,5-bis(trifluoromethyl)benzoyl]-2-(1H-indol-3-ylmethyl)piperazine hydrochloride (0.2 g) as a white powder.

[α]$_D^{20}$: −32.0° (C=0.5, MeOH); IR (Nujol): 3650–3100, 2750–2000, 1637, 1276, 1172, 1130, 900 cm$^{-1}$; NMR (DMSO-d$_6$, δ): 1.50–1.75 (8H, m), 2.07 (2H, br s), 3.15–5.10 (15H, m), 6.60–8.25 (8H, m), 10.15 (1H, br s), 11.00 (1H, s); MASS: 621 (M+1) (free).

EXAMPLE 40

To a stirred mixture of (2R)-1-[3,5-bis(trifluoromethyl)benzoyl]-4-(4-carboxybenzyl)-2-(1H-indol-3-ylmethyl)piperazine (150 mg) and diethylamine hydrochloride (28 mg) in dry dichloromethane (5 ml) were added a solution of 1-(3-dimethylaminopropyl)-3-ethylcarbodiimide (40 mg) in dichloromethane (1ml) and 1-hydroxybenzotriazole (34 mg) at room temperature. After 5 hours, the reaction mixture was poured into aqueous sodium bicarbonate solution (20 ml). The organic layer was separated and washed with brine and dried over magnesium sulfate. The crude product obtained was purified by column chromatography on silica gel using ethyl acetate-n-hexane (4:1) to give (2R)-1-[3,5-bis(trifluoromethyl)benzoyl]-4-[4-(N,N-diethylaminocarbonyl)benzyl]-2-(1H-indol-3-ylmethyl)piperazine (107 mg) as a powder.

[α]$_D^{21}$: −40.3° (C=0.5, MeOH); IR (Neat): 3250, 1620, 1430, 1275, 1130 cm$^{-1}$; NMR (CDCl$_3$, δ): 1.10–5.00 (25H, m), 6.40–8.00 (8H, m, 9.14 (1H, s); MASS: 645 (M+1).

EXAMPLE 41

To a stirred mixture of (2R)-1-[3,5-bis(trifluoromethyl)benzoyl]-4-(3-hydroxypropyl)-2-(2-naphthylmethyl)piperazine (1.1 g) and triethylamine (425 mg) in dichloromethane (10 ml) was added dropwise methanesulfonyl chloride (252 mg) at ice-bath temperature. After 2 hours, the reaction mixture was washed with water and then dried over magnesium sulfate. After evaporation of the solvent, the resulting residue was chromatographed on silica gel using ethyl acetate as an eluent to give (2R)-1-[3,5-bis(trifluoromethyl)benzoyl]-2-(2-naphthylmethyl)-4-(3-methylsulfonyloxypropyl)piperazine (988 mg).

IR (Neat): 1635, 1430, 1350, 1280, 1170, 1130 cm$^{-1}$; NMR (CDCl$_3$, δ): 1.59 (3H, s), 1.90–5.28 (15H, m), 7.40–7.90 (10H, m); MASS: 603 (M+1).

EXAMPLE 42

The following compounds were obtained according to a similar manner to that of Example 41.

(1) (2R)-1-[3,5-Bis(trifluoromethyl)benzoyl]-2-(3,4-dichlorobenzyl)-4-(3-methylsulfonyloxypropyl)piperazine (IR (Neat): 1630, 1470, 1430, 1340, 1270 cm$^{-1}$; NMR (CDCl$_3$, δ): 1.55–5.14 (15H, m), 3.04 (3H, s), 7.00–7.95 (6H, m).

(2) (2R)-1-[3,5-Bis(trifluoromethyl)benzoyl]-2-(2-naphthylmethyl)-4-(2-methylsulfonyloxyethyl)piperazine IR (Neat): 1635, 1430, 1350, 1275, 1170, 1125 cm$^{-1}$.

EXAMPLE 43

A mixture of (2R)-1-[3,5-bis(trifluoromethyl)benzoyl]-2-(2-naphthylmethyl)-4-(3-methylsulfonyloxypropyl)

piperazine (250 mg), thiomorpholine (43 mg) and triethylamine (46 mg) in dry methanol (5 ml) was refluxed for 2 hours. The reaction mixture was concentrated under reduced pressure and the resulting residue was purified by column chromatography on silica gel using ethyl acetate as an eluent. The product obtained was dissolved in ethyl acetate and treated with 4N hydrogen chloride in ethyl acetate solution to give (2R)-1-[3,5-bis(trifluoromethyl)benzoyl]-2-(2-naphthylmethyl)-4-(3-thiomorpholinopropyl)piperazine dihydrochloride (195 mg).

$[\alpha]_D^{23}$: −23.0° (C=0.5, MeOH); IR (Nujol): 3400, 2500, 1640, 1275, 1170, 1130 cm$^{-1}$; NMR (CDCl$_3$, δ): 1.50–5.69 (23H, m), 7.34–7.93 (10H, m); MASS: 610 (M+1) (free).

EXAMPLE 44

The following compounds were obtained according to a similar manner to that of Example 43.

(1) (2R)-1-[3,5-Bis(trifluoromethyl)benzoyl]-2-(2-naphthylmethyl)-4-(2-morpholinoethyl)piperazine Dihydrochloride $[\alpha]_D^{23}$: −25.2° (C=0.5, MeOH); IR (Nujol): 3400, 2510, 2425, 1635, 1425, 1275, 1170, 1130 cm$^{-1}$; NMR (DMSO-d$_6$, δ): 2.88–5.31 (21H, m), 7.07–8.24 (10H, m); MASS: 580 (M+1) (free).

(2) (2R)-1-[3,5-Bis(trifluoromethyl)benzoyl]-2-(2-naphthylmethyl)-4-(2-thiomorpholinoethyl)piperazine Dihydrochloride $[\alpha]_D^{22}$: −23.7° (C=0.5, MeOH); IR (Nujol): 2350, 1640, 1270, 1180 cm$^{-1}$; NMR (DMSO-d$_6$, δ): 2.80–5.31 (21H, m), 7.03–8.20 (10H, m); MASS: 596 (M+1) (free).

(3) (2R)-1-[3,5-Bis(trifluoromethyl)benzoyl]-2-(1H-indol-3-ylmethyl)-4-[3-(4-oxopiperidino)propyl]piperazine $[\alpha]_D^{24}$: −19.0° (C=0.5, MeOH); IR (Nujol): 3270, 1720, 1625, 1430, 1340, 1275, 1125 cm$^{-1}$; NMR (CDCl$_3$, δ): 1.66–5.20 (23H, m), 6.69–8.28 (8H, m); MASS: 595 (M+1).

(4) (2R)-1-[3,5-Bis(trifluoromethyl)benzoyl]-2-(3,4-dichlorobenzyl)-4-(3-thiomorpholinopropyl)piperazine Dihydrochloride $[\alpha]_D^{18}$: +2.2° (C=0.5, MeOH); IR (Nujol): 3400, 2400, 1650, 1280 cm$^{-1}$; NMR (DMSO-d$_6$, δ): 2.10–5.20 (23H, m), 6.92–8.32 (6H, m), 11.12–11.72 (2H, m); MASS: 628 (M+1) (free).

(5) (2R)-1-[3,5-Bis(trifluoromethyl)benzoyl]-2-(3,4-dichlorobenzyl)-4-(3-morpholinopropyl)piperazine Dihydrochloride $[\alpha]_D^{19}$: +2.3° (C=0.5, MeOH); IR (Nujol): 3400, 2550, 2450, 1650, 1280 cm$^{-1}$; NMR (DMSO-d$_6$, δ): 2.10–5.20 (23H, m), 6.94–8.34 (6H, m), 11.08–11.76 (2H, m); MASS: 612 (M+1) (free).

(6) (2R)-4-[3-(4-Acetylpiperidino)propyl]-1-[3,5-bis(trifluoromethyl)benzoyl]-2-(1H-indol-3-ylmethyl)piperazine Dihydrochloride $[\alpha]_D^{20}$: −7.2° (C=0.5, MeOH); IR (Nujol): 3300, 2600, 1700, 1630, 1275 cm$^{-1}$; NMR (DMSO-d$_6$, δ): 1.67–5.24 (24H, m), 2.16 (3H, s), 6.62–8.28 (8H, m), 10.95 (1H, s); MASS: 623 (M+1) (free).

(7) (2R)-4-[3-(Thiazolidin-3-yl)propyl]-1-[3,5-bis(trifluoromethyl)benzoyl]-2-(1H-indol-3-ylmethyl)piperazine Dihydrochloride $[\alpha]_D^{25}$: −5.4° (C=0.5, MeOH); IR (Nujol): 3600–3100, 2700–2250, 1660–1580, 1270, 1120 cm$^{-1}$; NMR (DMSO-d$_6$, δ): 2.20–2.40 (2H, m), 3.00–5.20 (19H, m), 6.40–8.25 (8H, m), 10.97 (1H, m), 11.20–11.90 (2H, m); MASS: 585 (M+1) (free).

(8) (2R)-4-[3-(4-Phenyl-1-piperazinyl)propyl]-1-[3,5-bis(trifluoromethyl)benzoyl]-2-(1H-indol-3-ylmethyl)piperazine Trihydrochloride $[\alpha]_D^{25}$: −8.0° (C=0.5, MeOH); IR (Nujol): 3600–3100, 2750–2300, 1630, 1275, 1120 cm$^{-1}$; NMR (DMSO-d$_6$, δ): 2.05–2.45 (2H, m), 3.05–5.20 (21H, m), 6.60–8.05 (13H, m), 10.97 (1H, s), 11.00–11.85 (3H, m); MASS: 658 (M+1) (free).

(9) (2R)-4-[3-(4-Cyclohexyl-1-piperazinyl)propyl]-1-[3,5-bis(trifluoromethyl)benzoyl]-2-(1H-indol-3-ylmethyl)piperazine Trihydrochloride $[\alpha]_D^{25}$: −7.8° (C=0.5, MeOH); IR (Nujol): 3600–3100, 2650–2200, 1640–1600, 1370, 1270, 1120 cm$^{-1}$; NMR (DMSO-d$_6$, δ): 1.00–2.40 (11H, m), 3.00–5.30 (23H, m), 6.60–8.30 (8H, m), 10.97 (1H, s), 11.30–12.30 (3H, m); MASS: 664 (M+1) (free).

EXAMPLE 45

A mixture of (2R)-1-[3,5-bis(trifluoromethyl)benzoyl]-2-(1H-indol-3-ylmethyl)-4-(2-methylsulfonyloxyethyl)piperazine (200 mg), 4-aminomorpholine (36 mg) and triethylamine (52 mg) in dry methanol (5 ml) was refluxed for 2 hours. The reaction mixture was concentrated under reduced pressure and the resulting residue was partitioned between ethyl acetate and aqueous sodium hydrogen carbonate solution. The organic layer was washed with brine and dried over magnesium sulfate. After evaporation of the solvent, the residue was purified by column chromatography on silica gel using a mixture of ethyl acetate and methanol (10:1) as an eluent to afford (2R)-1-[3,5-bis(trifluoromethyl)benzoyl]-2-(1H-indol-3-ylmethyl)-4-[2-(morpholinoamino)ethyl]piperazine (55 mg).

$[\alpha]_D^{22}$: −16.2° (C=0.5, MeOH); IR (Nujol): 3300, 1615, 1275 cm$^{-1}$; NMR (DMSO-d$_6$, δ): 2.14–5.10 (21H, m), 6.0–8.26 (8H, m), 10.91 (1H, s); MASS: 584 (M+1).

EXAMPLE 46

A mixture of (2R)-1-[3,5-bis(trifluoromethyl)benzoyl]-2-(1H-indol-3-ylmethyl)-4-(3-methylsulfonyloxypropyl)piperazine (100 mg) and 4-phenylpiperidine (60 mg) in acetonitrile (3 ml) was refluxed for 2 hours. The reaction mixture was concentrated under reduced pressure and the resulting residue was purified by column chromatography on silica gel using ethyl acetate-methanol (5:1) as an eluent to give (2R)-1-[3,5-bis(trifluoromethyl)benzoyl]-2-(1H-indol-3-ylmethyl)-4-[3-(4-phenylpiperidino)propyl]piperazine (90 mg).

$[\alpha]_D^{20}$: −24.6° (C=1.0, MeOH); IR (Neat): 3250, 1630, 1430, 1275, 1130 cm$^{-1}$; NMR (DMSO-d$_6$, δ): 1.52–4.93 (24H, m), 6.60–8.28 (13H, m), 10.87 (1H, s); MASS: 657 (M+1).

EXAMPLE 47

A solution of (2R)-2-(3,4-dichlorobenzyl)-1-[3,5-bis(trifluoromethyl)benzoyl]-4-(2-hydroxyethyl)piperazine (50 mg) in ethyl acetate (3 ml) was treated with 4N hydrogen chloride in ethyl acetate solution (0.2 ml) and the resulting mixture was concentrated in vacuo to give (2R)-2-(3,4-dichlorobenzyl)-1-[3,5-bis(trifluoromethyl)benzoyl]-4-(2-hydroxyethyl)piperazine hydrochloride (45 mg) as a powder.

IR (Neat): 3260, 2550, 1640, 1425, 1275 cm$^{-1}$; NMR (DMSO-d$_6$, δ): 2.80–5.53 (13H, m), 6.91–8.32 (6H, m), 10.96 (1H, br s); MASS: 530 (M+1) (free).

EXAMPLE 48

The following compounds were obtained according to a similar manner to that of Example 47.

(1) (2R)-4-(4-Aminobenzyl)-1-[3,5-bis(trifluoromethyl) benzoyl]-2-(3,4-dimethylbenzyl)piperazine Dihydrochloride mp: 179° C. (dec.); $[\alpha]_D^{25}$: −16.6° (C=0.5, MeOH); IR (Nujol): 3400–3050, 2650–2300, 1660–1580, 1275, 1125 cm$^{-1}$; NMR (DMSO-d$_6$, δ): 2.00–2.20 (6H, m), 2.80–5.05 (11H, m), 6.45–8.25 (10H, m), 11.40–11.90 (2H, m); MASS: 550 (M+1) (free).

(2) (2R)-4-(4-Nitrobenzyl)-1-[3,5-bis(trifluoromethyl) benzoyl]-2-(3,4-dimethylbenzyl)piperazine Dihydrochloride mp: 140° C. (dec.); $[\alpha]_D^{25}$: −18.4° (C=0.5, MeOH); IR (Nujol): 3600–3200, 2650–2200, 1640, 1520, 1350, 1275, 1130 cm$^{-1}$; NMR (DMSO-d$_6$, δ): 2.00–2.20 (6H, m), 2.80–5.00 (11H, m), 6.50–8.40 (10H, m); MASS: 580 (M+1) (free).

EXAMPLE 49

To a solution of (2R)-4-[4,4-ethylenedioxy-4-(4-fluorophenyl)butyl]-1-[3,5-bis(trifluoromethyl)benzoyl]-2-(1H-indol-3-ylmethyl)piperazine (210 mg) in ethyl acetate was added 4N hydrogen chloride in ethyl acetate solution (0.5 ml) and the whole was stirred at room temperature for 23 hours. The solution was evaporated in vacuo. The residue was triturated with a mixture of ethyl acetate and diisopropyl ether to give (2R)-4-[4-(4-fluorophenyl)-4-oxobutyl]-1-[3,5-bis(trifluoromethyl)benzoyl]-2-(1H-indol-3-ylmethyl) piperazine hydrochloride (183.7 mg).

mp: 161° C. (dec.); $[\alpha]_D^{25}$: −14.2° (C=0.5, MeOH); IR (Nujol): 3400–3150, 2650–2300, 1675, 1635, 1595, 1280–1250, 1275, 1125 cm$^{-1}$; NMR (DMSO-d$_6$, δ): 2.00–2.25 (2H, m), 3.05–5.20 (13H, m), 6.55–8.25 (12H, m), 10.95 (1H, s), 11.10–11.50 (1H, m); MASS: 620 (M+1) (free).

Preparation 6

Tetrahydrofuran (15 ml) was added to 70% solution of sodium bis(2-methoxyethoxy)aluminum hydride in toluene (49.7 g) under an atmosphere of nitrogen and then cooled. A solution of 4-morpholino-2-butyn-1-ol (3.0 g) in tetrahydrofuran (15 ml) was added dropwise maintaining the reaction temperature 4–5° C. After being stirred for 10 minutes, the reaction mixture was allowed to warm room temperature. After 1 hour, water (6 ml) and 10% aqueous sodium hydroxide solution (4.5 ml) were added cautiously and then filtered. The filtrate was dried over potassium carbonate and concentrated under reduced pressure to give an oily product, which was purified by column chromatography on silica gel using ethyl acetate-methanol (5:1) to afford (E)-4-morpholino-2-buten-1-ol (1.08 g).

IR (Neat): 3350, 1450, 1110, 990, 855 cm$^{-1}$; NMR (CDCl$_3$, δ): 2.48 (4H, t, J=4.7 Hz), 2.77 (1H, s), 3.02 (2H, d, J=5.4 Hz), 3.73 (4H, t, J=4.7 Hz), 4.15 (2H, d, J=4.0 Hz), 5.64–5.96 (2H, m); MASS: 158 (M+1).

Preparation 7

Thionyl chloride (0.96 ml) was added dropwise to a solution of (E)-4-morpholino-2-buten-1-ol (1.03 g) in dichloromethane (10 ml) at ice-bath temperature. After 3 hours, the reaction mixture was evaporated under reduced pressure and the resulting residue was triturated with ethyl acetate to give (E)-4-morpholino-2-butenyl chloride hydrochloride (0.98 g).

mp: 155–160° C.; IR (Nujol): 2750–2700, 1275, 1255, 1120, 1078, 1065, 975 cm$^{-1}$; NMR (DMSO-d$_6$, δ): 2.80–3.55 (4H, m), 3.64–4.10 (6H, m), 4.26 (2H, d, J=5.7 Hz), 5.90–6.25 (2H, m), 11.82 (1H, br s); MASS: 176 (M) (free).

EXAMPLE 50

A mixture of (2R)-1-[3,5-bis(trifluoromethyl)benzoyl]-2-(1H-indol-3-ylmethyl)piperazine (0.20 g), 5-morpholino-3-pentynyl chloride hydrochloride (0.175 g), potassium carbonate (0.303 g) and potassium iodide (10 mg) in dry acetonitrile (4 ml) was stirred under reflux for 60 hours. After removal of the solvent, the resulting residue was dissolved with ethyl acetate. The solution was washed with brine, dried over magnesium sulfate and evaporated under reduced pressure. The residue was purified by column chromatography on silica gel using toluene-ethyl acetate (1:2) as eluent and tread with 4N hydrogen chloride in ethyl acetate solution to give (2R-1-[3,5-bis(trifluoromethyl) benzoyl]-2-(1H-indol-3-ylmethyl)-4-(5-morpholino-3-pentynyl)piperazine dihydrochloride (0.174 g).

$[\alpha]_D^{21}$: −19.5° (C=0.5, MeOH); IR (Nujol): 3600–3150, 2700–2300, 1640, 1280, 1170, 1185 cm$^{-1}$; NMR (DMSO-d$_6$, δ): 2.90–5.20 (23H, m), 6.80–8.30 (8H, m), 10.95 (1H, s), 11.79 (2H, br s); MASS (APCI): 608 (M+2), 607 (M+1) (free); Anal. Calcd. for C$_{31}$H$_{32}$F$_6$N$_4$O$_2$.2HCl.1.5H$_2$O: C 52.70, H 5.28, N 7.93 Found: C 52.72, H 5.54, N 7.60.

EXAMPLE 51

To a mixture of (2R)-1-[3,5-bis(trifluoromethyl)benzoyl]-2-(3,4-dimethylbenzyl)piperazine (0.2 g), 1-methyl-4-formyl-1H-pyrazole (50 mg), and sodium triacetoxyborohydride (151 mg) in dichloromethane (2 ml) was added one drop of acetic acid. After being stirred at room temperature overnight, the solution was evaporated under reduced pressure. The resulting residue was partitioned between ethyl acetate and aqueous sodium hydrogen carbonate solution. The organic layer was separated, dried over magnesium sulfate and evaporated under reduced pressure. The residue was purified by column chromatography on silica gel using ethyl acetate-methanol as eluent and treated with 4N hydrogen chloride in ethyl acetate solution to give (2R)-1-[3,5-bis(trifluoromethyl)benzoyl]-2-(3,4-dimethylbenzyl)-4-[(1-methyl-1H-pyrazol-4-yl)methyl]piperazine hydrochloride (97 mg).

mp: 243–244° C.; $[\alpha]_D^{18.2}$: −16.8° (C=0.3, MeOH); IR (Nujol): 3350, 2750–2000, 1655, 1635, 1275, 1165, 1130 cm$^{-1}$; NMR (DMSO-d$_6$, δ): 1.97–2.28 (7H, m), 2.78–5.10 (13H, m), 6.50–8.30 (8H, m), 11.24–11.74 (1H, br m); MASS (APCI): 539 (M+1) (free); Anal. Calcd. for C$_{27}$H$_{28}$F$_6$N$_4$O.HCl.2.7H$_2$O: C 52.00, H 5.56, N 8.98 Found: C 51.82, H 5.15, N 8.99.

EXAMPLE 52

The following compounds were obtained according to a similar manner to that of Example 51.

(1) (2R)-1-[3,5-Bis(trifluoromethyl)benzoyl]-2-(3,4-dimethylbenzyl)-4-[(1-methyl-1H-imidazol-4-yl)methyl] piperazine Dihydrochloride $[\alpha]_D^{26}$: −11.80° (C=0.5, MeOH); IR (Neat): 3350, 2550, 1640, 1430, 1275, 1170, 1130 cm$^{-1}$; NMR (DMSO-d$_6$, δ): 2.07 (3H, s), 2.17 (3H, s), 2.72–5.10 (11H, m), 3.88 (3H, s), 6.60–9.08 (8H, m); MASS: 539 (M+1) (free).

(2) (2R)-1-[3,5-Bis(trifluoromethyl)benzoyl]-2-(3,4-dimethylbenzyl)-4-[(1-methyl-1H-imidazol-2-yl)methyl] piperazine Dihydrochloride $[\alpha]_D^{25}$: −12.10° (C=0.5, MeOH); IR (Neat): 3350, 2500, 1640, 1430, 1280, 1175, 1130 cm$^{-1}$; NMR (DMSO-d$_6$, δ):

2.07 (3H, s), 2.16 (3H, s), 2.53–5.14 (11H, m), 3.94 (3H, s), 6.47–8.26 (8H, m); MASS: 539 (M+1) (free).

EXAMPLE 53

The following compounds were obtained according to a similar manner to that of Example 43.

(1) (2R)-1-[3,5-Bis(trifluoromethyl)benzoyl]-2-(3,4-dimethylbenzyl)-4-(3-morpholinopropyl)piperazine Dihydrochloride mp: 220–230° C.; $[\alpha]_D^{21.5}$: −17.3° (C=0.3, MeOH); IR (Nujol): 3350, 2650, 1655, 1635, 1620, 1445, 1370, 1270 cm$^{-1}$; NMR (DMSO-d$_6$, δ): 1.92–5.22 (29H, m), 6.56–8.28 (6H, m), 11.43 (2H, br s); MASS (APCI): 572 (M+1) (free); Anal. Calcd. for $C_{29}H_{35}F_6N_3O_2$·2HCl: C 54.04, H 5.79, N 6.52 Found: C 53.72, H 5.80, N 6.29.

(2) (2R)-4-[2-[N,N-Bis(2-methoxyethyl)amino]ethyl]-1-[3,5-bis(trifluoromethyl)benzoyl]-2-(3,4-dimethylbenzyl)piperazine Dihydrochloride $[\alpha]_D^{22}$: −9.6° (C=0.5, MeOH); IR (Nujol): 3350, 2650, 1655, 1635, 1620, 1445, 1370, 1270 cm$^{-1}$; NMR (DMSO-d$_6$, δ): 1.92–5.22 (27H, m), 3.32 (6H, s), 6.56–8.28 (6H, m); MASS (APCI): 604 (M+1) (free); Anal. Calcd. for $C_{30}H_{39}F_6N_3O_3$·2HCl·1.6H$_2$O: C 51.08, H 6.32, N 5.96 Found: C 51.06, H 6.40, N 6.14.

(3) (2R)-1-[3,5-Bis(trifluoromethyl)benzoyl]-2-(1H-indol-3-ylmethyl)-4-[3-(1,2,3,6-tetrahydropyridin-1-yl)propyl]piperazine Dihydrochloride mp: >200° C.; $[\alpha]_D^{23}$: −2.30° (C=0.5, MeOH); IR (Nujol): 3500–3100, 2700–2400, 1630 cm$^{-1}$; NMR (DMSO-d$_6$, δ): 2.20–4.20 (21H, m), 5.72 (1H, d, J=10.2 Hz), 5.93 (1H, d, J=10.2 Hz), 6.55–8.23 (8H, m), 10.95 (1H, br s); MASS (APCI): 579 (M+1) (free); Anal. Calcd. for $C_{30}H_{32}F_6N_4O$·2HCl·2H$_2$O: C 52.41, H 5.57, N 8.15 Found: C 52.03, H 5.77, N 7.72.

(4) (2R)-4-[3-(3-Azabicyclo[3.2.2]non-3-yl)propyl]-1-[3,5-bis(trifluoromethyl)benzoyl]-2-(3,4-dichlorobenzyl)piperazine Dihydrochloride mp: 150° C. (dec.); $[\alpha]_D^{19.1}$: −2.90° (C=0.5, MeOH); IR (Nujol): 3500–3100, 2700–2400, 1630 cm$^{-1}$; NMR (DMSO-d$_6$, δ): 1.60–3.90 (29H, m), 6.90–8.30 (6H, m); MASS (APCI): 652 (M+2), 650 (M+1) (free); Anal. Calcd. for $C_{31}H_{35}Cl_2F_6N_3O$·2HCl·H$_2$O: C 50.22, H 5.30, N 5.67 Found: C 50.25, H 5.60, N 5.32.

(5) (2R)-1-[3,5-Bis(trifluoromethyl)benzoyl]-2-(3,4-dichlorobenzyl)-4-[3-(4,1'-bipiperidin-1-yl)propyl]piperazine Trihydrochloride mp: >200° C.; $[\alpha]_D^{28.4}$: −3.40° (C=0.5, MeOH); IR (Nujol): 3300, 2700–2400, 1630, 1450 cm$^{-1}$; NMR (DMSO-d$_6$, δ): 1.60–3.90 (34H, m), 6.90–8.30 (6H, m); MASS (FAB): 693 (M+1), 695 (free); Anal. Calcd. for $C_{33}H_{40}Cl_2F_6N_4O$·3HCl: C 49.36, H 5.40, N 6.98 Found: C 49.81, H 5.75, N 6.75.

EXAMPLE 54

A solution of (2R)-1-[3,5-bis(trifluoromethyl)benzoyl]-2-(3,4-dimethylbenzyl)-4-(4-morpholino-2-butynyl)piperazine (141 mg) in methanol (10 ml) was hydrogenated over 10% Pd—C (50 mg) at room temperature under 2–3 atoms. After removal of the catalyst by filtration, the filtrate was concentrated under reduced pressure. The residue was purified by column chromatography on silica gel using dichloromethane-methanol as eluent and treated with 4N hydrogen chloride in ethyl acetate solution to give (2R)-1-[3,5-bis(trifluoromethyl)benzoyl]-2-(3,4-dimethylbenzyl)-4-(4-morpholinobutyl)piperazine dihydrochloride (106 mg).

mp: 279° C.; $[\alpha]_D^{23}$: −13.5° (C=0.5, MeOH); IR (Nujol): 3300, 2700–2400, 1645, 1500, 1445, 1370, 1270, 1170 cm$^{-1}$; NMR (DMSO-d$_6$, δ): 1.70–5.22 (31H, m), 6.56–8.28 (6H, m), 11.00–11.40 (2H, m); MASS (APCI): 586 (M+1) (free).

EXAMPLE 55

The following compound was obtained according to a similar manner to that of Example 54.

(2R)-1)[3,5-Bis(trifluoromethyl)benzoyl]-2-(1H-indol-3-ylmethyl)-4-(5-morpholinopentyl)piperazine Dihydrochloride $[\alpha]_D^{21}$: −6.10° (C=0.5, MeOH); IR (Neat): 3400–3200, 2700–2400, 1640, 1430 cm$^{-1}$; NMR (DMSO-d$_6$, δ): 1.50–5.20 (27H, m), 6.60–8.30 (8H, m), 10.80–11.50 (3H, m); MASS: 611 (M+1) (free); Anal. Calcd. for $C_{31}H_{36}F_6N_4O_2$·2HCl·1.3H$_2$O: C 52.67, H 5.79, N 7.92 Found: C 52.66, H 6.13, N 7.76.

EXAMPLE 56

A solution of (2R)-1-[3,5-bis(trifluoromethyl)benzoyl]-2-(3,4-dimethylbenzyl)-4-(5-morpholino-3-pentynyl)piperazine (200 mg) was treated with 4N hydrogen chloride in ethyl acetate solution to give (2R)-1-[3,5-bis(trifluoromethyl)benzoyl]-2-(3,4-dimethylbenzyl)-4-(5-morpholino-3-pentynyl)piperazine Dihydrochloride.

$[\alpha]_D^{21}$: −25.2° (C=0.5, MeOH); IR (Neat): 3700–3100, 2920, 2750–2250, 1635, 1500, 1430, 1275, 1170, 1120 cm$^{-1}$; NMR (DMSO-d$_6$, δ): 2.05–2.20 (6H, m), 2.75–5.15 (23H, m), 6.65–8.28 (6H, m), 11.60–12.20 (2H, m); MASS: 596 (M+1) (free); Anal. Calcd. for $C_{31}H_{35}F_6N_3O_2$·2HCl·1.5H$_2$O: C 53.53, H 5.80, N 6.04 Found: C 53.47, H 6.14, N 5.91.

EXAMPLE 57

(2R)-1-[3,5-Bis(trifluoromethyl)benzoyl]-2-(3,4-dimethylbenzyl)piperazine fumarate (9.13 g) was treated wit aqueous 10% sodium hydroxide solution (65 ml) and dichloromethane (65 ml). The organic layer was separated, washed with brine, dried over magnesium sulfate and evaporated under reduced pressure. A mixture of (2R)-1-[3,5-bis(trifluoromethyl)benzoyl]-2-(3,4-dimethylbenzyl)piperazine obtained by the above procedure, potassium carbonate (3.60 g) and 1,4-dichloro-2-butyne (1.9 ml) in N,N-dimethylformamide (72 ml) was stirred for 4.5 hours at room temperature. The mixture was poured into water (360 ml) and extracted with ethyl acetate. The extract was washed with brine, dried over magnesium sulfate and evaporated under reduced pressure. The residue was purified by column chromatography on silica gel using toluene-ethyl acetate as eluent to give (2R)-1-[3,5-bis(trifluoromethyl)benzoyl]-2-(3,4-dimethylbenzyl)-4-(4-chloro-2-butynyl)piperazine (4.86 g).

IR (Neat): 1706, 1635, 1503, 1275, 1125 cm$^{-1}$; NMR (CDCl$_3$, δ):2.05–5.20 (19H, m), 6.60–7.84 (6H, m); MASS (APCI): 531 (M+1).

EXAMPLE 58

A mixture of (2R)-1-[3,5-bis(trifluoromethyl)benzoyl]-2-(3,4-dimethylbenzyl)-4-(4-chloro-2-butynyl)piperazine (0.49 g), 3-methylmorpholine hydrochloride (0.15 g), potassium carbonate (0.39 g) and potassium iodide (10 mg) in dry N,N-dimethylformamide (5 ml) was stirred for 5 hours at room temperature. The mixture was poured into water and extracted with ethyl acetate. The extract was washed with brine, dried over magnesium sulfate and evaporated under reduced pressure. The residue was purified by column chromatography on silica gel using ethyl acetate as eluent and treated with 4N hydrogen chloride in ethyl acetate solution to give (2R)-1-[3,5-bis(trifluoromethyl)benzoyl]-2-(3,4-dimethylbenzyl)-4-[4-(3-methylmorpholino)-2-butynyl]piperazine dihydrochloride (0.28 g).

mp: 150–160° C.; $[\alpha]_D^{28.4}$: −5.71° (C=1.0, MeOH); IR (Nujol): 3300, 2700–2400 1650, 1430 cm$^{-1}$; NMR (DMSO-d$_6$, δ): 1.20–5.22 (29H, m), 6.60–8.20 (6H, m), 12.20–12.40 (2H, m); MASS (APCI): 596 (M+1) (free); Anal. Calcd. for C$_{31}$H$_{35}$F$_6$N$_3$O$_2$.2HCl.1.7H$_2$O: C 53.25, H 5.82, N 6.01 Found: C 53.28, H 5.97, N 5.80.

EXAMPLE 59

The following compounds were obtained according to a similar manner to that of Example 58.

(1) (2R)-1-[3,5-Bis(trifluoromethyl)benzoyl]-2-(3,4-dimethylbenzyl)-4-[4-(2-methoxymethylmorpholino)-2-butynyl]piperazine Dihydrochloride mp: 150–165° C.; $[\alpha]_D^{28.4}$: −8.86° (C=0.7, MeOH); IR (Nujol): 3300 2700–2400, 1640, 1430 cm$^{-1}$; NMR (DMSO-d$_6$, δ): 2.00–5.22 (28H, m), 3.25 (3H, s), 6.50–8.20 (6H, m), 12.20–12.40 (2H, m); MASS (APCI): 626 (M+1) (free); Anal. Calcd. for C$_{32}$H$_{37}$F$_6$N$_3$O$_3$.2HCl.H$_2$O: C 53.64, H 5.77, N 5.86 Found: C 53.60, H 5.94, N 5.67.

(2) (2R)-1-[3,5-Bis(trifluoromethyl)benzoyl]-2-(3,4-dimethylbenzyl)-4-[4-(2-fluoromethylmorpholino)-2-butynyl]piperazine Dihydrochloride mp: 175–180° C.; $[\alpha]_D^{28.4}$: −8.75° (C=0.7, MeOH); IR (Nujol): 3300, 2700–2400, 1635, 1500 cm$^{-1}$; NMR (DMSO-d$_6$, δ): 2.00–5.22 (28H, m), 6.50–8.20 (6H, m); MASS (APCI): 614 (M+1) (free); Anal. Calcd. for C$_{31}$H$_{34}$F$_7$N$_3$O$_2$.2HCl.H$_2$O: C 52.85, H 5.44, N 5.96 Found: C 52.82, H 5.45, N 5.74.

(3)(2R)-1-[3,5-Bis(trifluoromethyl)benzoyl]-2-(3,4-dimethylbenzyl)-4-[4-(3,3-dimethylmorpholino)2-butynyl]piperazine Dihydrochloride mp: 180–190° C.; $[\alpha]_D^{28.3}$: −7.24° (C=1.05, MeOH); IR (Nujol): 3300, 2700–2400, 1635 cm$^{-1}$; NMR (DMSO-d$_6$, δ): 1.30–1.40 (6H, m), 2.00–5.22 (25H, m), 6.60–8.20 (6H, m), 12.05–12.20 (2H, m); MASS (APCI): 610 (M+1H) (free); Anal. Calcd. for C$_{32}$H$_{37}$F$_6$N$_3$O$_2$.2HCl.2.5H$_2$O: C 52.82, H 6.09, N 5.68 Found: C 52.84, H 5.89, N 5.78.

(4) (2R)-1-[3,5-Fix(trifluoromethyl)benzoyl]-2-(3,4-dimethylbenzyl)-4-[4-((2S)-2-methoxymethylpyrrolidino)-2-butynyl]piperazine Dihydrochloride mp: 195–197° C.; $[\alpha]_D^{28.4}$: −19.79° (C=0.7, MeOH); IR (Nujol): 3450, 2700–2400, 1640, 1450 cm$^{-1}$; NMR (DMSO-d$_6$, δ): 2.00–5.22 (28H, m) 3.32 (3H, s), 6.50–8;.20 (6H, m), 11.50–11.70 (2H, m); MASS (APCI): 610 (M+1) (free); Anal. Calcd. for C$_{32}$H$_{37}$F$_6$N$_3$O$_2$.2HCl.2H$_2$O: C 53.49, H 6.03, N 5.85 Found: C 53.66, H 5.73, N 5.82.

(5) (2R)-1-[3,5-Bis(trifluoromethyl)benzoyl]-2-(3,4-dimethylbenzyl)-4-[4-(3-methoxymethylmorpholino)-2-butynyl]piperazine Dihydrochloride mp: 140–155° C.; $[\alpha]_D^{28.4}$: −7.22° (C=0.63, MeOH); IR (Nujol): 3300, 2700–2400, 1635, 1440 cm$^{-1}$; NMR (DMSO-d$_6$, δ): 2.00–5.22 (28H, m), 3.32 (3H, s), 6.50–8.20 (6H, m); MASS (APCI): 626 (M+1) (free); Anal. Calcd. for C$_{32}$H$_{37}$F$_6$N$_3$O$_3$.2HCl: C 52.32, H 5.90, N 5.72 Found: C 52.35, H 6.11, N 5.43.

EXAMPLE 60

A mixture of (2R)-1-[3,5-bis(trifluoromethyl)benzoyl]-2-(3,4-dimethylbenzyl)piperazine (0.38 g) potassium carbonate (0.42 g), 3-(3-pyridyl)-2-propynyl chloride hydrochloride (1.9 ml) and small amount of potassium iodide in N,N-dimethylformamide (10 ml) was stirred for 2 hours at 40° C. The mixture was poured into water and extracted with ethyl acetate. The extract was washed with brine, dried over magnesium sulfate and evaporated under reduced pressure. The residue was purified by column chromatography on silica gel using ethyl acetate as eluent and treated with 4N hydrogen chloride in ethyl acetate solution to give (2R)-1-[3,5-bis(trifluoromethyl)benzoyl]-2-(3,4-dimethylbenzyl)-4-[3-(3-pyridyl)-2-propynyl]piperazine dihydrochloride (0.26 g).

mp: 140–150° C., $[\alpha]_D^{28.4}$: −10.13° (C=0.8, MeOH); IR (Nujol): 3300, 2700–2400, 1630, 1450 cm$^{-1}$; NMR (DMSO-d$_6$, δ): 2.00–5.22 (17H, m), 6.50–8.20 (8H, m), 8.70–8.85 (2H, m); MASS (APCI): 560 (M+1) (free); Anal. Calcd. for C$_{30}$H$_{27}$F$_6$N$_3$O.2HCl.2.8H$_2$O: C 52.76, N 5.11, N 6.15 Found: C 52.74, N 4.96, N 6.05.

EXAMPLE 61

A mixture of (2R)-1-[3,5-bis(trifluoromethyl)benzoyl]-4-[(E)-4-chloro-2-butenyl]-2-(2-naphthylmethyl)piperazine (300 mg), thiomorpholine (0.054 ml) and powdered potassium carbonate (100 mg) in dry acetonitrile (3 ml) was heated at 50° C. for 10 hours. Additional potassium carbonate (100 mg) and thiomorpholine (0.054 ml) were added and then the resulting mixture was further heated at the same temperature. After 2 hours, the reaction mixture was cooled and then filtered. The filtrate was concentrated under reduced pressure and the resulting residue was purified by column chromatography on silica gel using a mixture of dichloromethane and methanol (40:1). The obtained product was dissolved in ethyl acetate and treated with 4N hydrogen chloride in ethyl acetate (0.6 ml) to give (2R)-1-[3,5-bis(trifluoromethyl)benzoyl]-2-(2-naphthylmethyl)-4-((E)-4-thiomorpholino-2-butenyl)piperazine dihydrochloride (190 mg).

mp: >230° C.; $[\alpha]_D^{28.9}$: −14.50° (C=0.5, MeOH); IR (Nujol): 3650–3100, 2410, 1640, 1274, 1130 cm$^{-1}$; NMR (DMSO-d$_6$, δ): 2.55–5.30 (21H, m), 6.00–6.30 (2H, m), 7.00–8.20 (10H); MASS: 622 (M+1) (free).

EXAMPLE 62

The following compounds were obtained according to a similar manner to that of Example 61.

(1) (2R)-1-[3,5-Bis(trifluoromethyl)benzoyl]-2-(2-naphthylmethyl)-4-[(E)-4-morpholino-2-butenyl]piperazine Dihydrochloride mp: >230° C.; $[\alpha]_D^{28.7}$: −16.60° (C=0.5, MeOH); IR (Nujol): 3600–3100, 2450, 1639, 1273, 1130 cm$^{-1}$; NMR (DMSO-d$_6$, δ): 2.80–5.30 (21H, m), 6.10–6.30 (2H, m), 7.00–8.25 (10H, m); MASS: 606 (M+1) (free).

(2) (2R)-2-[3,5-Bis(trifluoromethyl)benzoyl]-2-(3,4-dimethylbenzyl)-4-[(E)-4-thiomorpholino-2-butenyl]piperazine Dihydrochloride mp: >230° C.; $[\alpha]_D^{25.8}$: 5.20° (C=0.25, DMSO); IR (Nujol): 3600–3100, 2450, 1642, 1274, 1130 cm$^{-1}$; NMR (DMSO-d$_6$, δ): 2.10–5.10 (27H, m), 5.90–6.30 (2H), m), 6.65–7.05 (3H, m), 7.57 (2H, s), 8.05 (1H, s); MASS: 600 (M+1) (free).

EXAMPLE 63

A mixture of (2R)-1-[3,5-bis(trifluoromethyl)benzoyl]-4-[(E)-4-chloro-2-butenyl]-2-(3,4-dimethylbenzyl)piperazine (450 mg), 3,3-dimethylmorpholine hydrochloride (130 mg) and powdered potassium carbonate (350 mg) in dry acetonitrile (5 ml) was heated at reflux temperature for 3 hours. Additional potassium carbonate (350 mg) and 3,3- dimethylmorpholine hydrochloride (130 mg) were added and then the resulting mixture was further heated at reflux temperature. After 6 hours, the reaction mixture was cooled and then filtered. The filtrate was concentrated under reduced pressure and the resulting residue was purified by column chromatography on silica gel using a mixture of dichloromethane and methanol (50:1). The obtained product was dissolved in ethyl acetate and treated with 4N hydrogen chloride in ethyl acetate solution to give (2R)-1-[3,5-bis (trifluoromethyl)benzoyl]-2-(3,4-dimethylbenzyl)-4-[(E)-4-(3,3-dimethylmorpholino)-2-butenyl]piperazine dihydrochloride (370 mg).

mp: >230° C.; $[\alpha]_D^{25.5}$: −11.70° (C=0.5, MeOH); IR (Nujol): 3400, 2450, 1639, 1274, 1130 cm$^{-1}$; NMR (DMSO-d$_6$, δ): 1.34–1.40 (6H, m), 2.10–2.18 (6H, m), 2.70–5.20 (19H, m), 6.10–6.30 (2H, m), 6.65–6.30 (6H, m), 11.20–12.00 (2H, m); MASS: 612 (M+1) (free).

EXAMPLE 64

A mixture of (2R)-1-[3,5-bis(trifluoromethyl)benzoyl]-2-(3,4-dimethylbenzyl)piperazine (1.0 g), (E)-1,4-dichloro-2-butene (0.31 ml) and powdered potassium carbonate (0.4 g) in dry acetonitrile (10 ml) was heated at 50° C. After 4 hours, the reaction mixture was cooled and then filtered. The filtrate was concentrated under reduced pressure and the resulting residue was purified by column chromatography on silica gel using a mixture of toluene and ethyl acetate (4:1) to give (2R)-1-[3,5-bis(trifluoromethyl)benzoyl]-2-(3,4-dimethylbenzyl)-4-[(E)-4-chloro-2-butenyl]piperazine (0.53 g) as an oil.

IR (Neat): 3460, 1638, 1272, 1125, 900 cm$^{-1}$; NMR (CDCl$_3$, δ): 2.00–5.20 (19H, m), 5.75–6.00 (2H, m), 6.60–8.00 (6H, m); MASS: 533 (M+1).

EXAMPLE 65

The following compound was obtained according to a similar manner to that of Example 64.
(2R)-1-[3,5-Bis(trifluoromethyl)benzoyl]-2-(2-naphthylmethyl)-4-[(E)-4-chloro-2-butenyl]piperazine IR (Neat): 1637, 1273, 1128, 900 cm$^{-1}$; NMR (CDCl$_3$, δ): 2.05–5.20 (13H, m), 5.80–6.00 (2H, m), 7.10–8.10 (10H, m); MASS: 555 (M+1).

EXAMPLE 66

A mixture of (2R)-1-[3,5-bis(trifluoromethyl)benzoyl]-2-(1H-indol-3-ylmethyl)-4-(3-methylsulfonyloxypropyl) piperazine (150 mg), 4-aminomorpholine (36 mg) and triethylamine (52 mg) in dry methanol (5 ml) was refluxed for 2 hours. The reaction mixture was concentrated under reduced pressure and the resulting residue was partitioned between ethyl acetate and aqueous sodium hydrogen carbonate solution. The organic layer was washed with brine and dried over magnesium sulfate. After evaporation of the solvent, the residue was purified by column chromatography on silica gel using a mixture of ethyl acetate and methanol (10:1) to afford an oily product, which was treated with 4N hydrogen chloride in ethyl acetate solution (0.5 ml) to give (2R)-1-[3,5-bis(trifluoromethyl)benzoyl]-2-(1H-indol-3-ylmethyl)-4-[3-(morpholinoamino)propyl]piperazine dihydrochloride (58 mg).

$[\alpha]_D^{23}$: −3.60° (C=0.5, MeOH); IR (Nujol): 3300, 2500, 1630, 1420, 1275 cm$^{-1}$; NMR (DMSO-d$_6$, δ): 2.00–5.24 (23H, m), 6.60–8.28 (8H, m), 10.94 (1H, s), 11.50 (1H, br s); MASS: 598 (M+1) (free).

EXAMPLE 67

The following compounds were obtained according to a similar manner to that of Example 66.

(1) (2R)-1-[3,5-Bis(trifluoromethyl)benzoyl]-2-(1H-indol-3-ylmethyl)-4-[2-(cis-2,6-dimethylmorpholino)ethyl] piperazine Dihydrochloride $[\alpha]_D^{20}$: −2.60° (C=0.5, MeOH); IR (Nujol): 3350, 2600, 1640, 1280, 1175, 1130 cm$^{-1}$; NMR (DMSO-d$_6$, δ): 1.55 (6H, m), 2.52–5.20 (19H, m), 6.60–8.24 (8H, m), 10.95 (1H, s); MASS: 597 (M+1) (free).

(2) (2R)-1-[3,5-Bis(trifluoromethyl)benzoyl]-2-(1H-indol-3-ylmethyl)-4-[3-(cis-2,6-dimethylmorpholino)propyl] piperazine Dihydrochloride $[\alpha]_D^{20}$: −5.30° (C=0.5, MeOH); IR (Nujol): 3350, 2600, 1640, 1280 cm$^{-1}$; NMR (DMSO-d$_6$, δ): 1.20 (6H, m), 2.08–5.20 (21H, m), 6.63–8.33 (8H, m), 10.94 (1H, s); MASS: 611 (M+1) (free).

(3) (2R)-1-[3,5-Bis(trifluoromethyl)benzoyl]-2-(3,4-dimethylbenzyl)-4-[2-(1-imidazolyl)ethyl]piperazine Dihydrochloride $[\alpha]_D^{21}$: −16.20° (C=0.5, MeOH); IR (Nujol): 3350, 2700, 2575, 1640, 1430, 1280, 1170, 1130 cm$^{-1}$; NMR (DMSO-d$_6$, δ): 2.04–5.20 (13H, m), 2.09 (3H, s), 2.18 (3H, s), 6.55–8.22 (8H, m), 9.29 (1H, s); MASS: 539 (M+1) (free).

(4) (2R)-1-[3,5-Bis(trifluoromethyl)benzoyl]-2-(3,4-dimethylbenzyl)-4-[3-(morpholinoamino)propyl]piperazine Dihydrochloride $[\alpha]_D^{20}$: −14.10° (C=0.5, MeOH); IR (Nujol): 3350, 2550, 1640, 1430, 1280 cm$^{-1}$; NMR (DMSO-d$_6$, δ): 1.97–5.14 (23H, m), 2.10 (3H, s), 2.18 (3H, s), 6.64–8.24 (6H, m), 10.92 (1H, br s); MASS: 587 (M+1) (free).

(5) (2R)-1-[3,5-Bis(trifluoromethyl)benzoyl]-2-(3,4-dimethylbenzyl)-4-[2-(3-pyridylmethylamino)ethyl] piperazine Trihydrochloride $[\alpha]_D^{21}$: 3.50° (C=0.5, MeOH); IR (Nujol): 3400, 2600, 1640, 1430, 1280, 1170, 1130 cm$^{-1}$; NMR (DMSO-d$_6$, δ): 2.07–5.20 (13H, m), 2.10 (3H, s), 2.18 (3H, s), 4.50 (2H, s), 6.60–9.09 (10H, m), 10.32 (1H, br s); MASS: 579 (M+1) (free).

(6) (2R)-1-[3,5-Bis(trifluoromethyl)benzoyl]-2-(3,4-dimethylbenzyl)-4-(2-homomorpholinoethyl)piperazine Dihydrochloride $[\alpha]_D^{17}$: −9.90° (C=0.5, MeOH); IR (Nujol): 3400, 2600, 2450, 1640, 1430, 1280 cm$^{-1}$; NMR (DMSO-d$_6$, δ): 2.04–5.17 (23H, m), 2.10 (3H, s), 2.18 (3H, s), 6.62–8.26 (6H, m); MASS: 572 (M+1) (free).

(7) (2R)-1-[3,5-Bis(trifluoromethyl)benzoyl]-2-(3,4-dimethylbenzyl)-4-(3-homomorpholinopropyl)piperazine Dihydrochloride $[\alpha]_D^{19}$: −10.0° (C=0.5, MeOH); IR (Nujol): 3400, 2600, 1635, 1430, 1280 cm$^{-1}$; NMR (DMSO-d$_6$, δ): 1.73–5.20 (25H, m), 2.10 (3H, s), 2.18 (3H, s), 6.62–8.24 (6H, m); MASS: 586 (M+1) (free).

(8) (2R)-1-[3,5-Bis(trifluoromethyl)benzoyl]-2-(1H-indol-3-ylmethyl)-4-(3-homomorpholinopropyl)piperazine Dihydrochloride $[\alpha]_D^{17}$: −5.50° (C=0.5, MeOH); IR (Nujol): 3300, 2650, 1640, 1275 cm$^{-1}$; NMR (DMSO-d$_6$, δ): 1.90–5.23 (25H, m), 6.62–8.34 (8H, m), 10.95 (1H, s); MASS: 597 (M+1) (free).

(9) (2R)-1-[3,5-Bis(trifluoromethyl)benzoyl]-2-(3,4-dichlorobenzyl)-4-[3-(4-acetylpiperidino)propyl]piperazine Dihydrochloride $[\alpha]_D^{20}$: 2.20° (C=0.5, MeOH); IR (Nujol): 3350, 2650, 1700, 1630, 1275 cm$^{-1}$; NMR (DMSO-d$_6$, δ): 1.69–5.21 (24H, m), 2.16 (3H, s), 6.97–8.36 (6H, m); MASS: 652 (M) (free).

(10) (2R)-1-[3,5-Bis(trifluoromethyl)benzoyl]-2-(3,4-dimethylbenzyl)-4-[3-(4-acetylpiperidino)propyl]piperazine Dihydrochloride $[\alpha]_D^{20}$: −11.30° (C=0.5, MeOH); IR (Nujol): 3425, 3375, 2500, 1705, 1640, 1275 cm$^{-1}$; NMR (DMSO-d$_6$, δ):

1.67–5.20 (24H, m), 2.16 (6H, s), 2.18 (3H, s), 6.62–8.25 (6H, m), 10.60 (1H, br s), 11.49 (1H, br s); MASS: 612 (M+1) (free).

(11) (2R)-1-[3,5-Bis(trifluoromethyl)benzoyl]-2-(3,4-dichlorobenzyl)-4-(2-morpholinoethyl)piperazine Dihydrochloride $[\alpha]_D^{20}$: 6.10° (C=0.5, MeOH); IR (Nujol): 3350, 2600, 1630, 1270 cm$^{-1}$; NMR (DMSO-d$_6$, δ): 2.14–5.16 (21H, m), 6.93–8.27 (6H, m); MASS: 598 (M) (free).

(12) (2R)-1-[3,5-Bis(trifluoromethyl)benzoyl]-2-(1H-indol-3-ylmethyl)-4-[3-(4-methoxypiperidino)propyl]piperazine Dihydrochloride $[\alpha]_D^{19}$: −6.70° (C=0.5, MeOH); IR (Nujol): 3300, 2550, 1625, 1270 cm$^{-1}$; NMR (DMSO-d$_6$, δ): 1.57–5.20 (24H, m), 3.27 (3H, s), 6.60–8.28 (8H, m), 10.95 (1H, s); MASS: 611 (M+1) (free).

(13) (2R)-1-[3,5-Bis(trifluoromethyl)benzoyl]-2-(3,4-dimethylbenzyl)-4-[2-[N-(2-methoxyethyl)-N-methylamino]ethyl]piperazine Dihydrochloride mp: 222° C. (dec.); $[\alpha]_D^{23}$: −12.50° (C=0.5, MeOH); IR (Nujol): 3380, 2400, 1644, 1275, 1130 cm$^{-1}$; NMR (DMSO-d$_6$, δ): 2.0–2.3 (7H, m), 2.88 (3H, s), 3.33 (3H, s), 2.3–5.3 (18H, m), 6.6–8.3 (6H, m); MASS: 560 (M+1) (free).

(14) (2R)-1-[3,5-Bis(trifluoromethyl)benzoyl]-2-(3,4-dimethylbenzyl)-4-[3-(hexamethyleneimino)propyl]piperazine Dihydrochloride $[\alpha]_D^{26}$: −11.70° (C=0.5, MeOH); IR (Neat): 3400, 2600, 1640, 1430, 1280 cm$^{-1}$; NMR (DMSO-d$_6$, δ): 1.49–5.20 (27H, m), 2.10 (3H, s), 2.19 (3H, s), 6.67–8.23 (6H, m); MASS: 584 (M+1) (free).

(15) (2R)-1-[3,5-Bis(trifluoromethyl)benzoyl]-2-(3,4-dimethylbenzyl)-4-[2-(4-pyridylmethylamino)ethyl]piperazine Trihydrochloride $[\alpha]_D^{25}$: −0.20° (C=0.5, MeOH); IR (Neat): 3400, 2600, 1640, 1430, 1280, 1175, 1130 cm$^{-1}$; NMR (DMSO-d$_6$, δ): 2.10 (3H, s), 2.18 (3H, s), 2.64–5.20 (13H, m), 4.16 (2H, s), 6.40–8.97 (10H, m); MASS: 579 (M+1) (free).

(16) (2R)-1-[3,5-Bis(trifluoromethyl)benzoyl]-2-(3,4-dimethylbenzyl-4-[3-(1,2,4-triazol-3-ylamino)propyl]piperazine Dihydrochloride $[\alpha]_D^{24}$: −10.50° (C=0.5, MeOH); IR (Neat): 3075, 2700, 1675, 1640, 1430, 1280, 1170, 1130 cm$^{-1}$; NMR (DMSO-d$_6$, δ): 2.05–5.20 (15H, m), 2.09 (3H, s), 2.18 (3H, s), 6.60–8.34 (9H, m); MASS: 569 (M+1) (free).

EXAMPLE 68

A mixture of (2R)-1-[3,5-bis(trifluoromethyl)benzoyl]-2-(2-naphthylmethyl)piperazine (300 mg), 4-thiomorpholino-2-butynyl chloride hydrochloride (170 mg) and powdered potassium carbonate (210 mg) in dry acetonitrile (3 ml) was refluxed for 7.5 hours in the presence of potassium iodide (20 mg). The reaction mixture was cooled and then filtered. The filtrate was concentrated under reduced pressure and the resulting residue was purified by column chromatography on silica gel using a mixture of ethyl acetate and methanol (50:1). The obtained product was dissolved in ethyl acetate and treated with 4N hydrogen chloride in ethyl acetate solution (0.6 ml) to give (2R)-1-[3,5-bis(trifluoromethyl) benzoyl]-2-(2-naphthylmethyl)-4-(4-thiomorpholino-2-butynyl)piperazine dihydrochloride (300 mg).

mp: 152–156° C. $[\alpha]_D^{27}$: −47.30° (C=0.5, MeOH); IR (Nujol): 3350, 2500, 1637, 1275, 1125 cm$^{-1}$; NMR (DMSO-d$_6$, δ): 2.70–5.30 (21H, m), 7.00–8.20 (10H, m); MASS: 620 (M+1) (free).

EXAMPLE 69

A mixture of (2R)-1-[3,5-bis(trifluoromethyl)benzoyl]-2-(3,4-dimethylbenzyl)-4-(4-chloro-2-butynyl)piperazine (200 mg), 1-cyclohexylpiperazine (63 mg) and powdered potassium carbonate (210 mg) in dry N,N-dimethylformamide (2 ml) was stirred for 12 hours at room temperature. Additional 1-cyclohexylpiperazine (25 mg) was added and after 2 hours the reaction mixture was poured into water (20 ml) and extracted with ethyl acetate. The organic layer was washed with brine and dried over magnesium sulfate. After evaporation of the solvent, the resulting residue was purified by column chromatography on silica gel using a mixture of dichloromethane and methanol (30:1). The obtained product was dissolved in ethyl acetate and treated with 4N hydrogen chloride in ethyl acetate solution (0.6 ml) to give (2R)-1-[3,5-bis(trifluoromethyl) benzoyl]-2-(3,4-dimethylbenzyl)-4-[4-(4-cyclohexylpiperazin-1-yl)-2-butynyl]piperazine trihydrochloride (220 mg).

mp: 175–190° C., $[\alpha]_D^{25.2}$: −7.20° (C=0.5, MeOH); IR (Nujol): 3370, 2750–1920, 1635, 1276, 1126 cm$^{-1}$; NMR (DMSO-d$_6$, δ): 1.02–5.20 (38H, m), 6.60–8.30 (6H, m); MASS: 664 (M+1) (free).

EXAMPLE 70

Potassium carbonate (187 mg) and 2-(chloromethyl) pyridine hydrochloride (81 mg) were added to a solution of (2R)-1-[3,5-bis(trifluoromethyl)benzoyl]-2-(3,4-dimethylbenzyl)piperazine (200 mg) in N,N-dimethylformamide (4 ml) at room temperature with stirring. After 2 hours, the reaction mixture was poured into water (50 ml) and extracted with ethyl acetate. The organic layer was washed with water and then dried over magnesium sulfate, and evaporated under reduced pressure. The obtained residue was purified by column chromatography on silica gel using a mixture of ethyl acetate and toluene (1:3) and treated with 4N hydrogen chloride in ethyl acetate solution to afford (2R)-1-[3,5-bis(trifluoromethyl)benzoyl]-2-(3,4-dimethylbenzyl)-4-(2-pyridylmethyl)piperazine dihydrochloride (123 mg).

$[\alpha]_D^{23}$: −28.30° (C=0.5, MeOH); IR (Nujol): 3360, 2560, 1640, 1278, 1130 cm$^{-1}$; NMR (DMSO-d$_6$, δ): 2.0–2.3 (10H, m), 2.6–5.8 (9H, m), 6.6–8.7 (10H, m); MASS: 536 (M+1) (free).

EXAMPLE 71

Lindlar catalyst (Pd—CaCO$_3$—Pb(OAc)$_2$) (40 mg) was added to a solution of (2R)-1-[3,5-bis(trifluoromethyl) benzoyl]-2-(1H-indol-3-ylmethyl)-4-(4-morpholino-2-butynyl)piperazine in methanol (8 ml). The mixture was stirred for 2 hours under hydrogen at 25° C. and then filtered. The filtrate was concentrated under reduced pressure and the resulting residue was chromatographed on silica gel with dichloromethane-methanol (20:1) as eluent to give material which on treatment with 4N hydrogen chloride in ethyl acetate solution afforded (2R)-1-[3,5-bis(trifluoromethyl) benzoyl]-2-(1H-indol-3-ylmethyl)-4-[(Z)-4-morpholino-2-butenyl]piperazine dihydrochloride (104 mg).

$[\alpha]_D^{21}$: +0.40° (C=0.5, MeOH); IR (Nujol): 3700–3150, 2750–2300, 1635, 1275, 1170, 1120 cm$^{-1}$; NMR (DMSO-d$_6$, δ): 3.00–4.10 (21H, m), 6.05–6.35 (2H, m), 6.80–8.10 (8H, m), 10.72 (1H, s); MASS: 595 (M+1) (free).

EXAMPLE 72

The following compound was obtained according to a similar manner to that of Example 71.

(2R)-1-[3,5-Bis(trifluoromethyl)benzoyl]-2-(3,4-dimethylbenzyl)-4-[(Z)-4-morpholino-2-butenyl]piperazine Dihydrochloride mp: 243–246° C.; $[\alpha]_D^{21}$: −5.30° (C=0.5, MeOH); IR (Nujol): 3600–3150, 2600–2300, 1645, 1275, 1170, 1130 cm$^{-1}$; NMR (DMSO-d$_6$, δ): 2.10–2.20 (6H, m), 3.0–4.2 (21H, m), 6.05–6.35 (2H, m), 6.80–7.10 (3H, m), 7.60 (2H, s), 8.09 (1H, s); The NMR spectrum of this compound was measured at 90° C.; MASS: 584 (M+1) (free).

EXAMPLE 73

A solution of (2R)-1-[3,5-bis(trifluoromethyl)benzoyl]-2-(1H-indol-3-ylmethyl)-4-(4-morpholino-2-butynyl)piperazine in methanol (10 ml) was hydrogenated in the presence of 10% Pd-carbon (50 mg) at room temperature. After completion of the reaction (1 hour and 20 minutes), the reaction mixture was filtered and then chromatographed on silica gel with dichloromethane-methanol (20:1) to give material which on treatment with 4N hydrogen chloride in ethyl acetate solution afforded (2R)-1-[3,5-bis(trifluoromethyl)benzoyl]-2-(1H-indol-3-ylmethyl)-4-(4-morpholinobutyl)piperazine dihydrochloride (165.1 mg).

$[\alpha]_D^{21}$: −7.10° (C=0.5, MeOH); IR (Nujol): 3700–3150, 2720–2450, 1635, 1275, 1180–1080 cm$^{-1}$; NMR (DMSO-d$_6$, δ): 1.70–2.00 (4H, m), 2.95–5.20 (21H, m), 6.60–8.25 (8H, m), 10.95 (1H, s), 11.10–11.80 (2H, m); MASS: 597 (M+1) (free).

EXAMPLE 74

The following compound was obtained according to a similar manner to that of Example 73.

(2R)-1-[3,5-Bis(trifluoromethyl)benzoyl]-2-(3,4-dimethylbenzyl)-4-(5-morpholinopentyl)piperazine Dihydrochloride mp: 235–238° C.; $[\alpha]_D^{22}$: −13.90° (C=0.5, MeOH); IR (Nujol): 3500–3100, 2600, 1630, 1270, 1180–1060 cm$^{-1}$; NMR (DMSO-d$_6$, δ): 1.2–2.0 (6H, m), 2.0–2.5 (8H, m), 2.6–5.2 (19H, m), 6.6–8.3 (6H, m), 11.26 (2H, m); MASS: 600 (M+1) (free).

EXAMPLE 75

(2)-1-[3,5-Bis(trifluoromethyl)benzoyl]-2-(3,4-dimethylbenzyl)piperazine (200 mg) and potassium carbonate (187 mg) were added to a mixture of (E)-4-morpholino-2-butenyl chloride hydrochloride (105 mg) and acetonitrile (3 ml). The resulting mixture was heated at reflux temperature under stirring. After 16 hours, the reaction mixture was evaporated under reduced pressure and the residue was partitioned between ethyl acetate and water. The organic phase was separated and washed with brine, and dried over magnesium sulfate. The solvent was removed in vacuo to leave an oil which was chromatographed on silica gel with dichloromethane-methanol (50:1) as eluent to give material which on treatment with 4N hydrogen chloride in ethyl acetate solution (0.2 ml) afforded (2R)-1-[3,5-bis(trifluoromethyl)benzoyl]-2-(3,4-dimethylbenzyl)-4-[(E)-4-morpholino-2-butenyl]piperazine dihydrochloride (194 mg).

mp: 236–242° C.; $[\alpha]_D^{19.6}$: −10.8° (C=0.3, MeOH); IR (Nujol): 3350, 2900, 1645, 1275, 1185, 1170, 1135 cm$^{-1}$; NMR (DMSO-d$_6$, δ): 2.16 (3H, s), 2.20 (3H, s), 2.60–4.80 (19H, m), 3.91 (4H, t, J=4.8 Hz), 6.04–6.40 (2H, m), 6.74–7.15 (3H, m), 7.61 (2H, s), 8.08 (1H, s); The NMR spectrum of this compound was measured at 90° C.; MASS: 584 (M+1) (free).

EXAMPLE 76

The following compound was obtained according to a similar manner to that of Example 75.

(2R)-1-[3,5-Bis(trifluoromethyl)benzoyl]-2-(1H, indol-3-ylmethyl)-4-[(E)-4-morpholino-2-butenyl]piperazine Dihydrochloride mp: 123–128° C.; $[\alpha]_D^{20}$: −0.2° (C=0.3, MeOH); IR (Nujol): 3350, 2750–2000, 1655, 1635, 1275, 1175, 1125 cm$^{-1}$; NMR (DMSO-d$_6$, δ): 2.60–5.00 (17H, m), 3.89 (4H, t, J=4.8 Ha), 6.00–6.40 (2H, m), 6.70–7.50 (5H, m), 7.80 (2H, s), 8.03 (1H, s), 10.74 (1H, s); The NMR spectrum of this compound was measured at 90° C.; MASS: 595 (M+1) (free).

EXAMPLE 77 to a stirred mixture of (2R)-1-[3,5-bis(trifluoromethyl)benzoyl]-2-(1H-indol-3-ylmethyl)piperazine (0.2 g) and 1-methyl-4-formyl-1H-pyrazole (0.05 g) in dichloromethane (2 ml) under nitrogen atmosphere was added sodium triacetoxyborohydride (151 mg) at room temperature. After 4 hours, the reaction mixture was evaporated under reduced pressure, and ethyl acetate (20 ml) and aqueous sodium hydrogen carbonate solution (10 ml) were added to the residue. The organic layer was separated and washed wit brine, dried over magnesium sulfate and then concentrated under reduced pressure. The resulting residue was purified by column chromatography on silica gel using a mixture of ethyl acetate and methanol (50:1). The obtained product was dissolved in ethyl acetate and treated with 4N hydrogen chloride in ethyl acetate solution to give (2R)-1-[3,5-bis(trifluoromethyl)benzoyl]-2-(1H-indol-3-ylmethyl)-4-[(1-methyl-1H-pyrazol-4-yl)methyl]piperazine hydrochloride (154 mg).

mp: 122–136° C.; $[\alpha]_D^{18.8}$: −8.50° (C=0.3, MeOH); IR (Nujol): 3350, 2750–2000, 1655, 1640, 1275, 1175, 1125 cm$^{-1}$; NMR (DMSO-d$_6$, δ): 2.80–5.20 (14H, m), 6.50–8.30 (1H, m) 10.90 (1H, s), 11.40–11.90 (1H, br s); MASS: 550 (M+1) (free).

EXAMPLE 78

A mixture of (2R-1-[3,5-bis(trifluoromethyl)benzoyl]-2-(3,4-dimethylbenzyl)4-[2-methylsulfonyloxy)ethyl]piperazine (200 mg), 2-ethoxyethylamine (0.044 ml) and triethylamine (0.098 ml) in acetonitrile (5 ml) was refluxed for 1.5 hours. The reaction mixture was concentrated under reduced pressure and the resulting residue was partitioned between ethyl acetate and aqueous sodium hydrogen carbonate solution. The organic layer was washed with brine and dried over magnesium sulfate. After evaporation of the solvent, the residue was purified by column chromatography on silica gel using a mixture of dichloromethane and methanol (20:1) to afford an oily product, which was dissolved in ethyl acetate and treated with 4N hydrogen chloride in ethyl acetate solution to give (2R)-1-[3,5-bis(trifluoromethyl) benzoyl]-2-(3,4-dimethylbenzyl)-4-[2-(2-ethoxyethylamino)ethyl]piperazine dihydrochloride (64.5 mg)

$[\alpha]_D^{22}$: −6.70° (C=0.5, MeOH); IR (Neat): 3400, 2650, 1640, 1430, 1280, 1170, 1150, 900 cm$^{-1}$; NMR (DMSO-d$_6$, δ): 1.63 (3H, m), 2.0–2.30 (6H, m), 2.6–5.3 (20H, m), 6.6–8.3 (6H, m), 9.2–9.6 (1H, br s), 11.2–11.8 (1H, br s); MASS: 560(M+1) (free).

Preparation 8

To a mixture of N-(tert-butylcarbonyl)-4-fluoro-D-phenylalanine (5.25 g), N-benzylglycine benzyl ester hydrochloride (5.41 g) and triethylamine (9.04 ml) in dichloromethane (50 ml) was added 2-chloro-1-methylpyridinium iodide (5.21 g) at room temperature, and the mixture was stirred for 2.5 hours. The mixture was evaporated under reduced pressure, and the resulting residue was dissolved into ethyl acetate. The ethyl acetate solution was washed with diluted hydrochloric acid, saturated sodium hydrogen carbonate aqueous solution and brine successively, and dried over magnesium sulfate. After evaporation of the solvent, the resulting residue was chromatographed on a silica gel using a mixture of toluene and ethyl acetate as an eluent to give (2R)-N-benzyl-N-benzyloxycarbonylmethyl-2-(tert-butoxycarbonylamino)-3-(4-fluorophenyl)propanamide (9.62 g).

$[\alpha]_D^{23.6}$: +9.10° (C=0.5, MeOH); IR (Nujol): 3350, 1735, 1680, 1650 cm$^{-1}$; NMR (DMSO-d$_6$, δ): 1.24, 1.30 (9H, 2s), 2.70–2.90 (2H, m), 3.85–4.80 (5H, m), 5.12 (2H, d, J=3.2 Hz), 6.95–7.45 (14H, m); MASS: 521 (M+1).

Preparation 9

To an ice-cooled solution of (2R)-N-benzyl-N-benzyloxycarbonylmethyl-2-(tert-butoxycarbonylamino)-3-(4-fluorophenyl)propanamide (9.48 g) in dichloromethane (55 ml) was added 4N hydrogen chloride in dioxane solution (54.6 ml). The mixture was stirred at the same temperature for 15 minutes and at room temperature for one hour. After removal of solvent by evaporation, excess aqueous sodium hydrogen carbonate solution was added to the resulting residue. The mixture was warmed at near 50° C. for several minutes and the resulting precipitates were collected by filtration and washed with water and dried in vacuo to give (3R)-1-benzyl-3-(4-fluorobenzyl)piperazine-2,5-dione (5.00 g).

$[\alpha]_D^{27.3}$: −20.30° (C=0.5, MeOH); IR (Nujol): 3200, 3050, 1665, 1220 cm$^{-1}$; NMR (DMSO-d$_6$, δ): 2.80 (1H, d, J=17.3 Hz), 2.88 (1H, dd, J=13.7 Hz, 4.7 Hz), 3.15 (1H, dd, J=13.7 Hz, 4.1 Hz), 3.53 (1H, d, J=17.3 Hz), 4.15 (1H, d, J=14.4 Hz), 4.26 (1H, m), 4.63 (1H, d, J=14.4 Hz), 6.80–7.40 (9H, m), 8.33 (1H, br s); MASS: 313 (M+1).

Preparation 10

To an ice-cooled suspension of lithium aluminum hydride (1.2 g) in tetrahydrofuran (91 ml) was added (3R)-1-benzyl-3-(4-fluorobenzyl)piperazine-2,5-dione (4.95 g) by small portions. The mixture was stirred at the same temperature for 15 minutes and at room temperature for one hour. After removal of solvent by evaporation, aqueous sodium hydrogen carbonate solution was added to the resulting residue. The mixture was warmed at near 50° C. for several minutes and the resulting precipitates were collected by filtration, washed with water and dried in vacuo to give (3R)-1-benzyl-3-(4-fluorobenzyl)piperazine (4.60 g) as an oil.

IR (Neat): 3300, 1215 cm$^{-1}$; NMR (DMSO-d$_6$, δ): 1.90 (2H, m), 2.45–2.90 (5H, m), 3.30–3.45 (4H, m), 6.95–7.35 (9H, m); MASS: 285 (M+1).

Preparation 11

A mixture of (2R)-4-benzyl-1-[3,5-bis(trifluoromethyl) benzoyl]-2-(4-fluorobenzyl)piperazine (7.92 g), ammonium formate (2.38 g) and 10% palladium charcoal (0.79 g) in a mixed solvent of ethanol (80 ml) and water (8 ml) was stirred for 1.5 hours at 60° C. under nitrogen atmosphere. The reaction mixture was cooled to room temperature and filtered through Celite® pad. The filtrate was concentrated under reduced pressure and the residue was dissolved into ethyl acetate. The solution was washed with water and brine successively, dried over magnesium sulfate, and evaporated under reduced pressure to give (2R)-1-[3,5-bis (trifluoromethyl)benzoyl]-2-(4-fluorobenzyl)piperazine (6.04 g) as an oil.

$[\alpha]_D^{27.8}$: −11.70° (C=0.5, MeOH); IR (Neat): 3300, 1630, 1150 cm$^{-1}$; NMR (DMSO-d$_6$, δ): 2.55–3.80 (8H, m) 4.25 (1H, m), 6.90–7.50 (5H, m), 7.64 (1H, br s), 8.13 (1H, br s); MASS: 435 (M+1).

Preparation 12

The following compounds were prepared by a similar manner to that of Preparation 8.

(1) (2R)-N-Benzyl-N-benzyloxycarbonylmethyl-2-(tert-butoxycarbonylamino)-3-(4-methoxyphenyl)propanamide $[\alpha]_D^{24.0}$: +6.60° (C=0.5, MeOH); IR (Neat): 3300, 1740, 1700, 1650, 1240 cm$^{-1}$; NMR (DMSO-d$_6$, δ): 1.27, 1.31 (9H, 2s), 2.76 (2H, m), 3.69, 3.70 (3H, 2s), 3.95–4.90 (5H, m), 5.13 (2H, d, J=4.9 Hz), 6.70–7.36 (14H, m); MASS: 533 (M+1).

(2) (2R)-N-Benzyl-N-benzyloxycarbonylmethyl-2-(tert-butoxycarbonylamino)-3-(4-trifluoromethylphenyl) propanamide $[\alpha]_D^{26.4}$: +9.00° (C=0.5, MeOH); IR (Nujol): 3350, 1735, 1720, 1670, 1650 cm$^{-1}$; NMR (DMSO-d$_6$, δ): 1.19, 1.27 (9H, 2s), 2.90 (2H, m), 4.00–4.75 (5H, m), 5.12 (2H, s), 7.10–7.60 (15H, m); MASS: 571 (M+1).

(3) (2R)-N-Benzyl-N-benzyloxycarbonylmethyl-2-(tert-butoxycarbonylamino)-3-(1-naphthyl)propanamide $[\alpha]_D^{27.7}$: −0.60° (C=0.5, MeOH); IR (Neat): 3300, 2970, 1740, 1700, 1645 cm$^{-1}$; NMR (DMSO-d$_6$, δ): 1.18, 1.26 (9H, 2s), 3.20–3.50 (2H, m), 3.90–5.20 (7H, m), 7.10–8.10 (17H, m); MASS: 553 (M+1).

Preparation 13

The following compounds were prepared by a similar manner to that of Preparation 9.

(1) (3R)-1-Benzyl-3-(4-methoxybenzyl)piperazine-2,5-dione $[\alpha]_D^{27.9}$: −38.60° (C=0.5, MeOH); IR (Nujol): 3250, 1680, 1640, 1245 cm$^{-1}$; NMR (DMSO-d$_6$, δ); 2.60 (1H, d, J=17.2 Hz), 2.80 (1H, dd, J=13.6 Hz, 4.7 Hz), 3.09 (1H, dd, J=13.6 Hz, 3.8 Hz), 3.46 (1H, d, J=17.2 Hz), 3.67 (3H, s), 4.11 (1H, d, J=14.4 Hz), 4.22 (1H, br s), 4.65 (1H, d J=14.4 Hz), 6.63 (2H, d, J=8.7 Hz), 6.93 (2H, d, J=8.7 Hz), 7.10–7.40 (5H, m), 8.30 (1H, br s); MASS: 325 (M+1).

(2) (3R)-1-Benzyl-3-(4-trifluoromethylbenzyl)piperazine-2,5-dione $[\alpha]_D^{26.8}$: −12.00° (C=0.5, MeOH); IR (Nujol): 3250, 1680, 1650 cm$^{-1}$; NMR (DMSO-d$_6$, δ): 2.85 (1H, d, J=17.4 Hz), 3.00 (1H, dd, J=13.4 Hz, 4.8 Hz), 3.25 (1H, dd, J=13.4 Hz, 4.4 Hz), 3.59 (1H, d, J=17.4 Hz), 4.08 (1H, d, J=14.4 Ha), 4.35 (1H, br s), 4.74 (1H, d, J=14.4 Ha), 7.00–7.15 (2H, m), 7.25–7.35 (5H, m), 7.48 (2H, d, J=8.1 Hz), 8.41 (1H, s); MASS: 363 (M+1).

(3) (3R)-1-Benzyl-3-(1-naphthylmethyl)piperazine-2,5-dione

IR (Nujol): 3250, 1685, 1655 cm$^{-1}$; NMR (DMSO-d$_6$, δ): 2.92 (1H, d, J=17.2 Hz), 3.40–3.65 (3H, m), 4.31 (3H, s), 7.03 (2H, m), 7.29 (5H, m), 7.54 (2H, m), 7.82 (1H, dd, J=6.5 Hz, 3.0 Hz), 7.94 (1H, m), 8.14 (1H, m), 8.31 (1H, d, J=3.0 Hz); MASS: 345 (M+1).

Preparation 14

The following compounds were prepared by a similar manner to that of Preparation 10.

(1) (3R)-1-Benzyl-3-(4-methoxybenzyl)piperazine

IR (Neat): 3250, 1240 cm$^{-1}$; NMR (DMSO-d$_6$, δ): 1.60–2.00 (4H, m), 2.40–2.90 (5H, m), 3.30–3.50 (2H, m), 3.70 (3H, s), 6.81 (2H, d, J=8.6 Hz), 7.07 (2H, d, J=8.6 Hz), 7.15–7.40 (6H, m); MASS: 297 (M+1).

(2) (3R)-1-Benzyl-3-(4-trifluoromethylbenzyl)piperazine $[\alpha]_D^{27.2}$: −5.80° (C=0.5, MeOH); IR (Neat): 3250, 2925, 2800, 1320 cm$^{-1}$; NMR (DMSO-d$_6$, δ): 1.72 (1H, t, J=10.0 Hz), 1.91 (1H, m), 2.55–2.95 (6H, m), 3.30–3.50 (3H, m), 7.15–7.35 (6H, m), 7.40 (2H, d, J=8.0 Hz), 7.60 (2H, d, J=8.0 Hz); MASS: 335 (M+1).

(3) (3R)-1-Benzyl-3-(1-naphthylmethyl)piperazine $[\alpha]_D^{27.6}$: −21.80° (C=0.5, MeOH); IR (Neat): 3300, 3050, 2925, 2800 cm$^{-1}$; NMR (DMSO-d$_6$, δ): 1.75–2.05 (2H, m), 2.50–3.60 (9H, m), 7.10–7.65 (9H, m), 7.77 (1H, d, J=7.9 Hz), 7.90 (1H, m), 8.12 (1H, dd, J=7.1 Hz, 2.3 Hz); MASS: 317 (M+1).

Preparation 15

The following compounds were prepared by a similar manner to that of Preparation 11.

(1) (2R)-1-[3,5-Bis(trifluoromethyl)benzoyl]-2-(4-methoxybenzyl)piperazine $[\alpha]_D^{28.1}$: −32.60° (C=0.5, MeOH); IR (Neat): 3300, 1630, 1280 cm$^{-1}$; NMR (DMSO-d$_6$, δ): 2.40–3.55 (9H, m), 3.72 (3H, s), 6.70–8.45 (7H, m); MASS: 447 (M+1).

(2) (2R)-1-[3,5-Bis(trifluoromethyl)benzoyl]-2-(4-trifluoromethylbenzyl)piperazine NMR (DMSO-d$_6$, δ): 2.60–3.70 (9H, m), 7.15–7.40 (2H, m), 7.50–7.75 (4H, m), 8.12 (1H, s); MASS: 485 (M+1).

(3) (2R)-1-[3,5-Bis(trifluoromethyl)benzoyl]-2-(1-naphthylmethyl)piperazine $[\alpha]_D^{28.1}$: +24.70° (C=0.5, MeOH); IR (Neat): 3340, 3050, 2950, 2825, 1630 cm$^{-1}$; NMR (DMSO-d$_6$, δ): 2.50–4.30 (9H, m), 7.10–8.55 (10H, m); MASS: 467 (M+1).

Preparation 16

A mixture of 1-methyl-1H-pyrazole-4-carboxaldehyde (2.0 g) and triethyl phosphonoacetate (4.52 g) in N,N-dimethylformamide (20 ml) was stirred under ice-cooling. After several minutes, sodium hydride (1.09 g, 60% in mineral oil) was added to the mixture, which was stirred for 1 hour at the same temperature. The resulting mixture was poured into ice-water, neutralized with aqueous ammonium acetate solution and extracted with ethyl acetate. The organic layer was washed with brine, dried over magnesium sulfate and concentrated under reduced pressure. The resulting residue was chromatographed on a silica gel using a mixture of hexane and ethyl acetate as an eluent to give ethyl (E)-3-(1-methyl-1H-pyrazol-4-yl)acrylate.

IR (Nujol): 2975, 1700, 1635 cm$^{-1}$; NMR (DMSO-d$_6$, δ): 1.32 (3H, t, J=7.1 Hz), 4.23 (2H, q, J=7.1 Hz), 6.16 (1H, d, J=16.0 Hz), 7.54 (1H, s), 7.55 (1H, d, J=16.0 Hz), 7.69 (1H, s). MASS: 181 (M+1).

Preparation 17

A solution of 2-(E)-3-(1-methyl-1H-pyrazol-4-yl)acrylate (1.04 g) in tetrahydrofuran (50 ml) was hydrogenated over 10% palladium charcoal (0.2 g) at room temperature at 2 atm of hydrogen. After removal of catalyst by filtration through Celite® pad, the filtrate was concentrated under reduced pressure to give ethyl 3-(1-methyl-1H-pyrazol-4-yl) propionate.

IR (Neat): 2950, 1725 cm$^{-1}$; NMR (DMSO-d$_6$, δ): 1.24 (3H, t, J=7.1 Hz), 2.50 (2H, t, J=7.5 Hz), 2.78 (2H, t, J=7.5 Hz), 3.84 (3H, s), 4.13 (2H, q, J=7.1 Hz), 7.18 (1H, s), 7.31 (1H, s); MASS: 183 (M+1).

Preparation 18

To an ice-cooled solution of ethyl 3-(1-methyl-1H-pyrazol-4-yl)propionate (1.05 g) in tetrahydrofuran (10 ml) was added lithium aluminum hydride (0.22 g) under nitrogen atmosphere After the mixture was stirred for 30 minutes, water and 15% sodium hydroxide aqueous solution were added successively to the mixture. The resulting precipitates were filtered off through Celite® pad and the filtrate was extracted with ethyl acetate. The organic layer was washed with water, dried over magnesium sulfate and concentrated under reduced pressure to give 3-(1-methyl-1H-pyrazol-4-yl)-1-propanol.

IR (Neat): 3300, 2930 cm$^{-1}$;
NMR (DMSO—d$_6$, δ): 1.87 (2H, m), 2.55 (2H, t, J=7.6Hz), 3.68 (2H, t, J=6.1Hz), 3.85 (3H, s), 7.16 (1H, s), 7.31 (1H, s)
MASS: 141 (M+1)

Preparation 19

To a solution of oxalyl chloride (0.361 ml) in dichloromethane (10 ml) cooled below −65° C. with a dry ice-acetone bath, a solution of dimethyl sulfoxide (0.381 ml) in dichloromethane (1 ml) was added with efficient stirring over 10 minutes. After 20 minutes below −65° C., a solution of 3-(1-methyl-1H-pyrazol-4-yl)-1-propanol in dichloromethane (2 ml) was added to the mixture over 10 minutes below −65° C. and the mixture was stirred at the same temperature for 20 minutes and then at −45~−40° C. for 30 minutes. After addition of triethylamine dropwise to the mixture over 10 minutes followed by stirring for 15 minutes, 1N hydrochloric acid solution was added to the mixture. The resulting mixture was extracted with a mixture of dichloromethane and methanol several times. The extract was concentrated under reduced pressure and the resulting residue was chromatographed on a silica gel using a mixture of dichloromethane and methanol as an eluent to give 3-(1-methyl-1H-pyrazol-4-yl)-1-propanal.

IR (Neat): 2925, 1720 cm$^{-1}$
NMR (DMSO—d$_6$, δ): 2.65–2.90 (4H, m), 3.86 (3H, s), 7.17 (1H, s), 7.32 (1H, s), 9.80 (1H, s)
Mass: 139 (M+1)

EXAMPLE 79

To a mixture of 3,5-bis(trifluoromethyl)benzoic acid (4.13 g) and pyridine (0.041 ml) in tetrahydrofuran (12.5 ml) was added oxalyl chloride (3.25 g) over 15 minutes at 22°–38° C. and the mixture was stirred at 55° C. for 4 hours. The acid chloride solution obtained above procedure was added to an ice-cooled solution of (3R)-1-benzyl-3-(4-fluorobenzyl)-piperazine (4.51 g) and triethylamine (4.83 g) in dichloromethane (45 ml) under 5° C. for 30 minutes. After being stirred for 2 hours at room temperature, the mixture was washed with water and brine successively, and dried over magnesium sulfate. After evaporation of the solvent, the resulting residue was chromatographed on a silica gel using a mixture of toluene and ethyl acetate as an eluent to give (2R)-4-benzyl-1-[3,5-bis(trifluoromethyl)benzoyl]-2-(4-fluorobenzyl)piperazine 0.87 g) as a syrup.

$[\alpha]_D^{27.5}$: −11.50° (C=0.5, MeOH)
IR (Neat): 1740, 1150 cm$^{-1}$
NMR (DMSO—d$_6$, δ): 2.00–4.40 (11H, m), 6.80–7.50 (10H, m), 7.74 (1H, br s), 8.13 (1H, br)
MASS: 525 (M+1)

EXAMPLE 80

The following compounds were prepared by a similar manner to that of Example 79.

(1) (2R)-4-Benzyl-1-[3,5-bis(trifluoromethyl)benzoyl]-2-(4-methoxybenzyl)piperazine $[\alpha]_D^{28.0}$: −21.40° (C=0.5, MeOH)

IR (Neat): 1740, 1640, 1270 cm$^{-1}$

NMR (DMSO—d$_6$, δ): 1.70–2.40 (3H, m), 2.60–3.80 (11H, m), 6.60–7.60 (10H, m), 7.65–8.55 (2H, m)

MASS: 537 (M+1)

(2) (2R)-4-Benzyl-1-[3,5-bis(trifluoromethyl)benzoyl]-2-(4-trifluoromethylbenzyl)piperazine IR (Neat): 2950, 2800, 1765, 1740, 1640 cm$^{-1}$ NMR (DMSO—d$_6$, δ): 1.70–4.30 (11H, m), 7.13 (1H, d, J=7.8Hz), 7.20–7.70 (10H, m), 8.13 (1H, d, J=7.8Hz)

MASS: 575 (M+1)

(3) (2R)-4-Benzyl-1-[3,5-bis(trifluoromethyl)benzoyl]-2-(1-naphthylmethyl)piperazine $[\alpha]_D^{27.5}$: +9.70° (C=0.5, MeOH)

IR (Nujol): 1640 cm$^{-1}$

NMR (DMSO—d$_6$, δ): 2.00–4.40 (11H, m), 7.00–8.55 (15H, m)

MASS: 557 (M+1)

EXAMPLE 81

The following compound was prepared by a similar manner to that of Example 66.

(2R)-1-[3,5-Bis(trifluoromethyl)benzoyl]-2-(3,4-dimethylbenzyl)-4-[3-(cis-2,6-dimethylmorpholino)propyl]-piperazine dihydrochloride $[\alpha]_D^{21.0}$: -11.10° (C=0.5, MeOH)

IR (Neat): 3400, 2550, 2450, 1640, 1430, 1280, 1175, 1130 cm$^{-1}$

NMR (DMSO—d$_6$, δ): 1.14 (6H, m), 2.05–5.24 (19H, m), 2.10 (3H, s), 2.18 (3H, s), 6.64–8.24 (6H, m)

MASS: 600 (M+1) (free)

Anal. Calcd. for C$_{31}$H$_{39}$F$_6$N$_3$O$_2$·2HCl·2.35H$_2$O C 52.08, H 6.29, N 5.77

Found: C52.08, H 6.44, N 5.88

EXAMPLE 82

The following compounds were obtained according to a similar manner to that of Example 23.

(1) (2R)-1-[3,5-Bis(trifluoromethyl)benzoyl]-2-(3,4-dimethylbenzyl)-4-[N-(3-pyridylmethyl)-3-aminopropyl]-piperazine trihydrochloride $[\alpha]_D^{28.4}$: -13.60° (C=0.25, MeOH)

IR (Neat): 3600–3100, 2800–1950, 1270, 1125 cm$^{-1}$

NMR (DMSO—d$_6$, δ): 2.09–5.20 (24H, m), 6.60–9.00 (10H, m)

MASS: 593 (M+1) (free)

Anal. Calcd. for C$_{21}$H$_{34}$F$_6$N$_4$O·3HCl·4H$_2$O: C 48.10, H 5.86, N 7.24

Found: C 47.89, H 5.75, N 7.02

(2) (2R)-1-[3,5-Bis(trifluoromethyl)benzoyl]-2-(3,4-dimethylbenzyl)-4-(N-morpholino-2-aminoethyl)piperazine dihydrochloride $[\alpha]_D^{28.5}$: -26.80° (C=0.25, MeOH)

IR (Neat): 3600–3000, 2800–2000, 1630, 1274, 1120 cm$^{-1}$

NMR (DMSO—d$_6$, δ): 2.02–5.20 (28H, m), 6.50–8.30 (6H, m)

MASS: 573 (M+1) (free)

Anal. Calcd. for C$_{28}$H$_{34}$F$_6$N$_4$O$_2$19 2HCl·9/2H$_2$O·1/4CH$_3$CO$_2$ C$_2$H$_5$: C46.53, H 6.33, N 7.48

Found: C 46.64, H 6.23, N 6.67

(3) (2R)-1-[3,5-Bis(trifluoromethyl)benzoyl]-2-(3,4-dimethylbenzyl)-4-(N-morpholino-4-amino-2-butynyl)piperazine dihydrochloride $[\alpha]_D^{28.0}$: -9.80° (C=0.25, MeOH)

IR (Neat): 3600–3000, 2600–1950, 1630, 1273, 1120 cm$^{-1}$

NMR (DMSO—d$_6$, δ): 2.10–5.20 (28H, m), 6.20–8.30 (6H, m)

MASS: 597 (M+1) (free)

(4) (2R)-2-[3,5-Bis(trifluoromethyl)benzoyl]-2-(3,4-dimethylbenzyl)-4-[N-methyl-N-(3-pyridylmethyl)-2-aminoethyl]piperazine trihydrochloride $[\alpha]_D^{28.4}$: -11.80° (C=0.25, MeOH)

IR (Nujol): 3600–3100, 2700–1950, 1630, 1275, 1122 cm$^{-1}$

NMR (DMSO—d$_6$, δ): 2.10–5.20 (24H, m), 6.60–7.80 (6H, m), 8.10–8.35 (2H, m), 8.70–8.95 (2H, m)

MASS: 593 (M+1) (free)

Anal. Calcd. for C$_{31}$H$_{34}$F$_6$N$_4$O·3HCl·7/2H$_2$O: C 48.67, H 5.80, N 7.32

Found: C 48.88, H 5.88, N 6.79

(5) (2R)-1-[3,5-Bis(trifluoromethyl)benzoyl]-2-(3,4-dimethylbenzyl)-4-[(E)-N-(3-pyridylmethyl)-4-amino-2-butenyl]piperazine trihydrochloride $[\alpha]_D^{28.5}$: -10.40° (C=0.25, MeOH)

IR (Neat): 3600–3100, 2800–1950, 1630, 1274, 1124 cm$^{-1}$

NMR (DMSO—d$_6$, δ): 2.09–5.20 (22H, m), 6.05–6.25 (2H, m), 6.60–9.00 (10H, m)

MASS: 605 (M+1) (free)

Anal. Calcd. for C$_{32}$H$_{34}$F$_6$N$_4$O·3HCl·5H$_2$O: C 47.80, H 5.89, N 6.97

Found: C 47.81, H 5.53, N 6.48

(6) (2R)-1-[3,5-Bis(trifluoromethyl)benzoyl]-2-(3,4-dimethylbenzyl-4-[(E)-N-morpholino-4-amino-2-butenyl]-piperazine dihydrochloride $[\alpha]_D^{28.5}$: -6.40° (C=0.25, MeOH)

IR (Nujol): 3600–3000, 2750–1950, 1620, 1273, 1120 cm$^{-1}$

NMR (DMSO—d$_6$, δ): 2.09–5.20 (28H, m), 5.80–8.30 (8H, m)

MASS: 599 (M+1) (free)

Anal. Calcd. for C$_{30}$H$_{36}$F$_6$N$_4$O$_2$·2HCl~7/2H$_2$O: C 49.05, H 6.17, N. 7.63

Found: C 49.15, H 6.16, N 7.41

(7) (2R)-1-[3,5-Bis(trifluoromethyl)benzoyl]-2-(2-naphthylmethyl)-4-[N-(3-pyridylmethyl)-2-aminoethyl]piperazine trihydrochloride $[\alpha]_D^{28.5}$: -11.00° (C=0.25, MeOH)

IR (Neat): 3600–3100, 2800–1950, 1630, 1273, 1120 cm$^{-1}$

NMR (DMSO—d$_6$, δ): 2.50–5.20 (16H, m), 7.00–9.00 (14H, m)

MASS: 601 (M+1) (free)

Anal. Calcd. for C$_{32}$H$_{30}$F$_6$N$_4$O·3HCl·4H$_2$O: C 49.15, H 5.28, N 7.16

Found: C 49.26, H 5.24, N 6.80

(8) (2R)-1-[3,5-Bis(trifluoromethyl)benzoyl]-2-(2-naphthylmethyl)-4-(N-morpholino-2-aminoethyl)piperazine dihydrochloride $[\alpha]_D^{28.6}$: -34.80° (C=0.25, MeOH)

IR (Neat): 3600–3100, 2800–1950, 1630, 1273, 1120 cm$^{-1}$

NMR (DMSO—d$_6$, δ): 2.50–5.30 (22H, m), 7.00–8.20 (10H, m)

MASS: 595 (M+1) (free)

Anal. Calcd. for C$_{30}$H$_{32}$F$_6$N$_4$O$_2$·2HCl·11/3H$_2$O: C 49.12, H 5.68, N 7.64

Found: C 49.04, H 5.57, N 7.39

(9) (2R)-1-[3,5-Bis(trifluoromethyl)benzoyl)-2-(2-naphthylmethyl)-4-(N-morpholino-3-aminopropyl)piperazine dihydrochloride $[\alpha]_D^{28.6}$: −40.10° (C=0.25, MeOH)
IR (Nujol): 3650–3100, 2800–1970, 1636, 1275, 1123 cm$^{-1}$
NMR (DMSO—d$_6$, δ): 2.20–5.30 (24H, m), 7.00–8.20 (10H, m), 10.60–11.80 (3H, m)
MASS: 610 (M+1) (free)
Anal. Calcd. for $C_{31}H_{34}F_6N_4O_2 \cdot 2HCl \cdot 3H_2O$: C 50.62, H 5.75, N 7.62
Found: C 50.72, H 5.58, N 6.99

(10) (2R)-1-[3,5-Bis(trifluoromethyl)benzoyl]-2-(2-naphthylmethyl)-4-[(E)-N-(3-pyridylmethyl)-4-amino-2-butenyl]piperazine trihydrochloride
$[\alpha]_D^{28.4}$: −20.40° (C=0.25, MeOH)
IR (Nujol): 3650–3100, 2750–1930, 1620, 1272, 1122 cm$^{-1}$
NMR (DMSO—d$_6$, δ): 3.00–5.30 (16H, m), 6.00–6.30 (2H, m), 7.00–9.10 (14H, m)
MASS: 627 (M+1) (free)
Anal. Calcd. for $C_{34}H_{32}F_6N_4O \cdot 3HCl \cdot 2H_2O$: C 52.89, H 5.09, N 7.26
Found: C 52.73, H 5.09, N 7.16

(11) (2R)-1-[3,5-Bis(trifluoromethyl)benzoyl]-2-(2-naphthylmethyl)-4-[(E)-N-morpholino-4-amino-2-butenyl]piperazine dihydrochloride
$[\alpha]_D^{28.6}$: −13.00° (C=0.25, MeOH)
IR (Neat): 3650–3000, 2750–1970, 1630, 1274 cm$^{-1}$
NMR (DMSO—d$_6$, δ): 2.80–5.30 (22H, m), 6.15–6.50 (2H, m), 7.00–8.25 (10H, m)
MASS: 621 (M+1) (free)

(12) (2R)-1-[3,5-Bis(trifluoromethyl)benzoyl]-2-(2-naphthylmethyl)-4-[N-(3-pyridylmethyl)-3-aminopropyl]piperazine trihydrochloride
$[\alpha]_D^{28.6}$: −24.60° (C=0.25, MeOH)
IR (Nujol): 3600–3100, 2750–1950, 1630, 1273, 1121 cm$^{-1}$
NMR (DMSO—d$_6$, δ): 2.20–5.30 (18H, m), 7.00–9.10 (14H, m)
MASS: 615 (M+1) (free)
Anal. Calcd. for $C_{33}H_{32}F_6N_4O \cdot 3HCl \cdot 10/3H_2O$: C 50.56, H 5.36, N 7.15
Found: C 50.53, H 5.38, N 6.94

EXAMPLE 83

The following compounds were obtained according to a similar manner to that of Example 35.

(1) (2R)-1-[3,5-Bis(trifluoromethyl)benzoyl]-2-(2-naphthylmethyl)-4-(4-homomorpholino-2-butynyl)piperazine dihydrochloride
$[\alpha]_D^{28.0}$: −19.80° (C=0.5, MeOH)
IR (Neat): 3400, 2500, 1640, 1430, 1280, 1175, 1130 cm$^{-1}$
NMR (DMSO—d$_6$, δ): 1.95–5.34 (23H, m), 7.05–8.20 (10H, m)
MASS: 618 (M+1) (free)
Anal. Calcd. for $C_{33}H_{33}F_6N_3O_2 \cdot 2HCl \cdot 2.9H_2O$: C 53.37, H 5.53, N 5.66
Found: C 53.38, H 5.47, N 5.67

(2) (2R)-1-[3,5-Bris(trifluoromethyl)benzoyl]-2-(3-fluoro-4-methylbenzyl)-4-[(E)-4-morpholino-2-butenyl]piperazine dihydrochloride
$[\alpha]_D^{28.0}$: −4.50° (C=0.5, MeOH)
IR (Nujol): 2400, 1645, 1275, 1135 cm$^{-1}$
NMR (DMSO—d$_6$, δ): 2.20 (3H, s), 2.80–5.20 (21H, m), 6.00–8.26 (8H, m)
MASS: 588 (M+1) (free)
Anal. Calcd. for $C_{29}H_{32}F_7N_3O_2 \cdot 2HCl$: C 52.74, H 5.19, N 6.36
Found: C 52.39, H 5.20, N 6.29

(3) (2R)-1-[3,5-Bis(trifluoromethyl)benzoyl]-2-(3-fluoro-4-methylbenzyl)-4-[(E)-4-chloro-2-butenyl]piperazine
IR (Neat): 1640, 1430, 1275, 1130 cm$^{-1}$
NMR (DMSO—d$_6$, δ): 1.91–4.93 (13H, m), 5.71–8.20 (8H, m)
MASS: 537 (M+1)

(4) (2R)-1-[3,5-Bis(trifluoromethyl)benzoyl]-2-(3,4-dimethylbenzyl)-4-(4-morpholino-2-butynyl)piperazine dihydrochloride
mp: 98°–101° C.
NMR (DMSO—d$_6$, δ): 2.0–5.2 (25H, m), 5.74 (1H, br d), 5.89 (1H, br d), 6.6–8.2 (6H, m)
MASS: 578 (M+1) (free)
Anal. Calcd. for $C_{31}H_{33}F_6N_3O \cdot 2HCl \cdot 2H_2O$ C 54.23, H 5.73, N 6.12
Found: C 53.99, H 5.88, N 5.93

EXAMPLE 84

The following compounds were obtained according to a similar manner to that of Example 50.

(1) (2R)-1-[3,5-Bis(trifluoromethyl)benzoyl]-2-(4-fluorobenzyl)-4-(4-thiomorpholino-2-butynyl)piperazine dihydrochloride
mp: 180° C. (dec.)
$[\alpha]_D^{28.0}$: +5.00° (C=0.5, MeOH)
IR (Nujol): 3350, 1630, 1125 cm$^{-1}$
NMR (DMSO—d$_6$, δ): 2.60–4.30 (21H, m), 6.85–7.25 (3H, m), 7.46 (2H, br s), 7.75 (1H, br s), 8.16 (1H, d, J=9.4Hz)
MASS: 588 (M+1) (free)
Anal. Calcd. for $C_{28}H_{28}F_7N_3OS \cdot 2HCl \cdot H_2O$: C 49.56, H 4.75, N 6.19
Found: C 49.47, H 5.13, N 5.93

(2) (2)-1-[3,5-Bis(trifluoromethyl)benzoyl]-2-(4-methoxybenzyl)-4-(4-thiomorpholino-2-butynyl)piperazine dihydrochloride
mp: 197° C. (dec.)
$[\alpha]_D^{28.1}$: −8.60° (C=0.5, MeOH)
IR (Nujol): 2500, 1640, 1275 cm$^{-1}$
NMR (DMSO—d$_6$, δ): 2.60–4.70 (24H, m), 6.70–8.30 (7H, m)
MASS: 600 (M+1) (free)
Anal. Calcd. for $C_{29}H_{31}F_6N_3O_2S \cdot 2HCl \cdot 1.3H_2O$: C 50.05, H 5.16, N 6.04
Found: C 50.06, H 5.36, N 5.77

(3) (2R)-1-[3,5-Bis(trifluoromethyl)benzoyl]-2-(4-trifluoromethylbenzyl)-4-(4-thiomorpholino-2-butynyl)piperazine dihydrochloride
mp: 173° (dec.)
$[\alpha]_D^{28.0}$: +9.60° (C=0.5, MeOH)
IR (Nujol): 2400, 1640 cm$^{-1}$
NMR (DMSO—d$_6$, δ): 2.70–5.30 (21H, m), 7.22 (1H, d, J=7.7Hz), 7.41 (1H, s), 7.50–7.80 (4H, m), 8.18 (1H, d, J=7.0Hz)
MASS: 638 (M+1) (free)
Anal. Calcd. for $C_{29}H_{28}F_9N_3OS \cdot 2HCl \cdot 1.3H_2O$: C 47.46, H 4.48, N 5.73
Found: C 47.43, H 4.51, N 5.51

(4) (2R)-1-[3,5-Bis(trifluoromethyl)benzoyl]-2-(1-naphthylmethyl)-4-(4-thiomorpholino-2-butynyl)piperazine dihydrochloride
mp: 191° C. (dec.)
$[\alpha]_D^{28.0}$: +15.60° (C=0.5, MeOH)
IR (Nujol): 2500, 1635 cm$^{-1}$
NMR (DMSO—d$_6$, δ): 2.65–4.80 (21H, m), 7.10–8.60 (10H, m)

MASS: 620 (M+1) (free)
Anal. Calcd. for $C_{32}H_{31}F_6N_3OS \cdot 2HCl \cdot 0.4H_2O$: C 54.92, H 4.87, N 6.00
Found: C 54.88, H 5.04, N 5.65

EXAMPLE 85

The following compound was obtained according to a similar manner to that of Example 51.

(2R)-1-[3,5-Bis(trifluoromethyl)benzoyl]-2-(3,4-dimethylbenzyl)-4-[3-(1-methyl-1H-pyrazol-4-yl)propyl]piperazine hydrochloride mp: 163°–165° C.
$[\alpha]_D^{25.3}$: −19.80° (C=0.5, MeOH)
IR (Nujol): 2550, 1635 cm$^{-1}$
NMR (DMSO—d$_6$, δ): 1.90–2.25 (6H, m), 3.00–4.00 (15H, br), 6.65–8.25 (8H, m)
MASS: 567 (M+1) (free)
Anal. Calcd. for $C_{29}H_{32}F_6N_4O \cdot HCl \cdot H_2O$: C 56.08, H 5.68, N 9.02
Found: C 56.44, H 5.76, N 8.98

EXAMPLE 86

The following compound was obtained according to a similar manner to that of Example 61.

(2R)-1-[3,5-Bis(trifluoromethyl)benzoyl]-2-(1H-indol-3-ylmethyl)-4-[4-(3,3-dimethylmorpholino)-2-butenyl]piperazine dihydrochloride mp: 210° C. (dec.)
$[\alpha]_D^{28.4}$: +0.63° (C=0.11, MeOH)
IR (Nujol): 3660–3300, 2700–2300, 1640, 1445, 1430, 1370, 1270 cm$^{-1}$
NMR (DMSO—d$_6$, δ): 1.30–1.50 (6H, m), 2.85–5.25 (19H, m), 6.05–6.30 (2H, m), 6.65–8.25 (8H, m), 10.97 (1H, br s), 11.40–12.20 (2H, m)
MASS: 623 (M+1) (free)

EXAMPLE 87

The following compound was obtained according to a similar manner to that of Example 54.

(2R)-1-[3,5-Bis(trifluoromethyl)benzoyl]-2-(3,4-dimethylbenzyl)-4-[3-(3-pyridyl)propyl]piperazine dihydrochloride mp: 163°–168° C.
$[\alpha]_D^{24.7}$: +5.77° (C=1.3, MeOH)
IR (Nujol): 3600–3300, 2700–2300, 1635, 1445, 1430, 1370, 1280 cm$^{-1}$
NMR (DMSO—d$_6$, δ): 1.92–5.22 (29H, m), 6.56–8.28 (6H, m), 11.43 (2H, br s)
MASS: 564 (M+1) (free) C 53.01, H 5.60, N 6.18
Found: C 53.04, H 5.98, N 5.77

What is claimed is:

1. A compound of the formula:

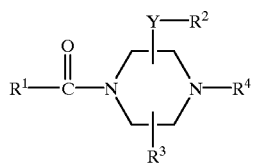

wherein

Y is a bond or lower alkylene, $R^1$ is a substituted or unsubstituted aryl, $R^2$ is a substituted or unsubstituted aryl or indolyl, $R^3$ is hydrogen or lower alkyl, $R^4$ is selected from the group consisting of morpholinyl(lower)alkyl, homomorpholinyl(lower)alkyl, thiomorpholinyl(lower)alkyl, morpholinyl(lower)alkenyl, morpholinyl(lower)alkynyl, thiomorpholinyl(lower)alkenyl, thiomorpholinyl-(lower)alkynyl, morpholinylamino(lower)alkyl, morpholinylamino(lower)alkenyl and morpholinylamino(lower)alkynyl, each of which is optionally substituted, or a pharmaceutically acceptable salt thereof.

2. The compound of claim 1, in which

Y is lower alkylene, $R^1$ is $C_6$–$C_{10}$ aryl optionally having 1 to 3 (mono-, di- or tri-)halo(lower)alkyl, $R^2$ is $C_6$–$C_{10}$ aryl or indolyl, each of which optionally has 1 to 3 substituents selected from the group consisting of lower alkyl, lower alkoxy, (mono, di or tri)halo(lower alkyl) and halogen, and $R^3$ is hydrogen.

3. The compound of claim 2, wherein $R^1$ is phenyl optionally substituted with 1 or 2(mono, di or tri)halo(lower)alkyl, $R^2$ is phenyl, naphthyl or indolyl, each of which optionally has 1 or 2 substituents selected from the group consisting of lower alkyl, lower alkoxy, (mono, di or tri)halo(lower)alkyl and halogen.

4. The compound of claim 3, wherein $R^2$ is phenyl.

5. A process for the preparation of a compound of the formula:

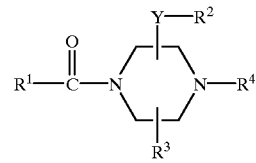

wherein

Y is a bond or lower alkylene, $R^1$ is a substituted or unsubstituted aryl, $R^2$ is a substituted or unsubstituted aryl or indolyl, $R^3$ is hydrogen or lower alkyl, $R^4$ is selected from the group consisting of morpholinyl(lower)alkyl, homomorpholinyl(lower)alkyl, thiomorpholinyl(lower)alkyl, morpholinyl(lower)-alkenyl, morpholinyl(lower)alkynyl, thiomorpholinyl(lower)alkenyl, thiomorpholinyl-(lower)alkynyl, morpholinylamino(lower)alkyl, morpholinylamino(lower)alkenyl and morpholinylamino(lower)alkynyl, each of which is optionally substituted, or a salt thereof, which comprises reacting a compound of the formula:

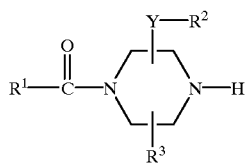

or its reactive derivative at the imino group or a salt thereof with a compound of the formula:

$$W_1-R^4$$

or a salt thereof to provide a compound of the formula:

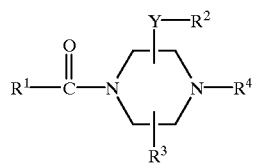

or a salt thereof; and in the above formulas, Y, $R^1$, $R^2$, $R^3$ and $R^4$ are each as defined above, and $W_1$ is a leaving group.

6. The compound of claim 1, in which

Y is methylene, $R^1$ is bis(trifluoromethyl)phenyl, $R^2$ is phenyl or naphthyl, each of which may have 1 or 2 suitable substituent(s) selected from the group consisting of methyl, methoxy, trifluoromethyl and fluorine, or indolyl, $R^3$ is hydrogen, and $R^4$ is thiomorpholinyl($C_1$–$C_4$)alkyl; morpholinyl ($C_2$–$C_4$) alkenyl which may have 1 or 2 methyl; morpholinyl ($C_2$–$C_5$)alkynyl which may have 1 or 2 methyl, methoxymethyl or fluoromethyl; or morpholinylamino ($C_1$–$C_4$)alkyl.

7. The compound of claim 6, which is selected from the group consisting of (1) (2R)-1-[3,5-Bis(trifluoromethyl)benzoyl]-2-(1H-indol-3-ylmethyl)-4-(3-thiomorpholinopropyl)-piperazine, (2) (2R)-1-[3,5-Bis(trifluoromethyl)benzoyl]-4-(4-morpholino-2-butynyl)-2-(2-naphthylmethyl)-piperazine, (3) (2R)-4-(4-Morpholino-2-butynyl)-1-[3,5-bis(trifluoromethyl)benzoyl]-2-(3,4-dimethylbenzyl) piperazine, (4) (2R)-1-[3,5-Bis(trifluoromethyl)benzoyl]-2-(3,4-dimethylbenzyl)-4-[3-(morpholinoamino)propyl]-piperazine and (5) (2R)-1-[3,5-Bis(trifluoromethyl)benzoyl]-2-(3,4-dimethylbenzyl)-4-[(E)-4-morpholino-2-butenyl]-piperazine, or a pharmaceutically acceptable salt thereof.

8. A pharmaceutical composition which comprises, as an active ingredient, a compound of claim 1 or a pharmaceutically acceptable salt thereof in admixture with pharmaceutically acceptable carriers.

9. A method for treating or preventing Tachykinin-mediated diseases which comprises administering an effective amount of a compound of claim 1 or a pharmaceutically acceptable salt thereof to human being or animals.

10. A compound of claim 1 for use as a medicament.

11. A compound according to claim 1 which is (2R)-1-[3,5-Bis(trifluoromethyl)benzoyl]-2-(3,4-dimethylbenzyl)-4-[4-(3,3-dimethylmorpholino)-2-butynyl]piperazine dihydrochloride.

* * * * *